US011299476B2

(12) United States Patent
Newman et al.

(10) Patent No.: US 11,299,476 B2
(45) Date of Patent: Apr. 12, 2022

(54) DOPAMINE D3 RECEPTOR SELECTIVE ANTAGONISTS/PARTIAL AGONISTS; METHOD OF MAKING; AND USE THEREOF

(71) Applicant: THE UNITED STATES OF AMERICA, as represented by THE SECRETARY, DEPARTMENT OF HEALTH AND HUMAN SERVICES, Bethesda, MD (US)

(72) Inventors: Amy Hauck Newman, Phoenix, MD (US); Vivek Kumar, Baltimore, MD (US); Anver Basha Shaik, Baltimore, MD (US)

(73) Assignee: THE UNITED STATES OF AMERICA, AS REPRESENTED BY THE SECRETARY, DEPARTMENT OF HEALTH AND HUMAN SERVICES, Rockville, MD (US)

( * ) Notice: Subject to any disclaimer, the term of this patent is extended or adjusted under 35 U.S.C. 154(b) by 574 days.

(21) Appl. No.: 16/084,093

(22) PCT Filed: Mar. 8, 2017

(86) PCT No.: PCT/US2017/021328
§ 371 (c)(1),
(2) Date: Sep. 11, 2018

(87) PCT Pub. No.: WO2017/160552
PCT Pub. Date: Sep. 21, 2017

(65) Prior Publication Data
US 2020/0291000 A1 Sep. 17, 2020

Related U.S. Application Data

(60) Provisional application No. 62/307,600, filed on Mar. 14, 2016.

(51) Int. Cl.
*C07D 403/12* (2006.01)
*A61P 25/36* (2006.01)
*C07D 405/12* (2006.01)

(52) U.S. Cl.
CPC ............ *C07D 403/12* (2013.01); *A61P 25/36* (2018.01); *C07D 405/12* (2013.01)

(58) Field of Classification Search
CPC .................................................. C07D 403/12
See application file for complete search history.

(56) References Cited

U.S. PATENT DOCUMENTS

| 6,175,015 B1* | 1/2001 | Yuan ............... C07D 209/88 546/167 |
| 7,605,259 B2 | 10/2009 | Newman et al. |
| 8,119,642 B2 | 2/2012 | Newman et al. |
| 8,748,608 B2 | 6/2014 | Newman et al. |

| 2005/0197343 A1 | 9/2005 | Gmeiner et al. |
| 2006/0106030 A1 | 5/2006 | Newman et al. |
| 2008/0051409 A1* | 2/2008 | Gmeiner ............... A61P 25/14 514/252.02 |
| 2010/0068138 A1 | 3/2010 | Newman et al. |
| 2014/0296249 A1 | 10/2014 | Newman et al. |

FOREIGN PATENT DOCUMENTS

| WO | 199731916 A1 | 9/1997 |
| WO | 199734889 A1 | 9/1997 |
| WO | 199806717 A1 | 2/1998 |
| WO | 03028728 A1 | 4/2003 |
| WO | 2004004729 A1 | 1/2004 |
| WO | 2004024878 A2 | 3/2004 |
| WO | 2006015737 A1 | 2/2006 |
| WO | 2006050976 A1 | 5/2006 |
| WO | 2006072608 A2 | 7/2006 |
| WO | 2008009741 A1 | 1/2008 |
| WO | 2014059265 A1 | 4/2014 |
| WO | 2020055725 A1 | 3/2020 |
| WO | 2020055725 A4 | 3/2020 |

OTHER PUBLICATIONS

Wislicenus, J. "Adolph Strecker's Short Textbook of Organic Chemistry" 1881, Spottiswoode: London, pp. 38-39.*
Oh "Dopamine D3 receptor ligand suppresses the expression of levodopa-induced dyskinesia in nonhuman primate model of parkinson's disease"Experimental Neurology 347 (2022) 113920.*
Maramai "Dopamine D3 Receptor Antagonists as Potential Therapeutics for theTreatment of Neurological Diseases" Front. Neurosci. 2016, 10:451.*
Kiss "Neuronal Dopamine D3 Receptors: Translational Implications for Preclinical Research and CNS Disorders"Biomolecules 2021, 11, 104.*
Azar, Marc R. et al.; "Conditioned place aversion is a highly sensitive index of acute opioid dependence and withdrawal"; Psychopharmacology, 170: 2003; p. 42-50.
Chen, Jianyong et al.; "Tranylcypromine Substituted cis-Hydroxycyclobutylnaphthamides as Potent and Selective Dopamine D3 Receptor Antagonists"; Journal of Medicinal Chemistry, 57: 2014; p. 4962-4968.
Goldberg, Steven R.; "Comparable Behavior Maintained Under Fixed-Ratio & Second-Order Schedules of Food Presentation, Cocaine injection or d-Amphetamine Injection in the Squirrel Monkey"; J of Pharmacology & Experimental Therapeutics 186:1, 1973, p. 18-30.
Justinova, Zuzana et al.; "Seif-administration of delta9-tetrahydrocannabinol (THC) by drug naive squirrel monkeys" Pyschopharmacology 169: 2003, pp. 135-140.

(Continued)

*Primary Examiner* — David K O'Dell
(74) *Attorney, Agent, or Firm* — McBee Moore & Vanik IP, LLC

(57) ABSTRACT

Disclosed herein novel dopamine D3 receptor selective antagonists/partial agonists compounds with high affinity and metabolic stability useful for the treatment of psychiatric and neurological disorders and as research and diagnostic tools. Also disclosed are methods of making the compounds.

14 Claims, 12 Drawing Sheets

(56) References Cited

OTHER PUBLICATIONS

Kamal, Ahmed et al.; "Design and synthesis of pyrazole/isoxazole linked arylcinnamides as tubulin polymerization inhibitors and potential antiproliferative agents"; Organic & Biomolecular Chemistry, 13: 2015; pp. 10162-10178.
Kumar, Vivek et al.; "Highly Selective Dopamine D3 Receptor (D3R) Antagonists and Partial Agonists Based on Eticlopride and the D3R Crystal Structure: New Leads for Opioid Dependence Treatment"; Journal of Medicinal Chemistry, 59: 2016: 7634-7650.
Mizuhara, Tsukasa et al.; "Structure-activity relationship study of phenylpyrazole derivatives as a novel class of anti-HIV agents"; Bioorganic & Medicinal Chemistry Letters, 2013, 23, 4557-4561.
Olmstead, Mary C. et al.; "Ultra-low-dose naltrexone suppresses rewarding effects of opiates and aversive effects of opiate withdrawal in rats"; Psychopharmacology, 181: 2005; p. 576-581.
Remington's Pharmaceutical Sciences, 17th ed., Mack Publishing Company, Easton, Pa., p. 1418 (1985).
Xi, Zheng-Xiong et al.; "Blockade of mesolimbic dopamine D3 receptors Inhibits stress-induced reinstatement of cocaine-seeking in rats"; Psychopharmacology, 176: 2004; pp. 57-65.
Xi, Zheng-Xiong et al; "Selective dopamine D3 receptor antagonism by SB-277011A attenuates cocaine reinforcement as assessed by progressive-ratio & variable-cost-variable-payoff fixed-ratio cocaine self-admin in rats"; Eur. J Neurosci, 21: 2005 p. 3427-38.
Yu, Hailei et al.; "Effects of Exogenous Cholecystokinin Octapeptide on Acquisition of Naiozone Precipitated Withdrawal Induced Conditioned Place Aversion in Rats"; Plos One, 7:7, Jul. 2012; pp. 1-8.
Ananthan et al. "Design, Synthesis, & Structure-Activity Relationship Studies of a Series of [4-(4-Carboxamidobutyl)]-1-arylpiperazines: Insights into Structural Features Contributing to Dopamine D3 versus D2 Receptor Subtype Selectivity" J M Chem 57 2014.
International Search Report for International Application No. PCT/US2017/021328, International Filing Date Mar. 8, 2017, dated May 18, 2017, 6 pages.
Kumar, Vivek et al.; "Highly Selective Dopamine D3 Receptor (D3R) Antagonists and Partial Agonists Based on Eticlopride and the D3R Crystal Structure: New Leads for Opioid Dependence Treatment"; Journal of Medicinal Chemistry, V. 59; 2016; p. 7634-7650.
Written Opinion for International Application No. PCT/US2017/021328, International Filing Date Mar. 8, 2017, dated May 18, 2017, 6 pages.
Cummings et al., "The Role of Dopaminergic Imaging in Patients with Symptoms of Dopaminergic System Neurodegeneration", Brian: A Journal of Neurology, pp. 1-21, (2011).
Grundt et al., "Novel Heterocyclic Trans Olefin Analogues of N-{4-[4-(2,3-Dichiorophenyl)piperazin-1-yl]butyl} arylcarboxamides as Selective Probes with High Affinity for the Dopamine D3 Receptor", J. Med. Chem. vol. 48, pp. 839-848, (2005).
Heidbreder et al., "The Role of Central Dopamine D3 Receptors in Drug Addiction: A Review of Pharmacological Evidence", Brian Research Reviews vol. 49, pp. 77-105, (2005).
Joyce et al., "Dopamine D3 Receptor Antagonists as Therapeutic Agents", DDT vol. 10, No. 13, pp. 917-925, (2005).

Newman et al., "Dopamine D3 Receptor Partial Agonists and Antagonists as Potential Drug Abuse Therapeutic Agents", Journal of Medicinal Chemistry vol. 48, No. 11, pp. 3663-3679, (2005).
Newman et al., "N-{4-[4-(2,3-Dichlorophenyl)piperazin-1-yl]butyl, Butenyl and Butynyl}arylcarboxamides as Novel Dopamine D3 Receptor Antagonists", Bioorganic & Medicinal Chemistry Letters 13: pp. 2179-2183, (2003).
Achat-Mendes et al., "Dopamine D3 & D2 Receptor Mechanisms in the Abuse-Related Behavioral Effects of Cocaine: Studies with Preferential Antagonists in Squirrel Monkeys", The J. of Pharmacology & Experimental Therapeutics, V. 334, No. 2, (2010) p. 556-565.
Ashby, CR, Jr. et al.; (2003). "Acute administration of the selective D3 receptor antagonist SB-277011A blocks the acquisition and expression of the conditioned place preference response to heroin in male rats". Synapse 48(3): 154-156.
Beaulieu et al., "The Physiology, Signaling, and Pharmacology of Dopamine Receptors", Pharmacological Reviews vol. 63, No. 1, pp. 182-217, (2011).
Brewer, KL et al. "Dopamine D3 receptor dysfunction prevents anti-nociceptive effects of morphine in the spinal cord" Frontiers in Neural Circuits 8: 62-64, Jun. 11, 2014.
Keck, Thomas M. et al.; "Identifying Medication Targets for Psychostimulant Addiction: Unraveling the Dopamine D3 Receptor Hypothesis" J Med Chem 58(14): 5361-5380, 2015.
Koob, George F. et al.; "Existing and Future Drugs for the Treatment of the Dark Side of Addiction" Annu Rev Pharmacol Toxicol 56: 299-322, 2016.
Koob, George F. et. al.; Neurobioiogy of addiction: a neurocircuitry analysis. Lancet Psychiatry 3(8): 760-773, 2016.
Ledent, Catherine et al., "Unresponsiveness to cannabinoids and reduced addictive effects of opiates in CB1 receptor knockout mice"; Science 283(5400): 401-404, 1999.
Lemberg, Kim et al.; "Morphine, oxycodone, methadone and its enantiomers in different models of nociception in the rat" Anesth Analg 102(6): 1768-1774, 2006.
Leri, Francesco et al.; "Ultra-low-dose naltrexone reduces the rewarding potency of oxycodone and relapse vulnerability in rats"; Pharmacol Biochem Behav 82(2): 252-262, 2005.
Li, Tao et al.; "Role of dopamine D3 receptors in basal nociception regulation and in morphine-induced tolerance and withdrawal"; Brain Research, 1433: 80-84, 2012.
Poyhia, Reino et al.; "Antinociceptive effects and central nervous system depression caused by oxycodone and morphine in rats"; Pharmacology & Toxicology; 70(2): 125-130, 1992.
Rice, Onarae V. et al.; "The acute admin of the selective dopamine D(3) receptor antagonist SB-277011A reverses conditioned place aversion produced by naloxone precipitated withdrawal from acute morphine admin in rats", Synapse 66(1): 85-87, 2012.
Spangler, Rudolph et al.; "Elevated D3 dopamine receptor mRNA in dopaminergic and dopaminoceptive regions of the rat brain in response to morphine"; Mol Brain Res 111(1-2): 74-83, 2003.
Webster, Lynn R. et al.; "Oxytrex minimizes physical dependence while providing effective analgesia: a randomized controlled trial in low back pain" J Pain 7(12): 937-946, 2006.
You Zhi-Bing et al.; "The novel dopamine D3 receptor antagonists/partial agonists CAB2-015 and BAK4-54 inhibit oxycodone-taking and oxycodone-seeking behavior in rats"; Neuropharmacology 126: 190-199, 2017.

* cited by examiner p<0.05, ##p<0.01, compared to saline-treated rats (open bar)

DOPAMINE D3 RECEPTOR SELECTIVE ANTAGONISTS/PARTIAL AGONISTS; METHOD OF MAKING; AND USE THEREOF

CROSS-REFERENCE TO RELATED APPLICATIONS

This application is a U.S. National Stage application of International Application No. PCT/US17/21328, filed Mar. 8, 2017, which claims the benefit of U.S. Provisional Application No. 62/307,600, filed Mar. 14, 2016, each of which is incorporated herein in its entirety.

FIELD OF THE DISCLOSURE

The present disclosure is directed to novel dopamine D3 receptor selective antagonist/partial agonist compounds.

BACKGROUND

Dopamine is a major neurotransmitter in the central nervous system responsible for many neurological processes, including emotion, cognition, reward, motivation and fine motor control. Dopamine signaling is mediated by $D_1$-like ($D_1$ and $D_5$ receptor subtypes) and $D_2$-like ($D_2$, $D_3$ and $D_4$ receptor subtypes). Dopamine $D_3$ receptors ($D_3R$) have been implicated as potential pharmacotherapeutic targets for substance use disorders because of their restricted localization to limbic brain regions, effectiveness in animal models of drug abuse and upregulation in the brains of cocaine addicts.

The high degree of amino acid homology within the binding sites of the dopamine $D_2$-like receptors, and especially between the $D_2$ and $D_3$ dopamine receptor subtypes, has provided a formidable challenge in the pursuit to discover dopamine $D_3$-selective compounds that have drug-like properties.

Therefore, there is a well-recognized need in the art for highly $D_3$-selective antagonists or partial agonists that are metabolically stable and have appropriate drug-like properties for potential translation to treat neuropsychiatric conditions including substance use disorders.

SUMMARY

In an embodiment is a compound of Formula (I), a stereoisomer thereof, a radioisotope thereof, or a pharmaceutically acceptable salt thereof

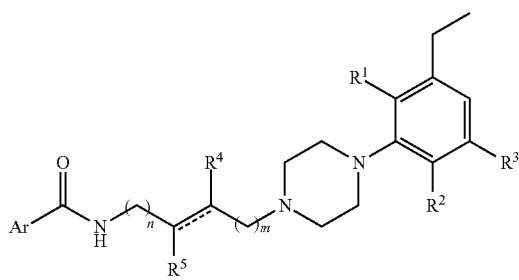

Formula (I)

wherein Ar is a heteroaryl which may be optionally substituted with 1, 2, or 3 substituents where each substituent independently is $C_1$-$C_6$alkyl, $C_1$-$C_6$haloalkyl, $C_1$-$C_6$alkoxy, $C_1$-$C_6$haloalkoxy, —OH, —COOH, amino, nitro, $C_2$-$C_3$alkanoyl group, mono- or di-$C_1$-$C_3$alkylamino, or halogen; n is 1 or 2; m is 1 or 2; $R^1$ is H or halogen; $R^2$ is H, $C_1$-$C_3$alkoxy, or halogen; $R^3$ is H, halogen or $C_1$-$C_3$alkoxy; $R^4$ is H, —OH, or halogen; $R^5$ is H, —OH, or halogen; and $=\!=\!=$ is a single bond, a double bond, a $C_3$-$C_6$ cycloalkyl, or a $C_3$-$C_6$ cycloalkenyl, with the provisos a) and b): a) when $R^1$ is H then at least one of $R^2$ and $R^3$ is not H; and b) when one or both of $R^2$ and $R^3$ is H then $R^1$ is not H.

In another embodiment, a pharmaceutical composition comprises a compound of Formula (I), a stereoisomer thereof, a radioisotope thereof, or a pharmaceutically acceptable salt thereof, and further comprises at least one pharmaceutically acceptable carrier.

In embodiment, a method for treating a substance use disorder, schizophrenia and related mental disorder, a cognitive disorder, impulsivity, obesity, depression, a bipolar disorder, or a dyskinesia associated with Parkinson's disease (PD) or treatment of PD with L-DOPA in a patient, comprises providing a therapeutically effective amount of a compound of Formula (I), a stereoisomer thereof, a radioisotope thereof, or a pharmaceutically acceptable salt thereof to a patient in need thereof. The compound can be administered as a pharmaceutical composition comprising at least one pharmaceutically acceptable carrier. Pharmaceutical packages comprising the pharmaceutical compositions are also disclosed.

BRIEF DESCRIPTION OF DRAWINGS

(FIG. 11 graph A) effects of oxycodone on locomotion over time (from day 2 to day 9) in the presence or absence of compound (±)-29 treatment; (FIG. 11 graph B) time course of (±)-29-induced changes in locomotion (day 1), indicating that it has no effect on locomotor activity by itself; (FIG. 11 graph C) time course of oxycodone-induced changes in locomotion after the first injection of oxycodone (acute effect on day 2), indicating that (±)-29 pretreatment dose-dependently inhibited oxycodone-induced hyperactivity (acute effect); (FIG. 11 graph D) time course of oxycodone priming-induced changes in locomotion in mice after 2 days of withdrawal from the last (vehicle/(±)-29+oxycodone) coadministration (day 9), indicating that repeated (±)-29 pretreatment from day 2 to day 6 produced a long-lasting inhibition in oxycodone-induced increases in locomotion.

DETAILED DESCRIPTION

Figure 1:
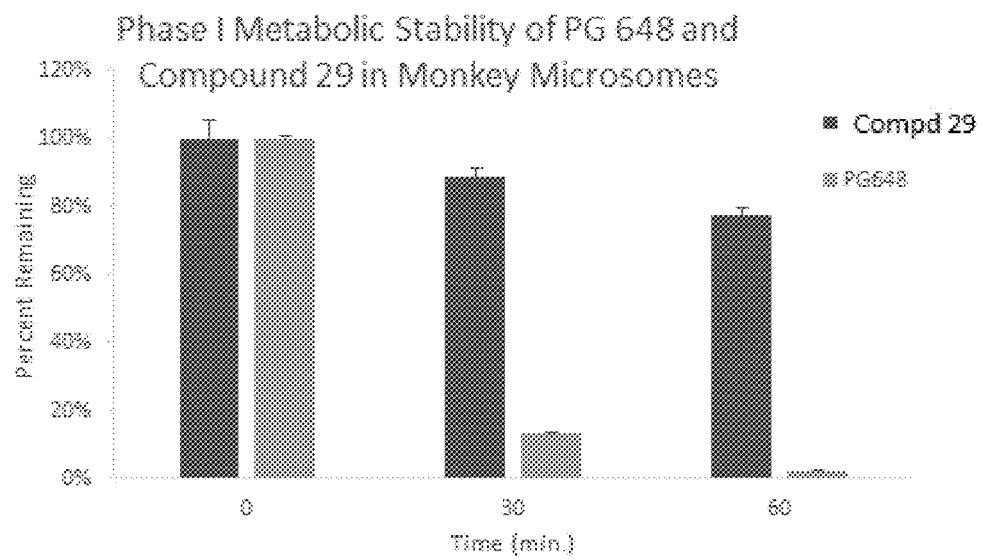
FIG. 1 illustrates the comparative results of compound 29 versus the classic D3 receptor antagonist PG648, compound 1 in a monkey liver microsomal stability assay.

Disclosed are novel dopamine D3 receptor selective antagonists/partial agonists compounds according to Formula (I) unexpectedly having both high affinity for the D3 receptor and excellent metabolic stability not achieved by prior dopamine D3 receptor selective antagonists/partial agonists. Many of the compounds of Formula (I) exhibit high selectivity over the homologous D2 receptor family members e.g. D2 and D4 receptors. The compounds of Formula (I) disclosed herein exhibit improved pharmacological properties, bioavailability, and metabolic stability in vivo over prior 4-phenylpiperazine derivative D3 receptor ligands. The compounds of Formula (I) are useful for treatment of neuropsychiatric disorders. The new compounds were found to be effective in behavioral models of drug abuse and withdrawal, including oxycodone and cannabis. Due to their high potency and D3 receptor selectivity, lower doses of the compounds of Formula (I) may be effective and thus side effect potential is limited.

Also provided are pharmaceutical compositions comprising a compound of Formula (I) or a pharmaceutically acceptable salt thereof and a pharmaceutically acceptable carrier. Such pharmaceutical compositions may contain a compound of Formula (I) as the only active agent or may contain a combination of a compound of Formula (I) and another pharmaceutically active agent. Also provided are methods for the treatment of a neuropsychiatric disorder in a patient in need of such treatment by administration of a compound of Formula (I) or a pharmaceutically acceptable salt thereof, or a pharmaceutical composition thereof.

A compound of Formula (I) or a pharmaceutically acceptable salt thereof, a radioisotope thereof, or a stereoisomer thereof:

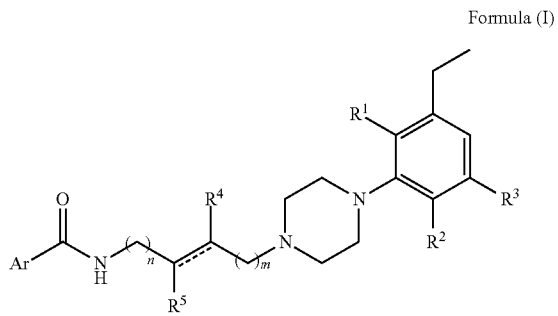

Formula (I)

wherein Ar is a heteroaryl which may be optionally substituted with 1, 2, or 3 substituents where each substituent independently is $C_1$-$C_6$alkyl, $C_1$-$C_6$haloalkyl, $C_1$-$C_6$alkoxy, $C_1$-$C_6$haloalkoxy, —OH, —COOH, amino, nitro, $C_2$-$C_3$alkanoyl group, mono- or di-$C_1$-$C_3$alkylamino, or halogen; specifically Ar is benzofuranyl, benzothienyl, imidazolyl, imidazo[1,2-a]pyridinyl, imidazo[2,1-b]thiazolyl, or indolyl; and more specifically Ar is benzofuranyl, benzothienyl, 4-ethyl-1H-imidazolyl, 4-methyl-1H-imidazolyl, imidazo[1,2-a]pyridinyl, 6-methylimidazo[2,1-b]thiazolyl, or indolyl;

n is 1 or 2;

m is 1 or 2;

$R^1$ is H or halogen (Cl, F, Br, I), specifically H or Cl;

$R^2$ is H, $C_1$-$C_3$alkoxy, or halogen (Cl, F, Br, I), specifically H or —OMe;

$R^3$ is H, halogen (Cl, F, Br, I), or $C_1$-$C_3$alkoxy, specifically H or Cl;

$R^4$ is H, —OH, or halogen, specifically H, —OH or —F;

$R^5$ is H, —OH, or halogen, specifically H, —OH or —F; and

⎓ is a single bond, a double bond (e.g. trans or cis double bond, specifically trans), a cycloalkyl, specifically a $C_3$-$C_6$ cycloalkyl such as a cyclopropyl or cyclohexyl (e.g. trans or cis, specifically trans), or a cycloalkenyl, specifically a $C_3$-$C_6$ cycloalkenyl, with the provisos a) and b):

a) when $R^1$ is H then at least one of $R^2$ and $R^3$ is not H, specifically $R^2$ is $C_1$-$C_3$alkoxy (e.g. —OMe) and $R^3$ is halogen (e.g. Cl); and b) when one or both of $R^2$ and $R^3$ is H then $R^1$ is not H, specifically $R^1$ is halogen (e.g. Cl).

In an embodiment, a compound of Formula (I) or a pharmaceutically acceptable salt thereof wherein $R^1$ is H, $R^2$ is —OMe, and $R^3$ is Cl.

In an embodiment, a compound of Formula (I) or a pharmaceutically acceptable salt thereof wherein $R^1$ is Cl, $R^2$ is H, and $R^3$ is H.

In an embodiment, a compound of Formula (I) or a pharmaceutically acceptable salt thereof wherein $R^1$ is H, $R^2$ is —OMe, $R^3$ is Cl, and Ar is benzofuranyl, benzothienyl, imidazolyl, imidazo[1,2-a]pyridinyl, imidazo[2,1-b]thiazolyl, or indolyl, where Ar is further optionally substituted with 1, 2, or 3 substituents where each substituent independently is $C_1$-$C_6$alkyl, $C_1$-$C_6$haloalkyl, $C_1$-$C_6$alkoxy, $C_1$-$C_6$haloalkoxy, —OH, —COOH, amino, nitro, $C_2$-$C_3$alkanoyl group, or halogen.

In an embodiment, a compound of Formula (I) or a pharmaceutically acceptable salt thereof wherein $R^1$ is Cl, $R^2$ is H, $R^3$ is H, and Ar is benzofuranyl, benzothienyl, imidazolyl, imidazo[1,2-a]pyridinyl, imidazo[2,1-b]thiazolyl, or indolyl, where Ar is further optionally substituted with 1, 2, or 3 substituents where each substituent independently is $C_1$-$C_6$alkyl, $C_1$-$C_6$haloalkyl, $C_1$-$C_6$alkoxy, $C_1$-$C_6$haloalkoxy, —OH, —COOH, amino, nitro, $C_2$-$C_3$alkanoyl group, or halogen.

In an embodiment, a compound of Formula (I) or a pharmaceutically acceptable salt thereof wherein $R^1$ is H, $R^2$ is —OMe, $R^3$ is Cl, and Ar is benzofuranyl, benzothienyl, 4-ethyl-1H-imidazolyl, 4-methyl-1H-imidazolyl, imidazo[1,2-a]pyridinyl, 6-methylimidazo[2,1-b]thiazolyl, or indolyl. Further within this embodiment, m is 1 and n is 1.

In an embodiment, a compound of Formula (I) or a pharmaceutically acceptable salt thereof wherein $R^1$ is Cl, $R^2$ is H, $R^3$ is H, and Ar is benzofuranyl, benzothienyl, 4-ethyl-1H-imidazolyl, 4-methyl-1H-imidazolyl, imidazo[1,2-a]pyridinyl, 6-methylimidazo[2,1-b]thiazolyl, or indolyl. Further within this embodiment, m is 1 and n is 1.

In an embodiment, a compound of Formula (I) or a pharmaceutically acceptable salt thereof wherein $R^1$ is H, $R^2$ is —OMe, $R^3$ is Cl, and Ar is benzofuranyl, benzothienyl, 4-ethyl-1H-imidazolyl, 4-methyl-1H-imidazolyl, imidazo[1,2-a]pyridinyl, 6-methylimidazo[2,1-b]thiazolyl, or indolyl. Further within this embodiment one of $R^4$ and $R^5$ is H and the other is —OH or —F.

In an embodiment, a compound of Formula (I) or a pharmaceutically acceptable salt thereof wherein $R^1$ is Cl, $R^2$ is H, $R^3$ is H, and Ar is benzofuranyl, benzothienyl, 4-ethyl-1H-imidazolyl, 4-methyl-1H-imidazolyl, imidazo[1,2-a]pyridinyl, 6-methylimidazo[2,1-b]thiazolyl, or indolyl. Further within this embodiment one of $R^4$ and $R^5$ is H and the other is —OH or —F.

In an embodiment, a compound of Formula (I) or a pharmaceutically acceptable salt thereof wherein $R^1$ is H; $R^2$ is —OMe; $R^3$ is Cl; Ar is benzofuranyl or indolyl; n is 1 or 2; m is 1 or 2; $R^4$ is H, —OH, or halogen, specifically H, —OH, or F; $R^5$ is H, —OH, or halogen, specifically H, —OH or F; and $\overline{\overline{\phantom{==}}}$ is a single bond, a double bond (e.g. trans or cis double bond, specifically trans), a $C_3$-$C_6$ cycloalkyl such as a cyclopropyl or cyclohexyl (e.g. trans or cis, specifically trans), or a $C_3$-$C_6$ cycloalkenyl.

In an embodiment, a compound of Formula (I) or a pharmaceutically acceptable salt thereof wherein $R^1$ is Cl; $R^2$ is H; $R^3$ is H; Ar is benzofuranyl or indolyl; n is 1 or 2; m is 1 or 2; $R^4$ is H, —OH, or halogen, specifically H, —OH, or F; $R^5$ is H, OH, or halogen, specifically H, —OH, or F; and $\overline{\overline{\phantom{==}}}$ is a single bond, a double bond (e.g. trans or cis double bond, specifically trans), a $C_3$-$C_6$ cycloalkyl such as a cyclopropyl or cyclohexyl (e.g. trans or cis, specifically trans), or a $C_3$-$C_6$ cycloalkenyl.

Also included in this disclosure are compounds of Formula (I) having specific structures as set out in Tables 1A and 1B herein and set out in the table below.

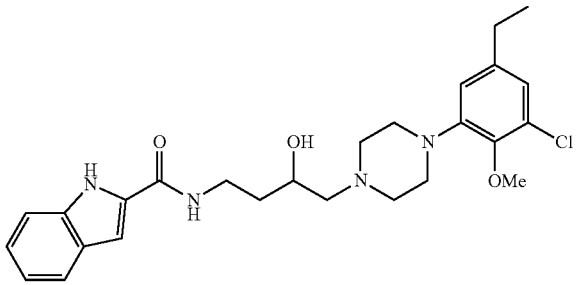

N-(4-(4-(3-chloro-5-ethyl-2-methoxyphenyl)piperazin-1-yl)-3-hydroxybutyl)-1H-indole-2-carboxamide(±)-29)

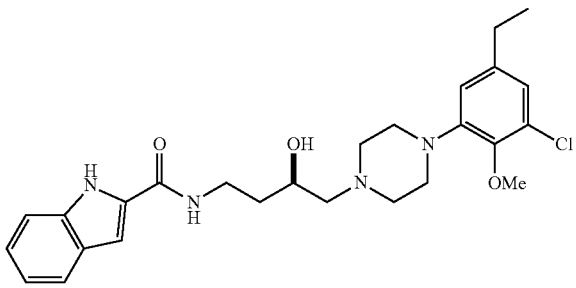

(R)-N-(4-(4-(3-chloro-5-ethyl-2-methoxyphenyl)piperzan-1-yl)-3-hydroxybutyl)-1H-indole-2-carboxamide ((R)-29)

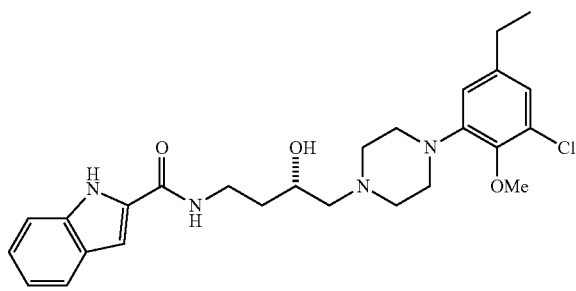
(S)-N-(4-(4-(3-chloro-5-ethyl-2-methoxyphenyl)piperazin-1-yl)-3-hydroxybutyl)-1H-indole-2-carboxamide ((S)-29
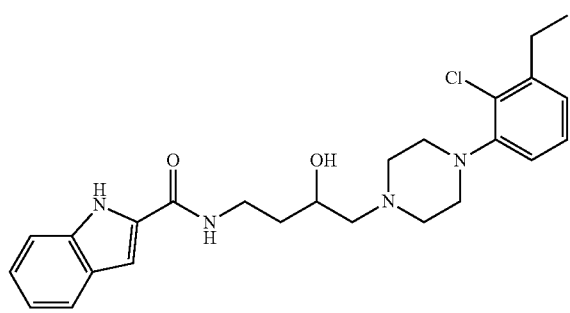
N-(4-(4-(2-chloro-3-ethylphenyl)piperazin-1-yl)-3-hydroxybutyl)-1H-indole-2-carboxamide((±)-19)
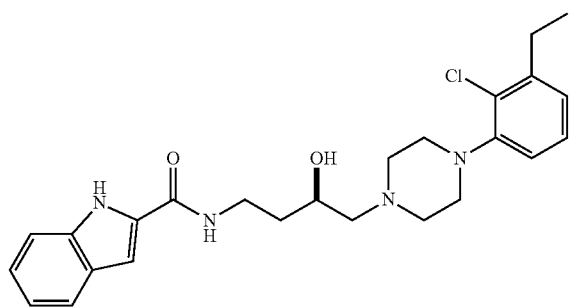
(R)-N-(4-(4-(2-chloro-3-ethylphenyl)piperazin-1-yl)-3-hydroxybutyl)-1H-indole-2-carboxamide ((R-19)
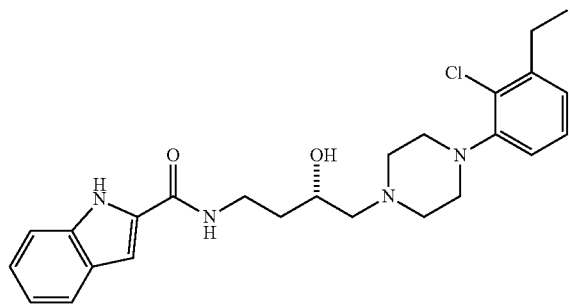
(S)-N-(4-(4-(2-chloro-3-ethylphenyl)piperazin-1-yl)-3-hydroxybutyl)-1H-indole-2-carboxamide ((S)-19)

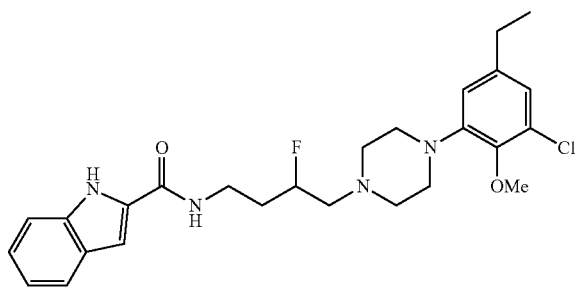
N-(4-(4-(3-chloro-5-ethyl-2-methoxyphenyl)piperazin-1-yl)-3-fluorobutyl)-1H-indole-2-carboxamide
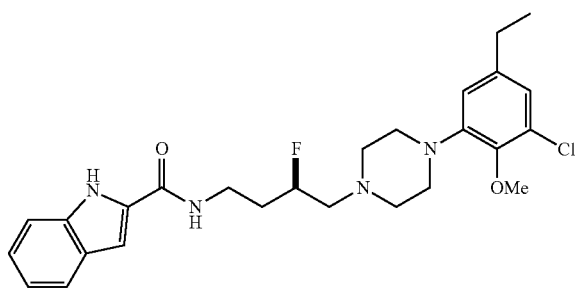
(R)-N-(4-(4-(3-chloro-5-ethyl-2-methoxyphenyl)piperazin-1-yl)-3-fluorobutyl)-1H-indole-2-carboxamide
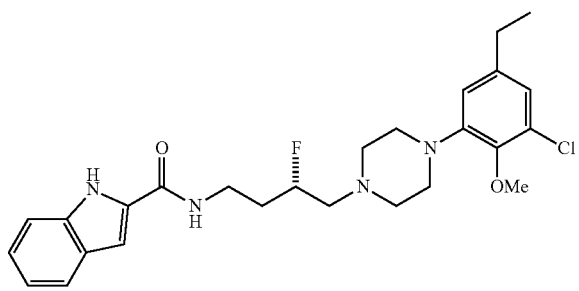
(S)-N-(4-(4-(3-chloro-5-ethyl-2-methoxyphenyl)piperazin-1-yl)-3-fluorobutyl)-1H-indole-2-carboxamide
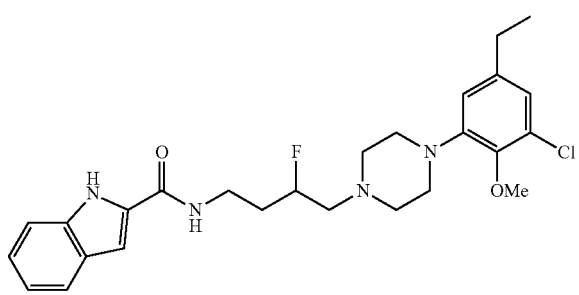
N-(4-(4-(3-chloro-5-ethyl-2-methoxyphenyl)piperazin-1-yl)-3-fluorobutyl)benzofuran-2-carboxamide

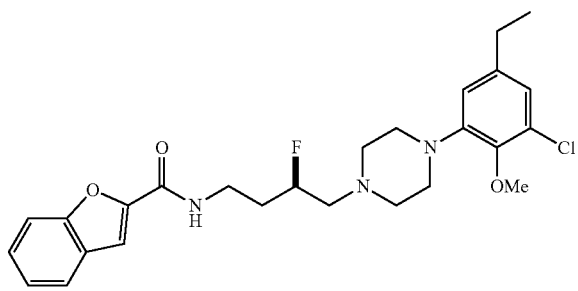
(R)-N-(4-(4-(3-chloro-5-ethyl-2-methoxyphenyl)piperazin-1-yl)-3-fluorobutyl)benzofuran-2-carboxamide
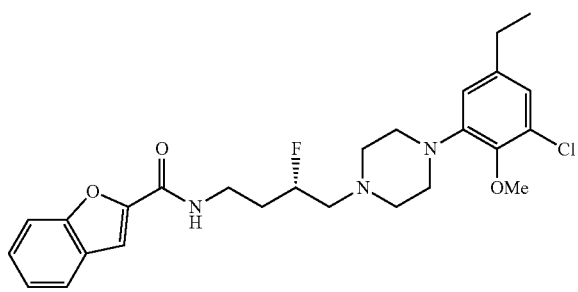
(S)-N-(4-(4-(3-chloro-5-ethyl-2-methoxyphenyl)piperazin-1-yl)-3-fluorobutyl)benzofuran-2-carboxamide
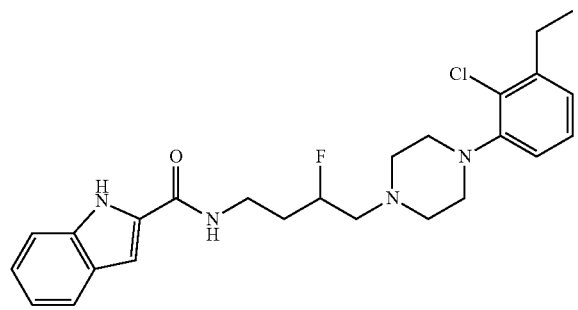
N-(4-(4-(2-chloro-3-ethylphenyl)piperazin-1-yl)-3-fluorobutyl)-1H-indole-2-carboxamide
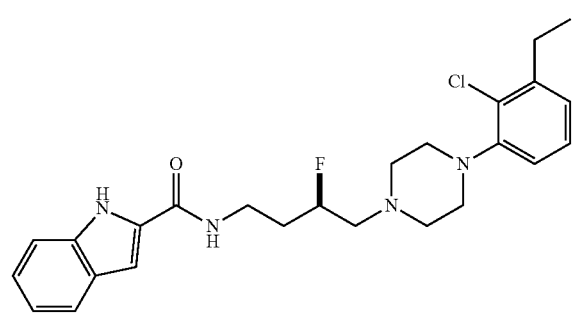
(R)-N-(4-(4-(2-chloro-3-ethylphenyl)piperazin-1-yl)-3-fluorobutyl)-1H-indole-2-carboxamide

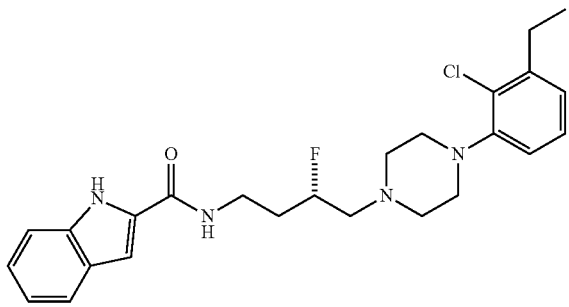

(S)-N-(4-(4-(2-chloro-3-ethylphenyl)piperazin-1-yl)-3-fluorobutyl)-1H-indole-2-carboxamide

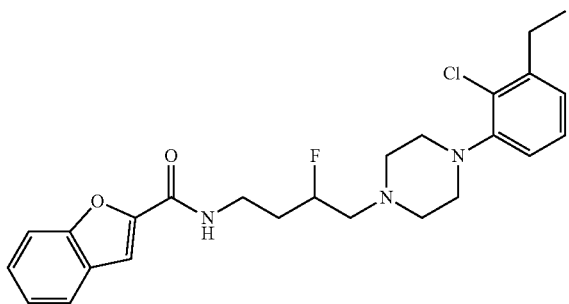

N-(4-(4-(2-chloro-3-ethylphenyl)piperazin-1-yl)-3-fluorobutyl)benzofuran-2-carboxamide

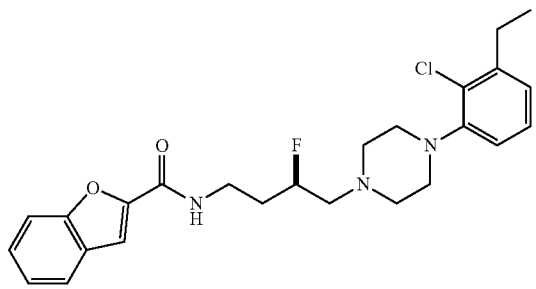

(R)-N-(4-(4-(2-chloro-3-ethylphenyl)piperazin-1-yl)-3-fluorobutyl)benzofuran-2-carboxamide

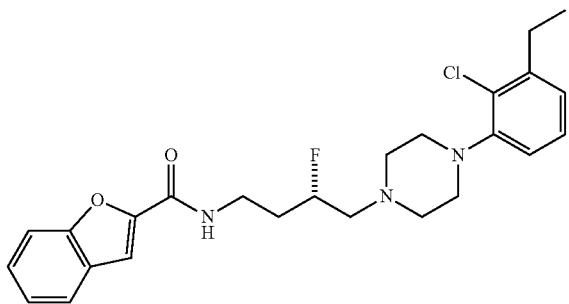

(S)-N-(4-(4-(2-chloro-3-ethylphenyl)piperazin-1-yl)-3-fluorobutyl)benzofuran-2-carboxamide The compounds are described using standard nomenclature. Unless defined otherwise, all technical and scientific terms used herein have the same meaning as is commonly understood by one of ordinary skill in the art to which this disclosure belongs. Unless clearly contraindicated by the context each compound name includes the free acid or free base form of the compound as well hydrates of the compound and all pharmaceutically acceptable salts of the compound.

The term "Formula (I)", as used herein, encompasses all compounds that satisfy Formula (I), including any enantiomers, racemates and stereoisomers, as well as all pharmaceutically acceptable salts and radioisotopes of such compounds. The phrase "a compound of Formula (I)" includes all subgeneric groups of Formula (I), and so forth, as well as all forms of such compounds, including salts and hydrates, unless clearly contraindicated by the context in which this phrase is used.

Formula (I) includes all subformulae thereof. In certain situations, the compounds of Formula (I) may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In these situations, single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example, a chiral high performance liquid chromatography (HPLC) column.

Where a compound exists in various tautomeric forms, the compound is not limited to any one of the specific tautomers, but rather includes all tautomeric forms. All isotopes of atoms occurring in the present compounds are contemplated. Isotopes include those atoms having the same atomic number but different mass numbers. By way of general example, and without limitation, isotopes of hydrogen include tritium and deuterium; isotopes of carbon include $^{11}C$, $^{13}C$, and $^{14}C$; and an isotope of fluorine includes $^{18}F$.

The term "active agent", as used herein, means a compound of Formula (I) that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound, crystalline forms, non-crystalline forms, and any polymorphs of the compound are included. All forms are contemplated herein regardless of the methods used to obtain them.

A dash ("-") that is not between two letters or symbols is used to indicate a point of attachment for a substituent. For example, —$(CH_2)C_3$-$C_8$cycloalkyl is attached through carbon of the methylene ($CH_2$) group.

"Alkanoyl" is an alkyl group as defined herein, covalently bound to the group it substitutes by a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—.

The term "alkyl", as used herein, means a branched or straight chain saturated aliphatic hydrocarbon group having the specified number of carbon atoms, generally from 1 to about 12 carbon atoms. The term $C_1$-$C_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_6$alkyl, $C_1$-$C_4$alkyl, and $C_1$-$C_2$alkyl. When $C_0$-$C_n$ alkyl is used herein in conjunction with another group, for example, (cycloalkyl)$C_0$-$C_4$alkyl, the indicated group, in this case cycloalkyl, is either directly bound by a single covalent bond ($C_0$), or attached by an alkyl chain having the specified number of carbon atoms, in this case 1, 2, 3, or 4 carbon atoms. Examples of alkyl include, but are not limited to, methyl, ethyl, n-propyl, isopropyl, n-butyl, 3-methylbutyl, t-butyl, n-pentyl, and sec-pentyl.

The term "alkoxy" represents an alkyl group as defined above with the indicated number of carbon atoms attached through an oxygen bridge. Examples of alkoxy include methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

The term "aryl", as used herein, means aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Bicyclic aryl groups may be further substituted with carbon or non-carbon atoms or groups. Bicyclic aryl groups may contain two fused aromatic rings (naphthyl) or an aromatic ring fused to a 5- to 7-membered non-aromatic cyclic group that optionally contains 1 or 2 heteroatoms independently chosen from N, O, and S, for example, a 3,4-methylenedioxy-phenyl group. Aryl groups include, for example, phenyl, naphthyl, including 1-naphthyl and 2-naphthyl, and bi-phenyl.

The term "cycloalkyl", as used herein, indicates a saturated hydrocarbon ring group, having only carbon ring atoms and having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norborane or adamantane.

The term "cycloalkenyl", as used herein, means a saturated hydrocarbon ring group, comprising one or more unsaturated carbon-carbon bonds, which may occur in any stable point of the ring, and having the specified number of carbon atoms. Monocyclic cycloalkenyl groups typically have from 3 to about 8 carbon ring atoms or from 3 to 7 (3, 4, 5, 6, or 7) carbon ring atoms. Cycloalkenyl substituents may be pendant from a substituted nitrogen or carbon atom, or a substituted carbon atom that may have two substituents may have a cycloalkenyl group, which is attached as a spiro group. Examples of cycloalkenyl groups include cyclopropenyl, cyclobutenyl, cyclopentenyl, or cyclohexenyl as well as bridged or caged saturated ring groups such as norbornene.

The term "heteroaryl", as used herein, indicates a stable 5- to 7-membered monocyclic or 7- to 10-membered bicyclic heterocyclic ring which contains at least 1 aromatic ring that contains from 1 to 4, or specifically from 1 to 3, heteroatoms chosen from N, O, and S, with remaining ring atoms being carbon. When the total number of S and O atoms in the heteroaryl group exceeds 1, theses heteroatoms are not adjacent to one another. Specifically, the total number of S and O atoms in the heteroaryl group is not more than 2, more specifically the total number of S and O atoms in the heteroaryl group is not more than 1. A nitrogen atom in a heteroaryl group may optionally be quaternized. When indicated, such heteroaryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a [1,3]dioxolo[4,5-c]pyridyl group. In certain embodiments 5- to 6-membered heteroaryl groups are used. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, and 5,6,7,8-tetrahydroisoquinoline.

"Haloalkyl" includes both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Haloalkoxy" is a haloalkyl group as defined herein attached through an oxygen bridge (oxygen of an alcohol radical).

"Halo" or "halogen" is any of fluoro, chloro, bromo, and iodo.

"Mono- and/or di-alkylamino" is a secondary or tertiary alkyl amino group, wherein the alkyl groups are independently chosen alkyl groups, as defined herein, having the indicated number of carbon atoms. The point of attachment of the alkylamino group is on the nitrogen. Examples of mono- and di-alkylamino groups include ethylamino, dimethylamino, and methyl-propyl-amino.

The term "substituted", as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes aromatic moieties, the corresponding partially unsaturated ring replaces the aromatic ring. For example, a pyridyl group substituted by oxo is a pyridone. A stable compound or stable structure is meant to imply a compound that is sufficiently robust to survive isolation from a reaction mixture, and subsequent formulation into an effective therapeutic agent.

Unless otherwise specified substituents are named into the core structure. For example, it is to be understood that when (cycloalkyl)alkyl is listed as a possible substituent the point of attachment of this substituent to the core structure is in the alkyl portion, or when arylalkyl is listed as a possible substituent the point attachment to the core structure is the alkyl portion.

Suitable groups that may be present on a "substituted" or "optionally substituted" position include, but are not limited to, halogen; cyano; hydroxyl; nitro; azido; alkanoyl (such as a $C_2$-$C_6$ alkanoyl group such as acyl or the like); carboxamido; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothienyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

The term "dosage form", as used herein, means a unit of administration of an active agent. Examples of dosage forms include tablets, capsules, injections, suspensions, liquids, emulsions, creams, ointments, suppositories, inhalable forms, transdermal forms, and the like. An exemplary dosage form is a solid oral dosage form.

The term "pharmaceutical compositions", as used herein, are compositions comprising at least one active agent, such as a compound or salt of Formula (I), and at least one other substance, such as a carrier. Pharmaceutical compositions meet the U.S. FDA's GMP (good manufacturing practice) standards for human or non-human drugs. The pharmaceutical compositions can be formulated into a dosage form.

The term "pharmaceutically acceptable salt", as used herein, includes derivatives of the disclosed compounds in which the parent compound is modified by making inorganic and organic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are used, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in

*Remington's Pharmaceutical Sciences,* 17th ed., Mack Publishing Company, Easton, Pa., p. 1418 (1985).

The term "carrier", as used herein, applied to pharmaceutical compositions refers to a diluent, excipient, or vehicle with which an active compound is provided.

The term "patient", as used herein, is a human in need of medical treatment. Medical treatment can include treatment of an existing condition, such as a disease or disorder, prophylactic or preventative treatment, or diagnostic treatment.

The term "providing", as used herein, means giving, administering, selling, distributing, transferring (for profit or not), manufacturing, compounding, or dispensing.

The term "providing a compound of Formula (I) with at least one additional therapeutic agent", as used herein, means the compound of Formula (I) and the additional active agent(s) are provided simultaneously in a single dosage form, provided concomitantly in separate dosage forms, or provided in separate dosage forms for administration separated by some amount of time that is within the time in which both the compound of Formula (I) and the at least one additional active agent are within the blood stream of a patient. The compound of Formula (I) and the additional active agent need not be prescribed for a patient by the same medical care worker. The additional active agent or agents need not require a prescription. Administration of the compound of Formula (I) or the at least one additional active agent can occur via any appropriate route, for example, oral tablets, oral capsules, oral liquids, inhalation, injection, suppositories or topical contact.

The term "treatment", as used herein, includes providing a compound of Formula (I), either as the only active agent or together with at least one additional active agent sufficient to: (a) prevent a disease or a symptom of a disease from occurring in a patient who may be predisposed to the disease but has not yet been diagnosed as having it; (b) inhibiting the disease, i.e. arresting its development; and (c) relieving the disease, i.e., causing regression of the disease. "Treating" and "treatment" also means providing a therapeutically effective amount of a compound of Formula (I), as the only active agent or together with at least one additional active agent to a patient suffering from substance use disorders, schizophrenia and related mental disorders, cognitive disorders, impulsivity, obesity, depression, a bipolar disorder, or dyskinesias associated with Parkinson's disease (PD) or treatment of PD with L-DOPA.

The term "therapeutically effective amount" of a pharmaceutical composition, as used herein, means an amount effective, when administered to a patient, to provide a therapeutic benefit such as an amelioration of symptoms, e.g., to treat a patient suffering from a substance use disorder, schizophrenia and related mental disorder, a cognitive disorder, impulsivity, obesity, depression, a bipolar disorder, or a dyskinesia associated with Parkinson's disease (PD) or treatment of PD with L-DOPA.

The compounds can be administered as the neat chemical, or administered as a pharmaceutical composition. Accordingly, an embodiment provides pharmaceutical compositions comprising a compound or pharmaceutically acceptable salt of Formula (I), together with a pharmaceutically acceptable carrier. The pharmaceutical composition may contain a compound or salt of Formula (I) as the only active agent, or may contain one or more additional active agents.

The compounds may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, for example, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional active agents may be included in a pharmaceutical composition, which do not substantially interfere with the activity of the compound of Formula (I).

The pharmaceutical compositions can be formulated for oral administration. These compositions contain between 0.1 and 99 weight percent ("wt. %") of a compound of Formula (I), and usually at least about 5 wt. %. Some embodiments contain from about 25 wt. % to about 50 wt. % or from about 5 wt. % to about 75 wt. % of a compound of Formula (I).

The pharmaceutical composition can be formulated in a package comprising the pharmaceutical composition containing a compound of Formula (I) or a salt thereof in a container and further comprising instructions for using the composition in order to elicit a therapeutic effect in a patient.

The pharmaceutical composition can also be formulated in a package comprising the pharmaceutical composition of Formula (I) or a salt thereof in a container and further comprising instructions for using the composition to treat a patient suffering from, for example, substance use disorders, schizophrenia and related mental disorders, cognitive disorders, impulsivity, obesity, depression, a bipolar disorder, or dyskinesias associated with Parkinson's disease (PD) or treatment of PD with L-DOPA.

In an embodiment, a method of treating a substance use disorder, schizophrenia or a related mental disorder, a cognitive disorder, impulsivity, obesity, depression, a bipolar disorder, or a dyskinesia associated with Parkinson's disease (PD) or treatment of PD with L-DOPA in a patient comprises providing an effective amount of a compound or salt of Formula (I) to a patient in need of such treatment. Alternatively, the compound of Formula (I) may be provided in the form of a pharmaceutical composition.

In an embodiment, a method for treating substance use disorders (e.g. cocaine, heroin, methamphetamine, opioids (including hydromorphone, hydrocodone, oxycodone, oxymorphone, ethylmorphine buprenorphine, morphine, codeine, etc.), cannabis, alcohol, nicotine, and the like), schizophrenia and related mental disorders, cognitive disorders, impulsivity, obesity, depression, a bipolar disorder, or dyskinesias associated with Parkinson's disease (PD) or treatment of PD with L-DOPA comprises providing an effective amount of a compound or salt of Formula (I) to a patient in need of such treatment. Alternatively, the compound of Formula (I) may be provided in the form of a pharmaceutical composition.

The compounds of Formula (I) can be used as research tools in the study of dopamine receptor subtypes or used as biomarkers or medical diagnostic tools, e.g., through positron emission tomography (PET) ligand development, or magnetic resonance imaging (MRI). In an embodiment, the compounds of Formula (I) comprise a radioisotope as described herein ($^{11}$C, $^{18}$F, etc.) for use to render the compound as a suitable PET ligand.

This invention is further illustrated by the following examples that should not be construed as limiting.

EXAMPLES

Example 1: Synthesis of Piperazine Butandiyl/2-Butendiyl Arylcarboxamide Derivatives Anhydrous solvents were purchased from Aldrich and were used without further purification except for tetrahydrofuran, which was freshly distilled from sodium-benzophenone ketyl. All other chemicals and reagents were purchased from Sigma-Aldrich Co. LLC, Combi-Blocks, TCI America, Acros Organics, Maybridge, and Alfa Aesar. All amine final products were converted into the oxalate salt. Spectroscopic data and yields refer to the free base form of compounds. Teledyne ISCO CombiFlash Rf or glass flash column chromatography was performed using silica gel (EMD Chemicals, Inc.; 230-400 mesh, 60 Å). $^{1}$H and $^{13}$C NMR spectra were acquired using a Varian Mercury Plus 400 spectrometer at 400 MHz and 100 MHz, respectively. Chemical shifts are reported in parts-per-million (ppm) and referenced according to deuterated solvent for $^{1}$H spectra (CDCl$_3$, 7.26, CD$_3$OD, 3.31 or DMSO-d$_6$, 2.50) and $^{13}$C spectra (CDCl$_3$, 77.2, CD$_3$OD, 49.0 or DMSO-d$_6$, 39.5). Gas chromatography-mass spectrometry (GC/MS) data were acquired (where obtainable) using an Agilent Technologies (Santa Clara, Calif.) 6890N GC equipped with an HP-5MS column (cross-linked 5% PH ME siloxane, 30 m×0.25 mm i.d.×0.25 µm film thickness) and a 5973 mass-selective ion detector in electron-impact mode. Ultrapure grade helium was used as the carrier gas at a flow rate of 1.2 mL/minute (min). The injection port and transfer line temperatures were 250 and 280° C., respectively, and the oven temperature gradient used was as follows: the initial temperature (100° C.) was held for 3 min and then increased to 295° C. at 15° C./min over 13 min, and finally maintained at 295° C. for 10 min. Combustion analysis was performed by Atlantic Microlab, Inc. (Norcross, Ga.) and the results agree within ±0.4% of calculated values. cLogP and polar surface area (PSA) values were calculated using ChemDraw Professional Ultra 15.0. Melting point determination was conducted using a Thomas-Hoover melting point apparatus and are uncorrected. On the basis of NMR and combustion data, all final compounds are ≥95% pure.

Abbreviations used: CDI, 1,1'-carbonyldiimidazole; DMF, dimethylformamide; h, hour; min, minute; RT, room temperature; THF, tetrahydrofuran.

Generalized synthetic strategies used for the piperazine butandiyl/2-butendiyl arylcarboxamide derivatives are shown in Schemes 1-5.

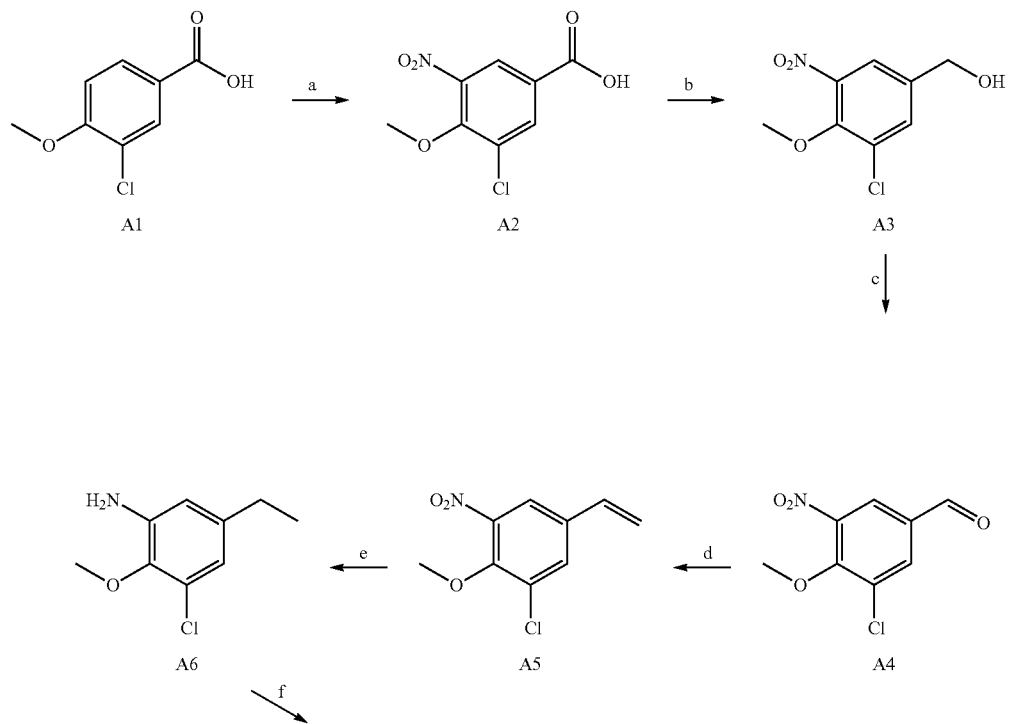

Scheme 1. Sythesis of (±), (R), and (S)-29

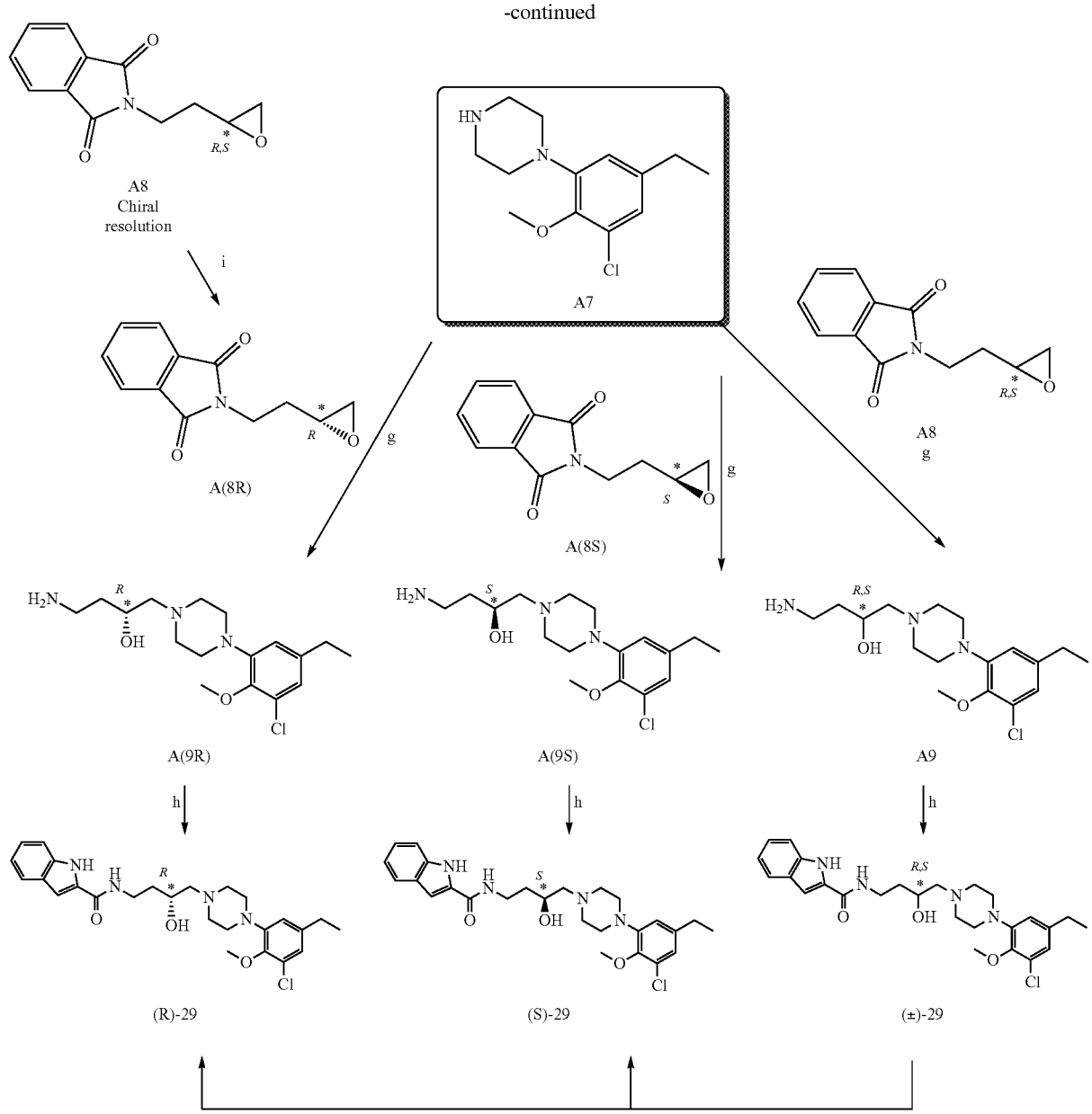

-continued

Chiral Preparative HPLC

Reagents and conditions: (a) fuming HNO₃, 0° C. to room temperature, 2 h; (b) BH₃•CS₂, 12 h; (c) PCC, CH₂Cl₂, overnight; (d) Ph₃P + CH₃Br, Lithium tert-butoxide, THF-78 to 0 then room temperature, 8 h; (e) 10% Pd/C, H₂, 50 psi, EtOAc, 45 mins; (f) bis(2-chloroethyl)amine•HCl, diethyleneglycol monoethylether, 150° C., 7 h; (g) 1) IPA, reflux, 3 h 2) hydrazine, EtOH, reflux, overnight; (h) ArCOOH, EDC/HoBt, DIPEA, DCM/DMF, 0° C. to rt; (i) (Salen)Co(III)(OAc) complex, H₂O, THF, 72 h.

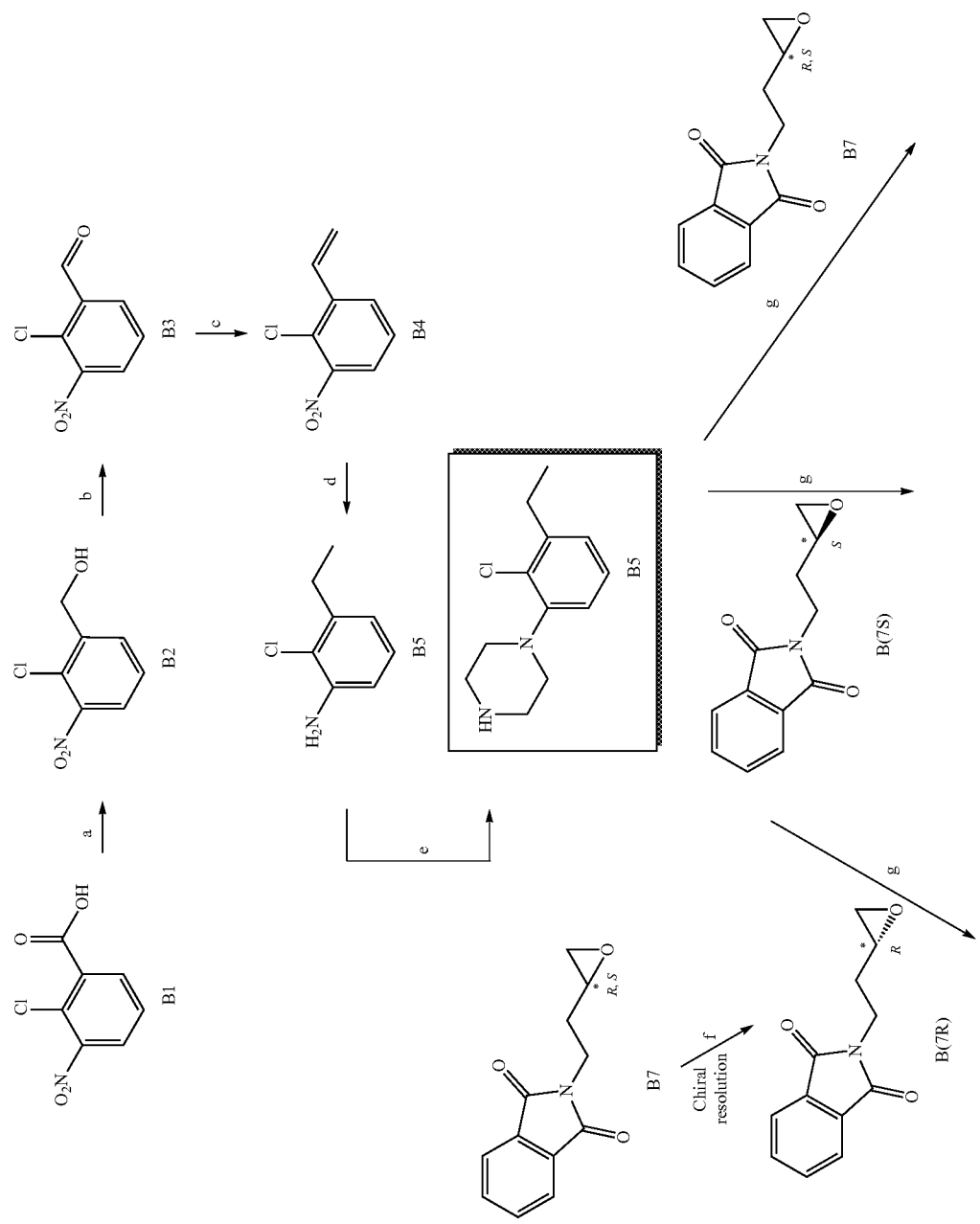

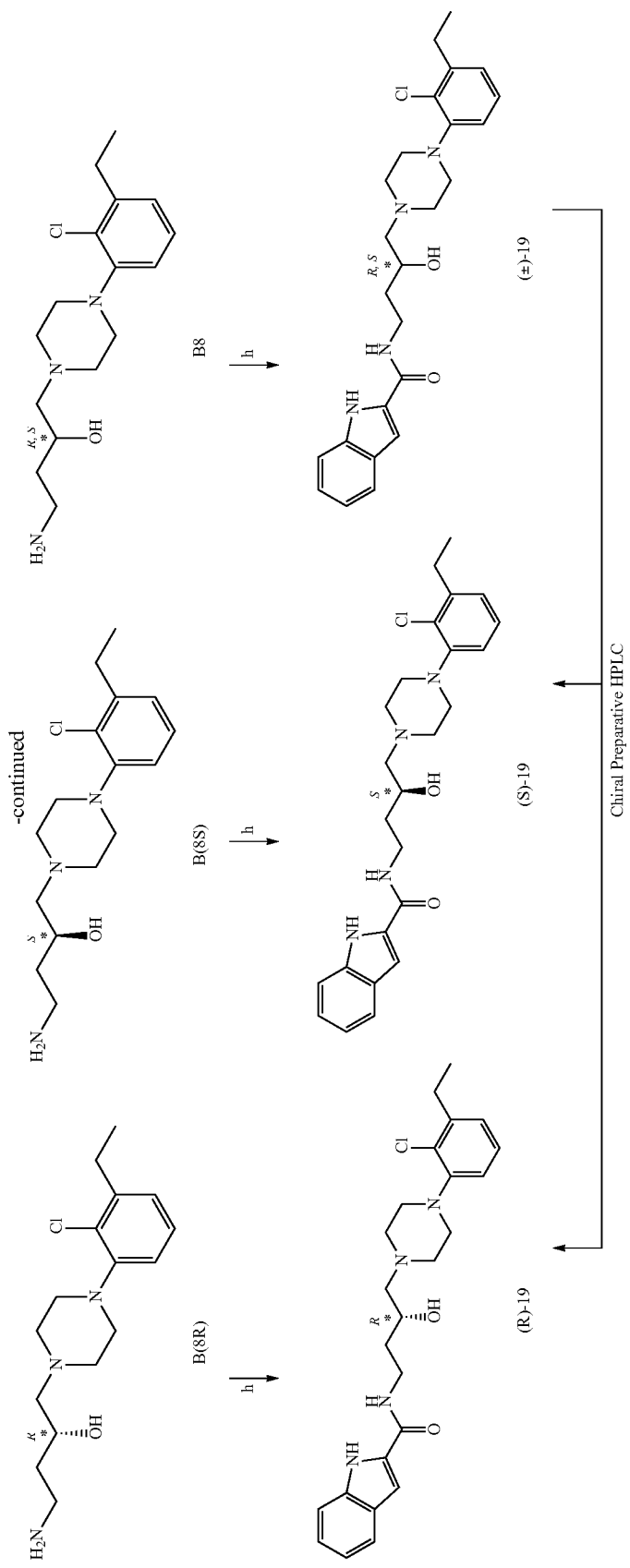

Scheme 3. Synthesis of C4a-b and C5a-b

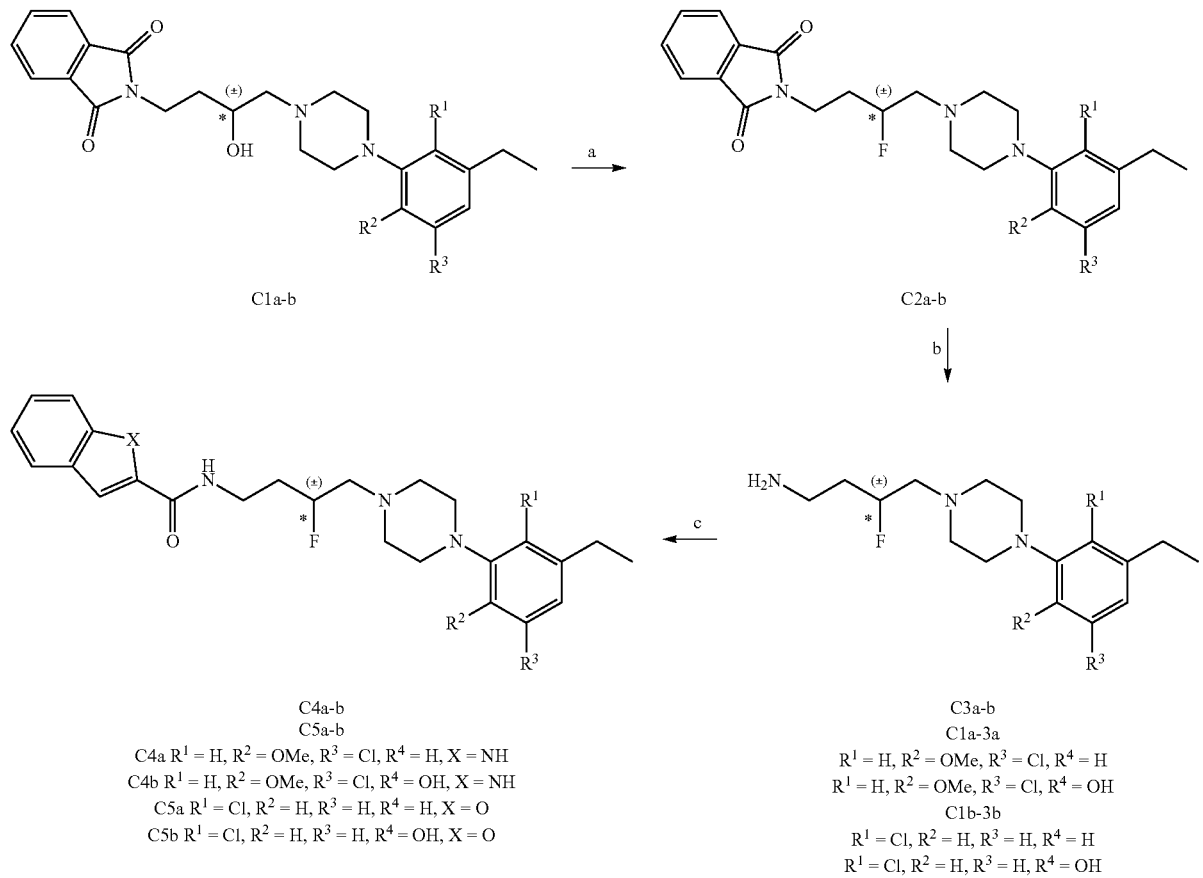

C4a R¹ = H, R² = OMe, R³ = Cl, R⁴ = H, X = NH
C4b R¹ = H, R² = OMe, R³ = Cl, R⁴ = OH, X = NH
C5a R¹ = Cl, R² = H, R³ = H, R⁴ = H, X = O
C5b R¹ = Cl, R² = H, R³ = H, R⁴ = OH, X = O

C1a-3a
R¹ = H, R² = OMe, R³ = Cl, R⁴ = H
R¹ = H, R² = OMe, R³ = Cl, R⁴ = OH
C1b-3b
R¹ = Cl, R² = H, R³ = H, R⁴ = H
R¹ = Cl, R² = H, R³ = H, R⁴ = OH

Reagents and conditions: (a) DAST, Dry, DCM, -78° C., overnight (b) hydrazine EtOH, reflux, overnight; (c) ArCOOH, EDC/Hobt, DIPEA, DCM/DMF, 0° C. to room temperature.

Scheme 4. Synthesis of 35

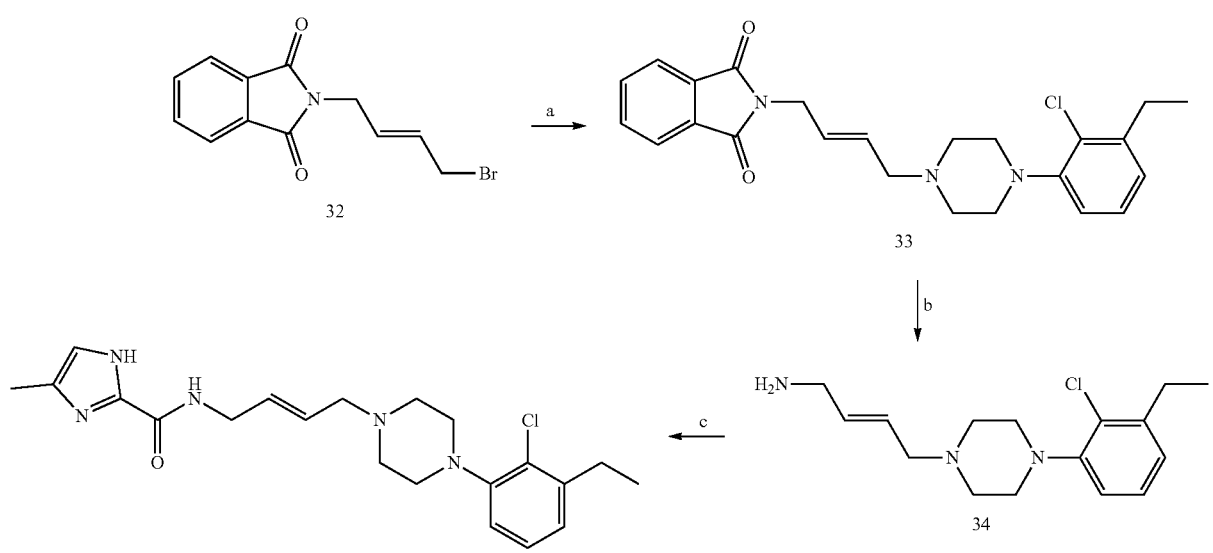

Reagents and conditions: (a) B6, K₂CO₃, acetone, reflux, overnight; (b) hydrazine, EtOH, reflux, overnight; (c) 4-methyl-1H-imidazole-2-carboxylic acid, CDI, THF, 0° C. to RT, overnight.

Scheme 5. Synthesis of 40

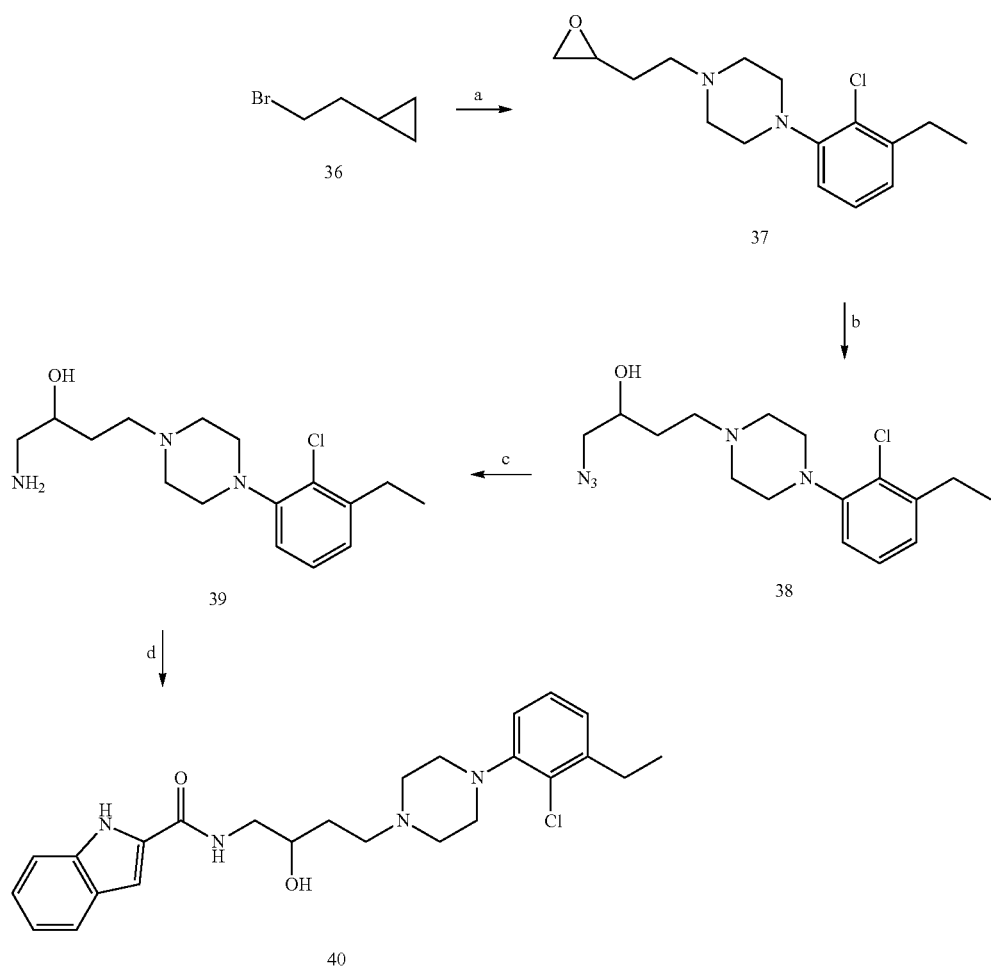

Reagents and conditions: (a) B6, K₂CO₃, acetone, reflux, overnight; (b) NaN₃, NH₄Cl, DMF, 100° C., 6 h; (c) 10% Pd/C, H₂, 50 psi, 2 h; (d) Indole-2-COOH, CDI, THF, 0° C. to RT.

3-Chloro-4-methoxy-5-nitrobenzoic acid (A2): 3-chloro-4-methoxybenzoic acid (5.0 g, 26.79 mmol) was added in small portions to cold fuming $HNO_3$ (90%, 25 mL) at 0-5° C. The reaction mixture was allowed to warm to 20° C. and stirred for an additional 2 h. Cold water (50 mL) was added, and the precipitated product was extracted in $CHCl_3$ and washed with brine solution and concentrated. The product was purified by flash chromatography using 8% MeOH/$CHCl_3$ as eluent to provide 5.28 g (85%) of product. $^1$H NMR (400 MHz, $CD_3OD$) 8.27 (s, 1H), 8.22 (s, 1H), 4.02 (s, 3H); $^{13}$C NMR (100 MHz, $CD_3OD$) δ 165.9, 153.9, 146.4, 136.3, 131.56, 125.9, 63.2; GC-MS (EI) m/z 231 ($M^+$).

(3-Chloro-4-methoxy-5-nitrophenyl)methanol (A3): Borane dimethyl sulfide complex (10 M, 3.072 g, 40.44 mmol) was added dropwise to a solution of A2 (5.28 g, 22.85 mmol) in THF (60 mL) at 0-5° C. The mixture was allowed to come to RT and stirred overnight. The reaction mixture was cooled to 0-5° C. and quenched carefully by dropwise addition of MeOH. The reaction mixture was evaporated to give 4.7 g of crude product and used directly in the next step without further purification. $^1$H NMR (400 MHz, $CDCl_3$) 8.49-8.38 (m, 2H), 5.50 (s, 2H), 4.82 (m, 3H), 3.70 (bs, 1H); $^{13}$C NMR (100 MHz, $CDCl_3$) δ 148.9, 145.2, 137.9, 132.5, 130.6, 121.3, 63.1, 62.5; GC-MS (EI) m/z 217 ($M^+$).

3-Chloro-4-methoxy-5-nitrobenzaldehyde (A4) (Mizuhara et al. Structure-activity relationship study of phenylpyrazole derivatives as a novel class of anti-HIV agents. Bioorg. Med. Chem. Lett. 2013, 23, 4557-61): Pyridinium chlorochromate (PCC, 9.31 g, 43.20 mmol) was added to a solution of A3 (4.7 g, 21.60 mmol) in $CH_2Cl_2$ (100 mL). The reaction mixture was stirred overnight and filtered through a Celite pad. The product was purified by flash chromatography using 20% EtOAc/hexanes as eluent to provide 4.0 g (85%) of the product as a yellow solid. $^1$H NMR (400 MHz, $CDCl_3$) 9.94 (s, 1H), 8.19 (d, J=2.0 Hz, 1H), 8.13 (d, J=2.0 Hz, 1H), 4.10 (s, 3H); $^{13}$C NMR (100 MHz, $CDCl_3$) δ 187.8, 154.4, 145.7, 134.5, 132.2, 131.9, 124.8, 63.0; GC-MS (EI) m/z 215 ($M^+$).

1-Chloro-2-methoxy-3-nitro-5-vinylbenzene (A5): Lithium tert-butoxide (4.46 g, 55.81 mmol) was added dropwise to a suspension of methyltriphenylphosphonium bromide (7.90 g. 22.32 mmol) in dry THF (100 mL) at −78° C. under argon. The reaction mixture was allowed to warm to 0-20° C. and stirred for 3 h and noticed that the formation of yellow precipitate. The solution of A4 (4.0 g, 18.60 mmol) in THF (50 mL) was added dropwise over 30 min. The reaction mixture was maintained at 20° C. and stirred for 8 h. The reaction mixture was quenched with sat. $NH_4Cl$ solution (50 mL) and the THF was removed under vacuum. The crude product was extracted with EtOAc (3×25 mL). The organic layer was combined, dried, concentrated and purified using flash chromatography with 5% Diethyl ether/hexanes as eluent to provide 3.17 g (85%) of the product as a yellow solid. $^1$H NMR (400 MHz, CDCl$_3$) 7.59 (s, 1H), 7.51 (s, 1H), 6.55-6.47 (m, 1H), 5.69 (d, J=16 Hz, 1H), 5.32 (d, J=10.8 Hz, 1H), 3.92 (s, 3H); $^{13}$C NMR (100 MHz, CDCl$_3$) δ 148.7, 145.2, 134.5, 133.1, 131.6, 130.5, 120.8, 117.2, 62.3. GC-MS (EI) m/z 213 (M$^+$).

3-Chloro-5-ethyl-2-methoxyaniline (A6): A mixture of the A5 (3.17 g, 14.8 mmol) and 10% Pd/C (0.350 g) in Ethyl acetate (30 mL) was stirred under an atmosphere of hydrogen (45 psi) at room temperature 45 minutes. The reaction mixture was filtered through a Celite pad and evaporated under vacuum. The reaction mixture was sufficiently pure to be used for the next step without further purification. $^1$H NMR (400 MHz, CDCl$_3$) 6.60 (d, J=2.0 Hz, 1H), 6.44 (d, J=2.0 Hz, 1H), 3.96 (bs, 2H), 3.83 (s, 3H), 2.48 (q, J=7.6 Hz, 2H), 1.19 (t, J=7.6 Hz, 3H); $^{13}$C NMR (100 MHz, CDCl$_3$) δ 141.3, 141.0, 140.9, 127.0, 118.3, 113.7, 59.4, 28.1, 15.2. GC-MS (EI) m/z 185 (M$^+$).

1-(3-Chloro-5-ethyl-2-methoxyphenyl)piperazine (A7): The reaction mixture of A6 (2.8 g, 15.13 mmol) and bis(2-chloroethyl)amine hydrochloride (2.69 g, 15.13 mmol) in diethylene glycol monomethyl ether (4.0 mL) was heated at 150° C. for 7 h under inert atmosphere. The reaction mixture was allowed to come to RT, crushed ice was added and the mixture was neutralized with 2M NaOH to pH 8-9, followed by extraction with ethyl acetate (250 mL). The organic layer was collected, washed twice with ice cold water, concentrated and purified by column chromatography using 5% MeOH/CHCl$_3$ as eluent to provide 2.7 g (70%) of solid product. $^1$H NMR (400 MHz, CDCl$_3$) δ 6.84 (d, J=2 Hz, 1H), 6.61 (d, J=2.4 Hz, 1H), 3.85 (s, 3H), 3.08-3.01 (m, 8H), 2.55 (q, J=8 Hz, 2H), 1.20 (t, J=7.6 Hz, 3H); $^{13}$C NMR (100 MHz, CDCl$_3$) δ 146.8, 146.6, 140.9, 128.4, 122.4, 116.9, 59.2, 51.9, 46.8, 28.6, 15.6. GC-MS (EI) m/z 254.2 (M$^+$). The oxalate salt was precipitated from acetone; Mp 190-191° C. Anal. C$_{13}$H$_{19}$ClN$_2$O.C$_2$H$_2$O$_4$.0.5H$_2$O) C, H, N.

4-amino-1-(4-(3-chloro-5-ethyl-2-methoxyphenyl)piperazin-1-yl)butan-2-ol (A9) 2-(2-(oxiran-2-yl)ethyl)isoindoline-1,3-dione A8 (0.768 g, 3.54 mmol) was added to the reaction mixture of A7 (0.90 g, 3.54 mmol) in 2-propanol (15 mL) and stirred at reflux for 3 h. The formation of 2-(4-(4-(3-chloro-5-ethyl-2-methoxyphenyl)piperazin-1-yl)-3-hydroxybutyl)isoindoline-1,3-dione was confirmed by thin layer chromatography (Kumar et al. *J. Med. Chem.*, 2016, 59 (16), pp 7634-7650.) The reaction mixture was cooled to 20° C. and hydrazine was added and again the reaction mixture was heated to reflux at 90° for 7 h. The reaction was monitored by TLC and when the reaction was complete, the solvent was evaporated and basified with 20% K$_2$CO$_3$ solution (20 mL), followed by extraction with chloroform (250 mL). The combined organic layer was dried over anhydrous Na$_2$SO$_4$ and the solvent was evaporated to afford the product as an oil. $^1$H NMR (400 MHz, CDCl$_3$) δ 6.77 (d, J=2.0 Hz, 1H), 6.55 (d, J=1.6 Hz, 1H), 3.85-3.81 (m, 1H), 3.76 (s, 3H), 3.06 (bs, 4H), 2.86 (m, 2H), 2.72-2.70 (m, 2H), 2.53-2.44 (m, 4H), 2.37-2.28 (m, 3H), 1.53-1.44 (m, 2H), 1.13 (t, J=8.0 Hz, 3H); $^{13}$C NMR (100 MHz, CDCl$_3$) δ 146.3, 146.0, 140.7, 128.1, 122.2, 116.6, 66.2, 64.6, 58.9, 53.8, 50.3, 39.6, 37.7, 28.4, 15.4.

(S)-4-amino-1-(4-(3-chloro-5-ethyl-2-methoxyphenyl)piperazin-1-yl)butan-2-ol (A9S) was prepared by the method described for A9 using (S)-2-(2-(oxiran-2-yl)ethyl)isoindoline-1,3-dione (A8S); $^1$H NMR (400 MHz, CDCl$_3$) δ 6.99 (s, 1H), 6.88 (dd, J=19.1, 8.2 Hz, 2H), 6.61 (s, 1H), 3.97-3.76 (m, 4H), 3.14 (s, 4H), 2.91 (d, J=3.4 Hz, 6H), 2.79 (s, 3H), 2.55 (dt, J=14.5, 7.3 Hz, 6H), 2.47-2.32 (m, 4H), 1.67-1.46 (m, 4H), 1.20 (t, J=7.6 Hz, 4H).

(R)-4-amino-1-(4-(3-chloro-5-ethyl-2-methoxyphenyl)piperazin-1-yl)butan-2-ol (A9R) was prepared by the method described for A9 using (R)-2-(2-(oxiran-2-yl)ethyl)isoindoline-1,3-dione (A8R). The product obtained as such taken for the next step.

General Amidation Procedure A. The carboxylic acid (1.0 mmol) was dissolved in a solution of chloroform and dimethylformamide (8:2) and cooled to 0° C. To this solution was added 1-Ethyl-3-(3-dimethylaminopropyl)carbodiimide (EDCI) (1.3 mmol) and Hydroxybenzotriazole (Hobt) (1.2 mmol). (*Org Biomol Chem.* 2015; 13(40):10162-78). After 30 min, 1 eq of the aryl amine was added at 0° C. To this reaction mixture was added diisopropylethylamine (DIPEA) (1.5 mmol) and the reaction mixture continued stirring at room temperature for 8 h. The reaction progress was monitored by TLC. After completion saturated sodium bicarbonate (NaHCO$_3$) solution was added and the final compounds were extracted from chloroform (50 ml×4). The organic layer obtained was evaporated to afford the crude amide, which were purified using flash column chromatography to provide the desired pure product. All the enantiomers and racemic compounds were characterized by chiral HPLC.

N-(4-(4-(3-chloro-5-ethyl-2-methoxyphenyl)piperazin-1-yl)-3-hydroxybutyl)-1H-indole-2-carboxamide (±)-29 was prepared from indole-2-carboxylic acid and A9 according to the general amidation procedure A. The crude product was purified by flash chromatography using 30% acetone/CHCl$_3$ as eluent to give the desired product in 60.0% yield. $^1$H NMR (400 MHz, CDCl3) δ 9.21 (s, 1H), 7.64 (d, J=8.1 Hz, 1H), 7.42 (t, J=10.3 Hz, 2H), 7.37 (s, 1H), 7.27 (dd, J=11.1, 4.0 Hz, 1H), 7.13 (t, J=7.5 Hz, 1H), 6.85 (d, J=10.7 Hz, 1H), 6.62 (s, 1H), 4.10-3.87 (m, 2H), 3.84 (s, 3H), 3.57-3.39 (m, 1H), 3.16 (s, 3H), 2.84 (s, 2H), 2.55 (dd, J=15.1, 7.6 Hz, 3H), 2.48-2.37 (m, 2H), 1.94-1.74 (m, 1H), 1.72-1.52 (m, 3H), 1.21 (t, J=7.5 Hz, 3H). $^{13}$C NMR (101 MHz, CDCl3) δ 162.89, 162.02, 161.43, 146.41, 145.72, 140.79, 136.06, 131.10, 128.25, 127.76, 124.27, 122.44, 121.72, 120.54, 116.59, 111.86, 101.69, 66.42, 63.67, 58.99, 53.61, 50.30, 38.06, 33.24, 28.40, 15.31; The hydrochloride salt was precipitated from acetone; Anal (C$_{26}$H33ClN$_4$O$_3$.HCl.2H$_2$O) C, H, N.

(S)-N-(4-(4-(3-chloro-5-ethyl-2-methoxyphenyl)piperazin-1-yl)-3-hydroxybutyl)-1H-indole-2-carboxamide ((S)-29) was prepared from indole-2-carboxylic acid and A9S according to the general amidation procedure A. The crude product was purified by flash chromatography using 30% acetone/CHCl$_3$ as eluent to give the desired product in 55% yield. $^1$H NMR (400 MHz, CDCl3) δ 9.42 (s, 1H), 7.64 (d, J=8.0 Hz, 1H), 7.43 (t, J=6.9 Hz, 2H), 7.40 (s, 1H), 7.31-7.22 (m, 1H), 7.13 (t, J=7.5 Hz, 1H), 6.89-6.81 (m, 1H), 6.62 (d, J=1.5 Hz, 1H), 4.02-3.86 (m, 2H), 3.85 (d, J=10.7 Hz, 3H), 3.50 (ddd, J=13.1, 8.3, 3.9 Hz, 1H), 3.15 (s, 3H), 2.84 (d, J=5.3 Hz, 2H), 2.55 (dd, J=15.1, 7.6 Hz, 3H), 2.48-2.34 (m, 2H), 1.91-1.77 (m, 1H), 1.64 (dtd, J=13.8, 8.9, 4.6 Hz, 3H), 1.21 (t, J=7.6 Hz, 3H). $^{13}$C NMR (101 MHz, CDCl3) δ 161.47, 146.41, 145.76, 140.76, 136.16, 131.14, 128.16, 127.61, 124.18, 122.44, 121.84, 120.38, 116.67, 111.77, 101.69, 66.48, 63.74, 58.98, 53.68, 50.39, 37.96, 33.10, 28.46, 28.21, 15.42. The hydrochloride salt was precipitated from acetone; Anal (C$_{26}$H$_{33}$ClN$_4$O$_3$.HCl) C, H, N. [α]$^{23}_D$+ 34.54 (CHCl3, c 0.16) ee >98%.

(R)-N-(4-(4-(3-chloro-5-ethyl-2-methoxyphenyl)piperazin-1-yl)-3-hydroxybutyl)-1H-indole-2-carboxamide ((R)-29) was prepared from indole-2-carboxylic acid and A9R according to the general amidation procedure A. The crude product was purified by flash chromatography using 30% acetone/CHCl$_3$ as eluent to give the desired product in 51% yield. $^1$H NMR (400 MHz, CDCl3) δ 9.33 (s, 1H), 7.64 (d, J=7.9 Hz, 1H), 7.43 (t, J=8.1 Hz, 1H), 7.40 (s, 1H), 7.32-7.22 (m, 1H), 7.13 (t, J=7.6 Hz, 1H), 6.85 (d, J=8.4 Hz, 1H), 6.62 (s, 1H), 3.91 (dd, J=13.1, 6.2 Hz, 2H), 3.84 (s, 3H), 3.58-3.41 (m, 1H), 3.16 (s, 3H), 2.85 (s, 2H), 2.56 (dd, J=15.1, 7.6 Hz, 3H), 2.45 (d, J=6.4 Hz, 2H), 1.82 (s, 1H), 1.64 (d, J=9.2 Hz, 3H), 1.21 (t, J=7.6 Hz, 3H); $^{13}$C NMR (101 MHz, CDCl$_3$) δ 161.52, 146.26, 145.95, 140.77, 136.06, 131.15, 128.30, 127.72, 124.25, 122.33, 121.73, 120.52, 116.67, 111.87, 101.88, 66.43, 63.75, 59.09, 53.69, 50.39, 38.05, 33.26, 28.47; The hydrochloride salt was precipitated from acetone; Anal (C$_{26}$H$_{33}$ClN$_4$O$_3$.HCl.H$_2$O) C, H, N. [α]$^s_D$–27.89 (CHCL3, c 0.23) ee >98%.

2-Chloro-1-nitro-3-vinylbenzene (B4): The same procedure was used as described for A5, starting from B3 (Kumar et al. *J. Med. Chem.*, 2016, 59 (16), pp 7634-7650) to give the desired product in 70% yield. $^1$H NMR (400 MHz, CDCl$_3$) 7.74 (dd, J=8.0, 1.6 Hz, 1H), 7.64 (dd, J=8.0, 1.6 Hz, 1H), 7.37 (t, J=8.0 Hz, 1H), 7.12 (dd, J=17.2, 11.0 Hz, 1H), 5.81 (dd, J=17.2, 0.8 Hz, 1H), 5.54 (dd, J=10.8, 0.8 Hz, 1H); $^{13}$C NMR (100 MHz, CDCl$_3$) δ 149.6, 138.9, 132.1, 129.9, 127.2, 124.8, 123.9, 119.6.

2-Chloro-3-ethylaniline (B5): The same procedure was used as described for A6 using B4 in EtOAc as the solvent. The product was sufficiently pure to be used for the next step without further purification. $^1$H NMR (400 MHz, CDCl$_3$) 6.99 (t, J=7.6 Hz, 1H), 6.66-6.62 (m, 2H), 4.04 (bs, 2H), 2.72 (q, J=7.6 Hz, 2H), 1.22 (t, J=7.6 Hz, 3H); $^{13}$C NMR (100 MHz, CDCl$_3$) δ 143.1, 142.4, 126.9, 119.2, 118.9, 113.4, 27.1, 13.9.

1-(2-Chloro-3-ethylphenyl)piperazine (B6): The same procedure was used as described for A7 starting with B5. The product was purified by flash chromatography using 2% MeOH/CHCl$_3$ as eluent to give the desired product in 46% yield. $^1$H NMR (400 MHz, CDCl$_3$) δ 7.16-7.12 (m, 1H), 6.94-6.89 (m, 2H), 3.05-2.95 (m, 8H), 2.76 (q, J=7.6 Hz, 2H), 1.21 (t, J=7.6 Hz, 3H); $^{13}$C NMR (100 MHz, CDCl$_3$) δ 150.0, 143.2, 128.7, 126.9, 123.9, 118.0, 53.0, 46.3, 27.5, 14.1. The oxalate salt was precipitated from acetone; Mp 166-167° C. Anal. (C$_{12}$H$_{17}$ClN$_2$.1.5C$_2$H$_2$O$_4$.H$_2$O) C, H, N.

4-Amino-1-(4-(2-chloro-3-ethylphenyl)piperazin-1-yl) butan-2-ol (B8): The same procedure was used as described for A9, employing B7 to afford B8 in 90% yield and was sufficiently pure to be used for the next step without further purification. $^1$H NMR (400 MHz, CDCl$_3$) 7.03-7.0 (m, 1H), 6.82-6.77 (m, 2H), 3.80-3.71 (m, 1H), 2.92-2.61 (m, 10H), 2.49-2.24 (m, 7H), 1.46-1.40 (m, 2H), 1.10 (t, J=7.6, 0.8 Hz, 3H); $^{13}$C NMR (100 MHz, CDCl$_3$) δ 149.2, 142.8, 128.3, 126.6, 123.6, 117.7, 65.8, 64.4, 51.3, 39.3, 37.5, 27.1, 13.8.

(S)-4-amino-1-(4-(2-chloro-3-ethylphenyl)piperazin-1-yl)butan-2-ol (B8S) was prepared by the method described for B8 using (S)-2-(2-(oxiran-2-yl)ethyl)isoindoline-1,3-dione B7S.

(R)-4-amino-1-(4-(2-chloro-3-ethylphenyl)piperazin-1-yl)butan-2-ol (B8R) was prepared by the method described for A9 using (R)-2-(2-(oxiran-2-yl)ethyl)isoindoline-1,3-dione B7R.

N-(4-(4-(2-chloro-3-ethylphenyl)piperazin-1-yl)-3-hydroxybutyl)-1H-indole-2-carboxamide (±)-19 was prepared from indole-2-carboxylic acid and B8 according to the general amidation procedure A. The crude product was purified by flash chromatography using 30% acetone/CHCl$_3$ as eluent to give the desired product in 60% yield. $^1$H NMR (400 MHz, CDCl$_3$) δ 9.20 (s, 1H), 7.64 (d, J=7.8 Hz, 2H), 7.43 (d, J=8.2 Hz, 1H), 7.40 (s, 1H), 7.31-7.23 (m, 1H), 7.20-7.09 (m, 1H), 7.00-6.88 (m, 2H), 6.84 (d, J=1.4 Hz, 1H), 3.91 (ddd, J=13.5, 10.7, 5.2 Hz, 3H), 3.57-3.41 (m, 1H), 3.07 (s, 3H), 2.88 (d, J=5.4 Hz, 2H), 2.78 (q, J=7.5 Hz, 2H), 2.61 (s, 2H), 2.51-2.39 (m, 2H), 1.89-1.76 (m, 1H), 1.64 (ddd, J=18.9, 9.1, 4.4 Hz, 1H), 1.22 (q, J=7.5 Hz, 3H). $^{13}$C NMR (101 MHz, CDCl$_3$) δ 161.36, 149.36, 143.15, 136.05, 131.04, 128.50, 127.81, 126.90, 124.19, 124.14, 121.76, 120.53, 117.96, 111.76, 101.73, 66.52, 63.62, 51.65, 51.34, 38.00, 33.11, 27.46, 27.32, 14.07. The hydrochloride salt was precipitated from acetone; Anal (C$_{25}$H$_{31}$ClN$_4$O$_2$.HCl.H$_2$O) C, H, N.

(R)-N-(4-(4-(2-chloro-3-ethylphenyl)piperazin-1-yl)-3-hydroxybutyl)-1H-indole-2-carboxamide (R)-19 was prepared from indole-2-carboxylic acid and 8R according to the general amidation procedure A. The crude product was purified by flash chromatography using 30% acetone/CHCl$_3$ as eluent to give the desired product in 50% yield. $^1$H NMR (400 MHz, CDCl$_3$) δ 9.44 (s, 1H), 7.64 (d, J=7.7 Hz, 2H), 7.44 (d, J=7.9 Hz, 1H), 7.33-7.21 (m, 1H), 7.15 (dt, J=14.9, 7.5 Hz, 1H), 6.95 (dd, J=17.8, 7.6 Hz, 2H), 6.85 (s, 2H), 4.01-3.82 (m, 3H), 3.51 (s, 1H), 3.07 (s, 3H), 2.89 (s, 2H), 2.78 (dd, J=14.8, 7.3 Hz, 2H), 2.63 (s, 2H), 2.52-2.40 (m, 2H), 1.83 (s, 1H), 1.64 (d, J=9.4 Hz, 1H), 1.23 (t, J=7.4 Hz, 3H). $^{13}$C NMR (101 MHz, CDCl3) δ 161.54, 149.26, 143.23, 136.18, 131.14, 128.72, 127.64, 126.78, 124.22, 121.70, 120.49, 117.97, 111.85, 101.83, 66.45, 63.70, 51.63, 38.09, 33.26, 27.46, 14.02. The hydrochloride salt was precipitated from acetone; Anal (C$_{25}$H$_{31}$ClN$_4$O$_2$.HCl.H$_2$O) C, H, N. [α]$^{23}_D$–45.29 (CHCl3, c 0.23), ee >98%.

(S)-N-(4-(4-(2-chloro-3-ethylphenyl)piperazin-1-yl)-3-hydroxybutyl)-1H-indole-2-carboxamide (S)-19 was prepared from indole-2-carboxylic acid and B8S according to the general amidation procedure A. The crude product was purified by flash chromatography using 30% acetone/CHCl$_3$ as eluent to give the desired product in 55% yield. $^1$H NMR (400 MHz, CDCl$_3$) δ 9.52 (s, 1H), 7.64 (d, J=7.8 Hz, 1H), 7.45 (dd, J=8.3, 0.7 Hz, 2H), 7.33-7.21 (m, 1H), 7.14 (dt, J=7.9, 4.3 Hz, 1H), 6.95 (ddd, J=18.5, 7.8, 1.4 Hz, 2H), 6.86 (d, J=1.3 Hz, 2H), 4.07-3.82 (m, 3H), 3.51 (ddd, J=13.2, 8.4, 4.1 Hz, 1H), 3.07 (s, 3H), 2.89 (dd, J=10.6, 5.0 Hz, 2H), 2.78 (q, J=7.5 Hz, 2H), 2.62 (d, J=7.8 Hz, 2H), 2.51-2.38 (m, 2H), 1.84 (ddd, J=13.5, 5.6, 3.3 Hz, 1H), 1.73-1.55 (m, 1H), 1.24 (dd, J=12.8, 5.3 Hz, 3H). $^{13}$C NMR (101 MHz, CDCl3) δ 161.56, 149.36, 143.16, 136.20, 131.02, 128.66, 127.76, 126.90, 124.20, 121.92, 120.48, 117.97, 111.92, 101.82, 66.40, 63.70, 51.64, 38.11, 33.17, 27.47, 14.08. The hydrochloride salt was precipitated from acetone; Anal (C$_{25}$H$_{31}$ClN$_4$O$_2$.HCl.H$_2$O) C, H, N. [α]$^{23}$L+48.13 (CHCl3, c 0.25) ee >98%

2-(4-(4-(3-Chloro-5-ethyl-2-methoxyphenyl)piperazin-1-yl)butyl)isoindoline-1,3-dione (14a): N-(4-Bromobutyl) phthalimide (0.378 g, 1.34 mmol) was added to a reaction mixture of A7 (0.310 g, 1.22 mmol) and K$_2$CO$_3$ (0.505 g, 3.65 mmol) in acetone (15 mL) and stirred at reflux overnight. The crude product was filtered, concentrated and purified by flash chromatography using 12% EtOAc/hexanes as eluent to provide 0.465 g (83.6%) of the product as oil. $^1$H NMR (400 MHz, CDCl$_3$) δ 7.68 (dd, J=5.6, 2.8 Hz, 2H), 7.57 (dd, J=5.6, 3.2 Hz, 2H), 6.68 (d, J=2.4 Hz, 1H), 6.49 (d, J=2.0 Hz, 1H), 3.69 (s, 3H), 3.60 (t, J=7.0 Hz, 2H), 3.01 (bs, 4H), 2.48 (bs, 4H), 2.40 (q, J=7.6 Hz, 2H), 2.32 (t, J=7.0 Hz, 2H), 1.62 (quintet, J=7.6 Hz, 2H), 1.48-1.45 (m, 2H), 1.06 (t, J=7.6 Hz, 3H); $^{13}$C NMR (100 MHz, CDCl$_3$) δ 168.2, 146.3, 146.0, 140.6, 133.8, 132.0, 128.0, 123.0, 122.0, 116.6, 58.8, 57.9, 53.6, 50.0, 37.7, 28.3, 26.5, 23.9, 15.3.

2-(4-(4-(2-Chloro-3-ethylphenyl)piperazin-1-yl)butyl) isoindoline-1,3-dione (14b): The same procedure was used as described for 14a, employing B6. The product was purified by flash chromatography using 20% EtOAc/hexanes as eluent to afford 14b in 64.2% yield. $^1$H NMR (400 MHz, CDCl$_3$) 7.85-7.82 (m, 2H), 7.71-7.69 (m, 2H), 7.15 (dt, J=7.6, 2.4 Hz, 1H), 6.95-6.91 (m, 2H), 3.75 (dt, J=6.4, 0.8 Hz, 2H), 3.06 (bs, 4H), 2.77 (dq, J=7.6, 2.0 Hz, 2H), 2.64 (bs, 4H), 2.47 (t, J=6.8 Hz, 2H), 1.80-1.75 (m, 2H), 1.63-1.59 (m, 2H), 1.27-1.21 (m, 3H); $^{13}$C NMR (100 MHz, CDCl$_3$) δ 167.9, 149.4, 142.8, 133.6, 131.9, 128.4, 126.6, 123.6, 122.8, 117.7, 57.8, 53.2, 51.3, 37.6, 27.2, 26.4, 24.0, 13.9.

4-(4-(3-Chloro-5-ethyl-2-methoxyphenyl)piperazin-1-yl) butan-1-amine (16a): Hydrazine (0.097 g, 3.02 mmol) was added to a solution of compound 14a (0.460 g, 1.00 mmol) in EtOH (15 mL) and stirred at reflux for 7 h. The solvent was evaporated and the reaction mixture was diluted with 20% aq. K$_2$CO$_3$ solution (15 mL) and extracted in CHCl$_3$ (2×15 mL). The organic layer was combined, dried and concentrated to afford yellow oily product, which was sufficiently pure to be used for the next step without further purification. $^1$H NMR (400 MHz, CDCl$_3$) δ 6.70 (d, J=2.0 Hz, 1H), 6.49 (d, J=2.0 Hz, 1H), 3.70 (s, 3H), 3.01 (bs, 4H), 2.59 (s, 2H), 2.47-2.38 (m, 6H), 2.27 (t, J=7.6 Hz, 2H), 1.46-1.33 (m, 4H), 1.07 (t, J=7.6 Hz, 3H); $^{13}$C NMR (100 MHz, CDCl$_3$) δ 146.3, 146.1, 140.6, 128.0, 122.0, 116.5, 58.8, 58.5, 53.7, 50.2, 28.3, 24.2, 15.3.

4-(4-(2-Chloro-3-ethylphenyl)piperazin-1-yl)butan-1-amine (16b): The same procedure was used as described for 16a, employing 14b to afford 16b in 85.1% yield and was sufficiently pure to be used for the next step without further purification. $^1$H NMR (400 MHz, CDCl$_3$) 6.99-6.95 (m, 1H), 6.77-6.74 (m, 2H), 2.89 (bs, 4H), 2.63-2.54 (m, 4H), 2.47 (bs, 4H), 2.27-2.23 (m, 2H), 1.43-1.28 (m, 4H), 1.08-1.04 (m, 5H); $^{13}$C NMR (100 MHz, CDCl$_3$) δ 149.3, 142.7, 128.3, 126.5, 123.5, 117.6, 58.2, 53.1, 51.2, 41.8, 31.5, 27.1, 24.0, 13.8.

General Amidation Procedure B. CDI (1 equiv) was added to a solution of the carboxylic acid (1 equiv) in dry THF (10 mL/mmol) and stirred for 3 h at RT. The reaction mixture was cooled to 0° C. and particular amine (1 equiv) was added dropwise after diluting with dry THF (10 mL/mmol). The reaction mixture was allowed to come to RT and stirred overnight, concentrated, diluted with H$_2$O (20 mL) and extracted in CHCl$_3$ (3×10 mL). The organic layer was concentrated and the product was purified by flash column chromatography to provide the respective amide.

N-(4-(4-(2-Chloro-3-ethylphenyl)piperazin-1-yl)butyl)-1H-indole-2-carboxamide (18): 18 was prepared from indole-2-carboxylic acid and 16b according to the general amidation procedure B. The crude product was purified by flash chromatography using 30% acetone/CHCl$_3$ as eluent to give the desired product in 51.0% yield. $^1$H NMR (400 MHz, CDCl$_3$) 10.35 (s, 1H), 7.63 (d, J=7.6 Hz, 1H), 7.47 (d, J=8.8 Hz, 1H), 7.27 (dt, J=8.0, 1.2 Hz, 1H), 7.13 (sextet, J=4.0 Hz, 2H), 6.96-6.87 (m, 4H), 3.56 (dd, J=12.8, 6.4 Hz, 2H), 3.06 (bs, 4H), 2.78 (q, J=7.6 Hz, 2H), 2.65 (bs, 4H), 2.47 (t, J=7.2 Hz, 2H), 1.72-1.64 (m, 4H), 1.23 (t, J=7.6 Hz, 3H); $^{13}$C NMR (100 MHz, CDCl$_3$) δ 162.1, 149.6, 143.3, 136.7, 131.1, 128.7, 127.6, 127.0, 124.3, 124.1, 121.9, 120.6, 118.1, 112.2, 102.2, 58.1 53.5, 51.5, 39.8, 27.7, 27.6, 24.5, 14.2. The oxalate salt was precipitated from acetone; Mp 228-229° C. Anal (C$_{25}$H$_{31}$ClN$_4$O.C$_2$H$_2$O$_4$.0.75H$_2$O) C, H, N.

N-(4-(4-(2-Chloro-3-ethylphenyl)piperazin-1-yl)butyl) benzofuran-2-carboxamide (20): 20 was prepared from benzofuran-2-carboxylic acid and 16b according to the general amidation procedure B. The crude product was purified by flash chromatography using 25% EtOAc/hexanes as eluent to give the desired product in 76.5% yield. $^1$H NMR (400 MHz, CDCl$_3$) 7.65-7.63 (m, 1H), 7.46 (bs, 1H), 7.44 (d, J=0.8 Hz, 1H), 7.38 (dt, J=7.2, 1.2 Hz, 1H), 7.29-7.25 (m, 1H), 7.15-7.11 (m, 2H), 6.91 (dq, J=7.2, 1.6 Hz, 2H), 3.53 (dd, J=12.4, 6.4 Hz, 2H), 3.08 (bs, 4H), 2.77 (q, J=7.6 Hz, 2H), 2.67 (bs, 4H), 2.48 (t, J=7.0 Hz, 2H), 1.74-1.65 (m, 4H), 1.22 (t, J=7.6 Hz, 3H); $^{13}$C NMR (100 MHz, CDCl$_3$) δ 158.9, 154.7, 149.6, 149.0, 143.2, 128.7, 127.7, 126.9, 126.8, 124.0, 123.7, 122.7, 118.0, 111.7, 110.2, 58.0, 53.5, 51.5, 39.2, 27.6, 27.5, 24.4, 14.1. The oxalate salt was precipitated from acetone; Mp 119-120° C. Anal (C$_{25}$H$_{30}$ClN$_3$O$_2$.C$_2$H$_2$O$_4$.0.5H$_2$O) C, H, N.

N-(4-(4-(2-Chloro-3-ethylphenyl)piperazin-1-yl)-3-hydroxybutyl)benzofuran-2-carboxamide (21): 21 was prepared from benzofuran-2-carboxylic acid and B8 according to the general amidation procedure B. The crude product was purified by flash chromatography using 25% acetone/CHCl$_3$ as eluent to give the desired product in 52.1% yield. $^1$H NMR (400 MHz, CDCl$_3$) 7.64 (d, J=7.2 Hz, 1H), 7.58 (t, J=5.0 Hz, 1H), 7.50-7.45 (m, 2H), 7.38 (dt, J=7.2, 1.2 Hz, 1H), 7.28-7.24 (m, 1H), 7.15 (t, J=7.6 Hz, 1H), 6.92 (dq, J=8.0, 1.2 Hz, 2H), 3.94-3.84 (m, 3H), 3.55-3.50 (m, 1H), 3.06 (bs, 4H), 2.87-2.85 (m, 2H), 2.76 (q, J=7.6 Hz, 2H), 2.62-2.61 (m, 2H), 2.48-02.43 (m, 2H), 1.85-1.80 (m, 1H), 1.66-1.63 (m, 1H), 1.22 (t, J=7.6 Hz, 3H); $^{13}$C NMR (100 MHz, CDCl$_3$) δ 159.0, 154.8, 149.4, 149.1, 143.3, 128.7, 127.7, 127.0, 126.7, 124.2, 123.6, 122.7, 118.0, 111.9, 110.1, 66.0, 63.9, 51.7, 37.5, 33.7, 27.5, 14.2. The oxalate salt was precipitated from ether; Mp 147-148° C. Anal (C$_{25}$H$_{30}$ClN$_3$O$_3$. C$_2$H$_2$O$_4$.H$_2$O) C, H, N.

N-(4-(4-(2-chloro-3-ethylphenyl)piperazin-1-yl)butyl) imidazo[1,2-a]pyridine-2-carboxamide (22): 22 was prepared from imidazo[1,2-a]pyridine-2-carboxylic acid and 16b according to the general amidation procedure B. The crude product was purified by flash chromatography using 3% MeOH/CHCl$_3$ as eluent to give the desired product in 78.4% yield. $^1$H NMR (400 MHz, CDCl$_3$) δ 8.11-8.09 (m, 2H), 7.53-7.49 (m, 2H), 7.21-7.17 (m, 1H), 7.10 (t, J=8.0 Hz, 1H), 6.89 (t, J=7.2 Hz, 2H), 6.81-6.77 (m, 1H), 3.48 (q, J=6.0 Hz, 2H), 3.03 (bs, 4H), 7.72 (q, J=7.6 Hz, 2H), 2.62 (m, 4H), 2.45-2.42 (m, 2H), 1.65 (m, 4H), 1.18 (t, J=7.6 Hz, 3H); $^{13}$C NMR (100 MHz, CDCl$_3$) δ 162.7, 149.6, 144.4, 143.1, 140.0, 128.6, 126.9, 126.5, 126.0, 123.9, 118.0, 114.1, 113.3, 58.1, 53.4, 51.4, 39.0, 27.7, 27.4, 24.3, 14.1. The oxalate salt was precipitated from acetone; Mp 144-145° C. Anal (C$_{24}$H$_{30}$ClN$_5$O.2C$_2$H$_2$O$_4$.1.5H$_2$O) C, H, N.

N-(4-(4-(2-Chloro-3-ethylphenyl)piperazin-1-yl)-3-hydroxybutyl)imidazo[1,2-a]pyridine-2-carboxamide (23): 23 was prepared from imidazo[1,2-a]pyridine-2-carboxylic acid and B8 according to the general amidation procedure B. The crude product was purified by flash chromatography using 2% MeOH/CHCl$_3$ as eluent to give the desired product in 46.3% yield. $^1$H NMR (400 MHz, CDCl$_3$) δ 8.13-8.11 (m, 2H), 7.90 (bt, J=6.0 Hz, 1H), 7.56 (dd, J=7.2, 0.8 Hz, 1H), 7.23-7.19 (m, 1H), 7.14 (t, J=8.0 Hz, 1H), 6.93 (dq, J=7.6, 1.6 Hz, 2H), 6.82 (dt, J=6.4, 1.2 Hz, 1H), 3.91-3.78 (m, 2H), 3.56-3.48 (m, 1H), 3.04 (bs, 4H), 2.86-2.83 (m, 2H), 2.75 (q, J=7.6 Hz, 2H), 2.62-2.60 (m, 2H), 2.45-2.40 (m, 2H), 1.84-1.76 (m, 1H), 1.70-1.61 (m, 1H), 1.21 (t, J=7.6 Hz, 3H); $^{13}$C NMR (100 MHz, CDCl$_3$) δ 162.9, 149.5, 144.6, 143.2, 140.2, 128.7, 126.9, 126.4, 125.8, 124.0, 118.2, 118.0, 114.1, 113.3, 65.3, 63.9, 53.5, 51.6, 36.6, 34.4, 27.4, 14.1. The oxalate salt was precipitated from acetone; Mp 137-138° C. Anal (C$_{24}$H$_{30}$ClN$_5$O$_2$.2C$_2$H$_2$O$_4$.H$_2$O.0.75CHCl$_3$) C, H, N.

N-(4-(4-(2-chloro-3-ethylphenyl)piperazin-1-yl)butyl)-6-methylimidazo[2,1-b]thiazole-5-carboxamide (24): 24 was prepared from 6-methylimidazo[2,1-b]thiazole-5-carboxylic acid and 16b according to the general amidation procedure B. The crude product was purified by flash chromatography using 3% MeOH/CHCl$_3$ as eluent to give the desired product in 48.9% yield. $^1$H NMR (400 MHz, CDCl$_3$) δ 8.19 (d, J=4.0 Hz, 1H), 7.13-7.09 (m, 1H), 6.92-6.82 (m, 3H), 5.98 (m, 1H), 3.50-3.45 (m, 2H), 3.03 (bs, 4H), 2.73 (q, J=7.6 Hz, 2H), 2.64 (bs, 4H), 2.58 (s, 3H), 2.48-2.45 (m, 2H), 1.66 (m, 4H), 1.19 (t, J=8.0 Hz, 3H); $^{13}$C NMR (100 MHz, CDCl$_3$) δ 160.7, 150.9, 149.4, 145.1, 143.2, 128.7, 126.9, 124.0, 121.4, 118.7, 117.9, 112.4, 58.1, 53.4, 51.3, 39.4, 27.9, 27.4, 24.2, 16.5, 14.1. The oxalate salt was precipitated from acetone; Mp 113-114° C. Anal (C$_{23}$H$_{30}$ClN$_5$OS.2C$_2$H$_2$O$_4$.2.5H$_2$O) C, H, N.

N-(4-(4-(2-Chloro-3-ethylphenyl)piperazin-1-yl)butyl)-4-ethyl-1H-imidazole-2-carboxamide (25): A solution of trimethylaluminium (2M in hexane) (0.18 mL, 3.54 mmol) was added dropwise to a solution of 16b (0.105 g, 3.54 mmol) in CH$_2$Cl$_2$ (10 mL) under argon at RT. The reaction mixture was stirred at RT for 15 min and ethyl 4-ethyl-1H-imidazole-2-carboxylate solution in CH$_2$Cl$_2$ (10 mL) was added dropwise and stirred for 6 h. The reaction mixture was quenched with dil. HCl solution (15 mL). The organic layer was extracted, dried over Na$_2$SO$_4$, concentrated and purified using flash chromatography with 4% MeOH/CHCl$_3$ as eluent to provide 0.148 g (14.9%) of product. $^1$H NMR (400 MHz, CDCl$_3$) δ 7.56 (bs, 1H), 7.13 (t, J=7.6 Hz, 1H), 6.92 (t, J=8.0 Hz, 2H), 6.82 (s, 1H), 3.46-3.43 (m, 2H), 3.06 (s, 4H), 2.75 (q, J=7.6 Hz, 2H), 2.66 (m, 5H), 2.48-2.46 (m, 2H), 2.18-2.15 (m, 1H), 1.65 (s, 5H), 1.29-1.18 (m, 6H); $^{13}$C NMR (100 MHz, CDCl$_3$) δ 159.1, 149.5, 143.2, 140.0, 128.7, 126.9, 124.0, 118.0, 58.0, 53.4, 51.2, 39.1, 27.5, 27.4, 24.1, 14.1, 13.5. The oxalate salt was precipitated from acetone; Mp 167-168° C. Anal (C$_{22}$H$_{32}$ClN$_5$O.2.5C$_2$H$_2$O$_4$.H$_2$O) C, H, N.

N-(4-(4-(2-Chloro-3-ethylphenyl)piperazin-1-yl)butyl)-4-methyl-1H-imidazole-2-carboxamide (26): 26 was prepared from 4-methyl-1H-imidazole-2-carboxylic acid and 16b according to the general amidation procedure B. The crude product was purified by flash chromatography using 3% MeOH/CHCl$_3$ as eluent to give the desired product in 65.2% yield. $^1$H NMR (400 MHz, CDCl$_3$) δ 7.76 (bs, 1H), 7.13 (t, J=8.0 Hz, 1H), 6.94-6.89 (m, 2H), 6.82 (s, 1H), 3.46 (q, J=6.4 Hz, 2H), 3.06 (bs, 4H), 2.75 (q, J=8.0 Hz, 2H), 2.64 (bs, 4H), 2.45 (t, J=7.2 Hz, 2H), 2.28 (s, 3H), 1.68-1.61 (m, 4H), 1.20 (t, J=7.6 Hz, 3H); $^{13}$C NMR (100 MHz, CDCl$_3$) δ 159.3, 149.5, 143.2, 140.1, 128.6, 126.9, 124.0, 118.0, 58.1, 53.4, 51.4, 39.2, 27.5, 24.2, 14.1. The oxalate salt was precipitated from acetone; Mp 175-176° C. Anal (C$_{21}$H$_{30}$ClN$_5$O.2C$_2$H$_2$O$_4$.H$_2$O) C, H, N.

N-(4-(4-(2-Chloro-3-ethylphenyl)piperazin-1-yl)-3-hydroxybutyl)-4-methyl-1H-imidazole-2-carboxamide (27): 27 was prepared from 4-methyl-1H-imidazole-2-carboxylic acid and B8 according to the general amidation procedure B. The crude product was purified by flash chromatography using 3% MeOH/CHCl$_3$ as eluent to give the desired product in 39.8% yield. $^1$H NMR (400 MHz, CDCl$_3$) δ 12.40 (bs, 1H), 8.11 (bs, 1H), 8.01 (s, 1H), 7.14 (t, J=8.0 Hz, 1H), 6.95-6.88 (m, 2H), 6.83 (bs, 1H), 3.90-3.84 (m, 1H), 3.79-3.70 (m, 1H), 3.57-3.49 (m, 1H), 3.03 (bs, 4H), 2.83-2.81 (m, 2H), 2.75 (q, J=8.0 Hz, 2H), 2.58 (bs, 2H), 2.42 (d, J=6.6 Hz, 2H), 2.29 (bs, 3H), 1.81-1.73 (m, 1H), 1.68-1.59 (m, 1H), 1.20 (t, J=8.0 Hz, 3H); $^{13}$C NMR (100 MHz, CDCl$_3$) δ 162.6, 159.3, 149.4, 143.2, 140.0, 128.6, 126.9, 124.1, 118.0, 65.0, 63.9, 53.5, 51.6, 36.8, 34.1, 27.5, 14.1. The oxalate salt was precipitated from acetone; Mp 130-131° C. Anal (C$_{21}$H$_{30}$ClN$_5$O$_2$.2C$_2$H$_2$O$_4$.3H$_2$O) C, H, N.

N-(4-(4-(3-Chloro-5-ethyl-2-methoxyphenyl)piperazin-1-yl)butyl)-1H-indole-2-carboxamide (28): 28 was prepared from indole-2-carboxylic acid and 16a according to the general amidation procedure B. The crude product was purified by flash chromatography using 25% acetone/CHCl$_3$ as eluent to give the desired product in 57.6% yield. $^1$H NMR (400 MHz, CDCl$_3$) δ 10.25 (s, 1H), 7.62 (d, J=8.0 Hz, 1H), 7.45 (dd, J=8.0, 0.8 Hz, 1H), 7.28-7.24 (m, 1H), 7.14-7.10 (m, 1H), 6.93 (m, 1H), 6.90 (s, 1H), 6.84 (d, J=1.6 Hz, 1H), 6.58 (d, J=1.6 Hz, 1H), 3.83 (s, 3H), 3.54 (q, J=6.0 Hz, 2H), 3.14 (bs, 4H), 2.60 (bs, 4H), 2.53 (q, J=7.6 Hz, 2H), 2.45 (d, J=7.0 Hz, 2H), 1.73-1.64 (m, 4H), 1.19 (t, J=7.6 Hz, 3H); $^{13}$C NMR (100 MHz, CDCl$_3$) δ 162.0, 146.4, 146.0, 140.9, 136.6, 131.0, 128.2, 127.6, 124.3, 122.3, 121.8, 120.5, 116.7, 112.1, 102.3, 59.0, 58.0, 53.7, 50.1, 39.6, 28.4, 27.5, 24.2, 15.4. The oxalate salt was precipitated from acetone and crystallized in MeOH/ether; Mp 220-221° C. Anal (C$_{26}$H$_{33}$ClN$_4$O$_2$.C$_2$H$_2$O$_4$.0.5H$_2$O) C, H, N.

N-(4-(4-(3-Chloro-5-ethyl-2-methoxyphenyl)piperazin-1-yl)butyl)benzofuran-2-carboxamide (30): 30 was prepared from benzofuran-2-carboxylic acid and 16a according to the general amidation procedure. The crude product was purified by flash chromatography using 20% acetone/CHCl$_3$ as eluent to give the desired product in 76.5% yield. $^1$H NMR (400 MHz, CDCl$_3$) δ 7.63 (dd, J=7.2, 1.2 Hz, 1H), 7.44-7.42 (m, 2H), 7.36 (dt, J=7.0, 1.2 Hz, 1H), 7.28-7.24 (m, 1H), 7.13 (m, 1H), 6.82 (d, J=2.0 Hz, 1H), 6.59 (d, J=2.0 Hz, 1H), 3.82 (s, 3H), 3.51 (q, J=6.4 Hz, 2H), 3.15 (bs, 4H), 2.61 (bs, 4H), 2.51 (q, J=7.6 Hz, 2H), 2.45 (t, J=7.0 Hz, 2H), 1.73-1.63 (m, 4H), 1.17 (t, J=7.6 Hz, 3H); $^{13}$C NMR (100 MHz, CDCl$_3$) δ 158.9, 154.7, 149.0, 146.4, 146.1, 140.8, 128.2, 127.7, 126.7, 123.7, 122.7, 122.2, 116.7, 111.6, 110.2, 59.0, 58.0, 53.8, 50.2, 39.2, 28.4, 27.5, 24.3, 15.4. The oxalate salt was precipitated from acetone and crystallized in MeOH/ether; Mp 126-127° C. Anal (C$_{26}$H$_{32}$ClN$_3$O$_3$.2C$_2$H$_2$O$_4$.H$_2$O) C, H, N.

N-(4-(4-(3-Chloro-5-ethyl-2-methoxyphenyl)piperazin-1-yl)-3-hydroxybutyl)benzofuran-2-carboxamide (31): 31 was prepared from benzofuran-2-carboxylic acid and A9 according to the general amidation procedure. The crude product was purified by flash chromatography using 20% acetone/CHCl$_3$ as eluent to give the desired product in 50.5% yield. $^1$H NMR (400 MHz, CDCl$_3$) δ 7.64 (dd, J=7.6, 0.8 Hz, 1H), 7.53 (m, 1H), 7.49 (dd, J=8.4. 0.8 Hz, 1H), 7.44 (d, J=0.8 Hz, 1H), 7.40-7.36 (m, 1H), 7.29-7.25 (m, 1H), 6.85 (d, J=2.0 Hz, 1H), 6.61 (d, J=2.0 Hz, 1H), 3.95-3.81 (m, 5H), 3.56-3.48 (m, 1H), 3.14 (bs, 4H), 2.84-2.81 (m, 2H), 2.62-2.51 (m, 4H), 2.46-2.42 (m, 2H), 1.87-1.80 (m, 1H), 1.68-1.61 (m, 1H), 1.20 (t, J=7.6 Hz, 3H); $^{13}$C NMR (100 MHz, CDCl$_3$) δ 159.0, 154.8, 149.0, 146.4, 146.0, 140.8, 128.3, 127.7, 126.7, 123.6, 122.6, 122.4, 116.7, 111.8, 110.1, 65.9, 63.8, 59.1, 53.7, 50.4, 37.3, 33.7, 28.5, 15.4. The oxalate salt was precipitated from acetone and crystallized in 2-PrOH/ether; Mp 154-155° C. Anal (C$_{26}$H$_{32}$ClN$_3$O$_3$.2C$_2$H$_2$O$_4$.H$_2$O) C, H, N.

(E)-2-(4-(4-(2-Chloro-3-ethylphenyl)piperazin-1-yl)but-2-en-1-yl)isoindoline-1,3-dione (33): 32 (0.592 g, 2.11 mmol) was added to the reaction mixture of B6 (0.475 g, 2.11 mmol) and K$_2$CO$_3$ (0.1.458 g, 10.56 mmol) in acetone (25 ml) and stirred at reflux overnight. The reaction mixture was filtered, concentrated and purified using flash chromatography with 15% acetone/CHCl$_3$ as eluent to provide 0.880 g (98.2%) of product as an oil. $^1$H NMR (400 MHz, CDCl$_3$) δ 7.67 (dd, J=5.2, 3.2 Hz, 2H), 7.53 (dd, J=5.2, 3.2 Hz, 2H), 6.98 (t, J=8.0 Hz, 1H), 6.76 (t, J=6.4 Hz, 2H), 5.63 (d, J=4.4 Hz, 1H), 5.61 (d, J=4.4 Hz, 1H), 4.16 (d, J=4.0 Hz, 2H), 2.90 (m, 6H), 2.59 (q, J=8.0 Hz, 2H), 2.47 (bs, 4H), 1.06 (t, J=7.6 Hz, 3H); $^{13}$C NMR (100 MHz, CDCl$_3$) δ 167.6, 149.5, 142.9, 133.8, 132.0, 130.1, 128.5, 126.9, 126.8, 123.8, 123.1, 117.9, 60.1, 53.3, 51.4, 38.9, 27.4, 14.1.

(E)-4-(4-(2-Chloro-3-ethylphenyl)piperazin-1-yl)but-2-en-1-amine (34): The same procedure was used as described for 16a. The product was isolated in 91.2% yield and was sufficiently pure to be used for the next step without further purification. $^1$H NMR (400 MHz, CDCl$_3$) δ 6.96 (t, J=8.0 Hz, 1H), 6.75 (dd, J=8.0. 1.6 Hz, 2H), 5.63-5.57 (m, 1H), 5.53-5.46 (m, 1H), 3.13 (d, J=5.6 Hz, 2H), 2.88-2.87 (m, 6H), 2.59 (q, J=7.6 Hz, 2H), 2.47 (bs, 4H), 1.16 (bs, 2H), 1.05 (t, J=7.6 Hz, 3H); $^{13}$C NMR (100 MHz, CDCl$_3$) δ 149.5, 142.9, 135.3, 128.5, 126.8, 126.0, 123.8, 117.9, 60.4, 53.2, 51.4, 43.7, 27.4, 14.1. GC-MS (EI) m/z 293.1 (M$^+$).

(E)-N-(4-(4-(2-Chloro-3-ethylphenyl)piperazin-1-yl)but-2-en-1-yl)-4-methyl-1H-imidazole-2-carboxamide (35): 35 was prepared from 4-methyl-1H-imidazole-2-carboxylic acid and 34 according to the general amidation procedure. The crude product was purified by flash chromatography using 3% MeOH/CHCl$_3$ as eluent to give the desired product in 54.7% yield. $^1$H NMR (400 MHz, CDCl$_3$) δ 12.70-12.63 (m, 1H), 7.90 (bs, 1H), 7.13 (t, J=8.0 Hz, 1H), 6.94-6.89 (m, 2H), 6.80 (s, 1H), 5.76 (d, J=5.0, 1H), 5.73 (d, J=5.0, 1H), 4.06 (t, J=5.0, 2H), 3.05-3.04 (m, 6H), 2.75 (q, J=7.6 Hz, 2H), 2.62 (bs, 4H), 2.31 (s, 2H), 2.24 (s, 1H), 1.20 (t, J=8.0, 3H); $^{13}$C NMR (100 MHz, CDCl$_3$) δ 159.1, 149.5, 143.2, 139.9, 129.3, 129.2, 128.7, 126.9, 124.0, 118.0, 60.3, 53.4, 51.4, 40.8, 27.5, 14.1. The oxalate salt was precipitated from acetone and crystallized in MeOH/ether; Mp 166-167° C. Anal (C$_{21}$H$_{28}$ClN$_5$O.2C$_2$H$_2$O$_4$.1.25H$_2$O) C, H, N.

1-(2-Chloro-3-ethylphenyl)-4-(2-(oxiran-2-yl)ethyl)piperazine (37): 2-(2-Bromoethyl)oxirane (0.269 g, 1.78 mmol) was added to a reaction mixture of B6 (0.266 g, 1.18 mmol) and K$_2$CO$_3$ (0.491 g, 3.56 mmol) in acetone (20 mL) and stirred at reflux overnight. The crude product was filtered, concentrated and purified by flash chromatography using 12% acetone/CHCl$_3$ as eluent to provide 0.145 g (41.4%) of the product as oil. $^1$H NMR (400 MHz, CDCl$_3$) δ 7.15 (t, J=7.6 Hz, 1H), 6.95-6.91 (m, 2H), 3.06 (bs, 4H), 3.02-2.95 (m, 1H), 2.80-2.73 (m, 3H), 2.66 (bs, 4H), 2.62-2.55 (m, 2H), 2.53-2.51 (m, 1H), 1.87-1.79 (m, 1H), 1.76-1.67 (m, 1H), 1.22 (t, J=7.6 Hz, 3H); $^{13}$C NMR (100 MHz, CDCl$_3$) δ 149.6, 143.2, 128.7, 126.9, 124.0, 118.0, 55.0, 53.5, 51.6, 50.9, 47.1, 30.2, 27.5, 14.2. GC-MS (EI) m/z 294.1 (M$^+$).

1-Azido-4-(4-(2-chloro-3-ethylphenyl)piperazin-1-yl)butan-2-ol (38): A reaction mixture of 37 (0.170 g, 0.57 mmol), NaN$_3$ (0.056 g, 0.86 mmol) and NH$_4$Cl (0.062 g, 1.15 mmol) in DMF (5 mL) was heated at 100° C. for 6 h. The solvent was evaporated and the reaction mixture was diluted with water (15 mL) and extracted in EtOAc (3×15 mL). The organic layer was combined, dried, concentrated and purified by flash chromatography using 7% acetone/CHCl$_3$ as eluent to provide 0.103 g (52.9%) of the product as an oil. $^1$H NMR (400 MHz, CDCl$_3$) δ 7.17 (t, J=7.6 Hz, 1H), 6.97 (dd, J=7.6, 1.2 Hz, 1H), 6.91 (dd, J=7.6, 1.2 Hz, 1H), 4.07-4.02 ((m, 1H), 3.28 (m, 2H), 3.07 (bs, 4H), 2.85-2.71 (m, 6H), 2.64-2.61 (m, 2H), 1.87-1.77 (m, 1H), 1.60-1.54 (m, 1H), 1.26-1.22 (m, 3H); $^{13}$C NMR (100 MHz, CDCl$_3$) δ 149.2, 143.3, 128.7, 127.0, 124.3, 118.1, 73.0, 57.3, 56.6, 53.4, 51.5, 28.5, 27.5, 14.1.

1-Amino-4-(4-(2-chloro-3-ethylphenyl)piperazin-1-yl)butan-2-ol (39): A mixture of 38 (0.123 g, 0.36 mmol) and 10% Pd/C (0.050 g) in EtOAc (10 mL) was stirred under an atmosphere of hydrogen (50 psi) at room temperature for 2 h. The reaction mixture was filtered through a Celite pad and evaporated under vacuum. The reaction mixture was sufficiently pure to be used for the next step without further purification. $^1$H NMR (400 MHz, CD$_3$OD+CDCl$_3$) δ 7.07 (t, J=7.6 Hz, 1H), 6.89 (dd, J=13.6, 8.4 Hz, 2H), 4.89 (bs, 2H), 4.11 (bs, 1H), 3.33-3.17 (m, 10H), 3.04-2.99 (m, 1H), 2.64 (q, J=7.2 Hz, 2H), 2.06-1.97 (m, 2H), 1.12 (t, J=7.6 Hz, 3H); $^{13}$C NMR (100 MHz, CDCl$_3$) δ 147.5, 143.3, 128.5, 127.1, 125.1, 118.3, 65.5, 54.2, 52.7, 48.7, 44.8, 28.8, 27.2, 13.8.

N-(4-(4-(2-Chloro-3-ethylphenyl)piperazin-1-yl)-2-hydroxybutyl)-1H-indole-2-carboxamide (40): 40 was prepared from indole-2-carboxylic acid and 39 according to the general amidation procedure B using DMF as solvent. The crude product was purified by flash chromatography using 2% MeOH/CHCl$_3$ as eluent to give the desired product in 16.4% yield.

$^1$H NMR (400 MHz, CDCl$_3$) δ 9.73 (s, 1H), 7.63 (d, J=7.6 Hz, 1H), 7.43 (dd, J=8.4, 0.8 Hz, 1H), 7.28-7.23 (m, 1H), 7.16-7.09 (m, 2H), 6.95 (dd, J=7.6, 1.2 Hz, 2H), 6.91 (d, J=1.2 Hz, 1H), 6.86 (dd, J=7.6, 1.6 Hz, 1H), 4.10-4.06 (m, 1H), 3.76-3.71 (m, 1H), 3.43-3.37 (m, 1H), 3.04 (bs, 4H), 2.93-2.81 (m, 2H), 2.79-2.69 (m, 4H), 2.62 (m, 2H), 1.82-1.78 (m, 1H), 1.62-1.57 (m, 1H), 1.21 (t, J=7.6 Hz, 3H); $^{13}$C NMR (100 MHz, CDCl$_3$) δ 161.9, 149.1, 143.3, 136.3, 130.8, 128.7, 127.7, 126.9, 124.3, 124.3, 121.9, 120.5, 118.0, 112.0 102.3, 72.6, 57.3, 53.4, 51.4, 45.3, 30.9, 28.6, 27.4, 14.0. The oxalate salt was precipitated from acetone; Mp 225-226° C. Anal (C$_{25}$H$_{31}$ClN$_4$O$_2$.1.5C$_2$H$_2$O$_4$.1.75H$_2$O) C, H, N.

2-(4-(4-(3-chloro-5-ethyl-2-methoxyphenyl)piperazin-1-yl)-3-hydroxybutyl)isoindoline-1,3-dione (C1a). A mixture of compounds A7 (1 mmol) and 2-(2-(oxiran-2-yl)ethyl)isoindoline-1,3-dione (A8, 1 mmol) was stirred at reflux in 2-PrOH (20 mL) for 3 h. The reaction mixture was concentrated and purified by flash chromatography using 20% EtOAc/hexanes as eluent to provide 0.523 g (91%) of product. $^1$H NMR (400 MHz, CDCl$_3$) δ 7.85 (dd, J=5.2, 3.2 Hz, 2H), 7.71 (dd, J=5.6, 2.8 Hz, 2H), 6.84 (d, J=2.0 Hz, 1H), 6.60 (d, J=2.0 Hz, 1H), 3.93-3.79 (m, 6H), 3.13 (bs, 4H), 2.81-2.79 (m, 2H), 2.60-2.58 (m, 2H), 2.55 (q, J=8.0 Hz, 2H), 2.45-2.41 (m, 2H), 1.79 (q, J=7.2 Hz, 2H), 1.19 (t, J=8.0 Hz, 3H); $^{13}$C NMR (100 MHz, CDCl$_3$) δ 168.5, 146.4, 145.9, 140.8, 133.9, 132.2, 128.2, 123.2, 122.4, 116.7, 64.5, 63.9, 59.1, 53.8, 50.3, 35.1, 33.6, 28.4, 15.4.

2-(4-(4-(2-Chloro-3-ethylphenyl)piperazin-1-yl)-3-hydroxybutyl)isoindoline-1,3-dione (C1b): The same procedure was used as described for C1a, employing B6 (1 mmol) and 2-(2-(oxiran-2-yl)ethyl)isoindoline-1,3-dione (B7, 1 mmol). The product was purified by flash chromatography using 30% EtOAc/hexanes as eluent to afford C1b in 57% yield. $^1$H NMR (400 MHz, CDCl$_3$) 7.85 (dd, J=7.2, 5.6 Hz, 2H), 7.71 (dd, J=5.6, 3.2 Hz, 2H), 7.15 (t, J=8.0 Hz, 1H), 6.92 (dq, J=7.6, 1.6 Hz, 2H), 3.94-3.77 (m, 4H), 3.03 (bs, 4H), 2.84-2.81 (m, 2H), 2.76 (q, J=7.6 Hz, 2H), 2.59 (m, 2H), 2.46-2.38 (m 2H), 1.79 (q, J=7.0, 2H), 1.22 (t, J=7.6 Hz, 3H); $^{13}$C NMR (100 MHz, CDCl$_3$) δ 168.7, 151.7, 149.6, 143.4, 134.0, 132.4, 128.8, 127.0, 124.2, 123.4, 118.1, 64.6, 64.0, 51.8, 35.3, 33.8, 27.6, 14.2.

2-(4-(4-(3-chloro-5-ethyl-2-methoxyphenyl)piperazin-1-yl)-3-fluorobutyl)isoindoline-1,3-dione (C2a): To compound C1a (1 mmol) was added dry dichloromethane and the reaction mixture was cooled to −78 C. Maintaining the same temperature, (Diethylamino)sulfur trifluoride (DAST, 1.5 mmol) dissolved in dry dichloromethane was added drop wise and the stirring continued ed at 20° C. for 8 h. Thin layer chromatography was used to monitor the progress of the reaction. Once the reaction was complete, ice cold water was added to the reaction mixture and the product was extracted in ethylacetate and purified by flash column using 20% ethylacetate and hexane, as the eluent. 1H NMR (400 MHz, cdcl3) δ 7.95-7.80 (m, 2H), 7.79-7.62 (m, 2H), 6.82 (t, J=10.6 Hz, 1H), 6.57 (t, J=16.3 Hz, 1H), 4.92-4.66 (m, 1H), 3.97-3.83 (m, 2H), 3.83-3.74 (m, 3H), 3.64-3.41 (m, 2H), 3.11 (d, J=3.0 Hz, 4H), 2.80-2.59 (m, 4H), 2.54 (td, J=7.5, 4.4 Hz, 2H), 2.18-1.78 (m, 2H), 1.20 (dt, J=12.1, 5.0 Hz, 3H).

2-(4-(4-(2-chloro-3-ethylphenyl)piperazin-1-yl)-3-fluorobutyl)isoindoline-1,3-dione (C2b) was prepared with C2b according to the procedure described for C2a. $^1$H NMR (400 MHz, CDCl3) δ 7.90-7.80 (m, 2H), 7.77-7.66 (m, 2H), 7.14 (t, J=7.8 Hz, 2H), 6.92 (ddd, J=14.9, 7.8, 1.5 Hz, 1H), 4.94-4.65 (m, 1H), 4.12 (q, J=7.2 Hz, 2H), 3.95-3.76 (m, 2H), 3.04 (s, 2H), 2.74 (ddd, J=13.8, 12.9, 7.4 Hz, 2H), 2.64-2.44 (m, 2H), 2.20-1.92 (m, 4H), 1.58 (s, 2H), 1.24 (dt, J=16.2, 7.3 Hz, 3H).

4-(4-(3-chloro-5-ethyl-2-methoxyphenyl)piperazin-1-yl)-3-fluorobutan-1-amine (C3a) Hydrazine (3 mmol) was added to a solution of compound C2a (1 mmol) in EtOH (15 mL) and stirred at reflux for 7 h. The solvent was evaporated and the reaction mixture was diluted with 20% aq. $K_2CO_3$ solution (15 mL) and extracted in CHCl3 (2×15 mL). The organic layer was combined, dried and concentrated to afford a yellow oily product, which was sufficiently pure to be used for the next step without further purification. 1H NMR (400 MHz, CDCl$_3$) δ 6.85 (d, J=1.8 Hz, 1H), 6.61 (d, J=2.0 Hz, 1H), 4.86 (d, J=49.8 Hz, 1H), 3.83 (d, J=6.6 Hz, 3H), 3.15 (s, 2H), 2.89 (d, J=6.3 Hz, 2H), 2.72 (dt, J=19.2, 10.6 Hz, 2H), 2.59-2.48 (m, 2H), 1.56 (s, 10H), 1.20 (t, J=7.6 Hz, 3H).

4-(4-(2-chloro-3-ethylphenyl)piperazin-1-yl)-3-fluorobutan-1-amine (C3b) was prepared with C2b using the procedure described for C3a. $^1$H NMR (400 MHz, CDCl3) δ 7.15 (t, J=7.8 Hz, 1H), 6.95 (dd, J=19.8, 11.6 Hz, 2H), 4.92 (d, J=49.8 Hz, 1H), 3.07 (s, 2H), 2.89 (dd, J=13.0, 6.2 Hz, 2H), 2.81-2.67 (m, 2H), 2.17 (s, 4H), 1.54 (s, 8H), 1.22 (t, J=7.5 Hz, 3H).

N-(4-(4-(3-chloro-5-ethyl-2-methoxyphenyl)piperazin-1-yl)-3-fluorobutyl)-1H-indole-2-carboxamide (C4a) was prepared from indole-2-carboxylic acid and C3a according to the general amidation procedure A. The crude product was purified by flash chromatography using 30% acetone/CHCl3 as eluent to give the desired product in 50% yield. 1H NMR (400 MHz, CDCl3) δ 9.16 (s, 1H), 8.02 (s, 1H), 7.66 (t, J=8.7 Hz, 1H), 7.44 (d, J=8.3 Hz, 1H), 7.34-7.22 (m, 1H), 7.15 (dd, J=13.2, 6.1 Hz, 1H), 6.84 (dd, J=7.6, 1.7 Hz, 1H), 6.60 (d, J=2.0 Hz, 1H), 6.55 (s, 1H), 4.90 (d, J=49.1 Hz, 1H), 3.83 (s, 2H), 3.79-3.58 (m, 1H), 3.15 (s, 2H), 2.95 (s, 1H), 2.92-2.84 (m, 2H), 2.75-2.64 (m, 3H), 2.56 (dt, J=15.2, 5.6 Hz, 2H), 2.02 (dd, J=17.8, 14.3 Hz, 2H), 1.59 (s, 2H), 1.20 (t, J=7.6 Hz, 3H). The oxalate salt was precipitated from acetone; Anal ($C_{26}H_{32}ClFN_4O_2.1.2C_2H_2O_4.H_2O$) C, H, N.

N-(4-(4-(3-chloro-5-ethyl-2-methoxyphenyl)piperazin-1-yl)-3-fluorobutyl)benzofuran-2-carboxamide (C4b) was prepared from benzofuran-2-carboxylic acid and C3a according to the general amidation procedure A. The crude product was purified by flash chromatography using 30% acetone/CHCl3 as eluent to give the desired product in 55% yield. 1H NMR (400 MHz, CDCl3) δ 8.02 (s, 1H), 7.72-7.64 (m, 1H), 7.51-7.44 (m, 1H), 7.44-7.36 (m, 1H), 7.33-7.26 (m, 1H), 7.01 (d, J=12.0 Hz, 1H), 6.85 (d, J=2.0 Hz, 1H), 6.61 (d, J=2.0 Hz, 1H), 4.89 (d, J=49.9 Hz, 1H), 3.84 (s, 3H), 3.74-3.61 (m, 2H), 3.16 (s, 4H), 2.95 (s, 1H), 2.88 (d, J=0.5 Hz, 1H), 2.79-2.64 (m, 5H), 2.59-2.48 (m, 2H), 2.24-1.97 (m, 2H), 1.59 (s, 4H), 1.19 (t, J=7.6 Hz, 3H). $^{13}$C NMR (101 MHz, CDCl3) δ 159.00, 154.65, 148.55, 146.26, 146.01, 140.71, 128.23, 127.61, 126.79, 123.60, 122.72, 122.33, 116.60, 111.69, 110.41, 106.50, 92.03, 90.30, 61.99, 59.24, 54.36, 50.18, 35.88, 33.14, 28.53, 15.39. The oxalate salt was precipitated from acetone. Anal ($C_{26}H_{31}ClFN_3O_3 1.1C_2H_2O_4.H_2O$) C, H, N.

N-(4-(4-(2-chloro-3-ethylphenyl)piperazin-1-yl)-3-fluorobutyl)-1H-indole-2-carboxamide (ABS01-113 (C5a) was prepared from indole-2-carboxylic acid and C3b according to the general amidation procedure A. The crude product was purified by flash chromatography using 30% acetone/CHCl3 as eluent to give the desired product in 60% yield. 1H NMR (400 MHz, CDCl3) δ 9.11 (s, 1H), 7.86 (s, 1H), 7.49 (s, 1H), 7.28 (s, 1H), 7.19-7.06 (m, 1H), 7.06-6.93 (m, 1H), 6.85-6.73 (m, 2H), 6.68 (s, 1H), 6.48 (s, 1H), 4.76 (d, J=48.0 Hz, 1H), 3.53 (d, J=25.1 Hz, 2H), 2.92 (s, 1H), 2.80 (ddd, J=6.7, 3.6, 1.8 Hz, 3H), 2.73 (ddd, J=5.1, 3.6, 1.8 Hz, 3H), 2.67-2.54 (m, 3H), 1.85 (s, 2H), 1.51 (s, 3H), 1.16-0.98 (m, 3H). $^{13}$C NMR (101 MHz, CDCl3) δ 162.50, 161.68, 149.42, 143.22, 136.16, 130.50, 128.69, 127.62, 126.88, 124.31, 124.10, 121.84, 120.67, 117.97, 111.80, 101.97, 92.45, 90.77, 62.04, 54.00, 51.27, 36.39, 32.99, 31.46, 27.45, 14.08. The oxalate salt was precipitated from acetone; Mp 228-229° C. Anal ($C_{25}H_{29}ClFN_3O_2.C_2H_2O_4.0.5H_2O$) C, H, N.

N-(4-(4-(2-chloro-3-ethylphenyl)piperazin-1-yl)-3-fluorobutyl)benzofuran-2-carboxamide (C5b) was prepared from benzofuron-2-carboxylic acid and C3b according to the general amidation procedure A. The crude product was purified by flash chromatography using 30% acetone/CHCl3 as eluent to give the desired product in 60% yield. 1H NMR (400 MHz, CDCl3) δ 8.02 (s, 1H), 7.67 (ddd, J=7.8, 1.2, 0.7 Hz, 1H), 7.48 (ddd, J=5.4, 4.5, 3.0 Hz, 1H), 7.41 (ddd, J=8.3, 7.2, 1.3 Hz, 1H), 7.32-7.26 (m, 1H), 7.26 (s, 1H), 7.15 (t, J=7.8 Hz, 1H), 7.01 (s, 1H), 6.93 (ddd, J=15.4, 7.8, 1.5 Hz, 1H). 5.03-4.75 (m, 1H), 3.75-3.61 (m, 3H), 3.08 (s, 2H), 2.95 (s, 1H), 2.88 (d, J=0.5 Hz, 3H), 2.83-2.71 (m, 3H), 2.18-1.88 (m, 2H), 1.61 (s, 3H), 1.27-1.13 (m, 3H). 13C NMR (101 MHz, CDCl3) δ 158.92, 154.70, 149.48, 148.62, 143.22, 128.59, 127.50, 126.81, 124.02, 123.68, 122.71, 117.81, 111.69, 110.39, 92.14, 90.36, 62.21, 61.96, 54.09, 51.40, 35.88, 33.17, 32.92, 27.34, 14.08. The oxalate salt was precipitated from acetone; Anal ($C_{25}H_{29}ClFN_3O_2.1.3C_2H_2O_4.H_2O$) C, H, N.

Further abbreviations used in the following examples: DA, dopamine; TM, transmembrane; D2R, dopamine D2 receptor; D3R, dopamine D3 receptor; D4R, dopamine D4 receptor; 5-HT, 5-hydroxytryptamine (serotonin); i.p., intraperitoneal; PPB, potassium phosphate buffer; s.c. subcutaneous; and THC, (6aR,10aR)-delta-9-tetrahydrocannabinol.

Example 2. Radioligand Binding Assays

Binding at dopamine D2-like receptors was determined using previously described methods. (Chen et al. "Tranylcypromine substituted cis-hydroxycyclobutylnaphthamides as potent and selective dopamine D (3) receptor antagonists." J. Med. Chem. 2014, 57, 4962-4968) Membranes were prepared from HEK293 cells expressing human D2R, D3R or D4R, grown in a 50:50 mix of DMEM and Ham's F12 culture media, supplemented with 20 mM HEPES, 2 mM L-glutamine, 0.1 mM non-essential amino acids, 1× antibiotic/antimycotic, 10% heat-inactivated fetal bovine serum, and 200 μg/mL hydromycin (Life Technologies, Grand Island, N.Y.) and kept in an incubator at 37° C. and 5% $CO_2$. Upon reaching 80-90% confluence, cells were harvested using pre-mixed Earle's Balanced Salt Solution (EBSS) with 5 μM EDTA (Life Technologies) and centrifuged at 3000 rpm for 10 min at 21° C. The supernatant was removed and the pellet was resuspended in 10 mL hypotonic lysis buffer (5 mM $MgCl_2 \cdot 6 H_2O$, 5 mM Tris, pH 7.4 at 4° C.) and centrifuged at 20,000 rpm for 30 min at 4° C. The pellet was then resuspended in fresh EBSS buffer made from 8.7 g/L Earle's Balanced Salts without phenol red (US Biological, Salem, Mass.), 2.2 g/L sodium bicarbonate, pH to 7.4. A Bradford protein assay (Bio-Rad, Hercules, Calif.) was used to determine the protein concentration and membranes were diluted to 500 μg/mL and stored in a −80° C. freezer for later use.

Radioligand competition binding experiments were conducted using thawed membranes. Test compounds were freshly dissolved in 30% DMSO and 70% $H_2O$ to a stock concentration of 100 μM. To assist the solubilization of free-base compounds, 20 μl of glacial acetic acid was added along with the DMSO. Each test compound was then diluted into 13 half-log serial dilutions using 30% DMSO vehicle; final test concentrations ranged from 10 μM to 10 pM. Previously frozen membranes were diluted in fresh EBSS to a 100 μg/mL (for hD2R or hD3R) or 200 μg/mL (hD4R) stock for binding. Radioligand competition experiments were conducted in glass tubes containing 300 μl fresh EBSS buffer with 0.2 mM sodium metabisulfite, 50 μl of diluted test compound, 100 μl of membranes (10 μg total protein for hD2R or hD3R, 20 μg total protein for hD4R), and 50 μl of [$^3$H]N-methylspiperone (0.4 nM final concentration; Perkin Elmer). Nonspecific binding was determined using 10 μM butaclamol (Sigma-Aldrich, St. Louis, Mo.) and total binding was determined with 30% DMSO vehicle. All compound dilutions were tested in triplicate and the reaction incubated for one hour at room temperature. The reaction was terminated by filtration through Whatman GF/B filters, presoaked for one hour in 0.5% polyethylenimine, using a Brandel R48 filtering manifold (Brandel Instruments, Gaithersburg, Md.). The filters were washed 3 times with 3 mL of ice cold EBSS buffer and transferred to scintillation vials. 3 mL CytoScint liquid scintillation cocktail (MP Biomedicals, Solon, Ohio) was added and vials were counted using a Perkin Elmer Tri-Carb 2910 TR liquid scintillation counter (Waltham, Mass.). $IC_{50}$ values for each compound were determined from dose-response curves and $K_i$ values were calculated using the Cheng-Prusoff equation; these analyses were performed using GraphPad Prism version 5.00 for Windows (GraphPad Software, San Diego, Calif.). Reported $K_i$ values were determined from least three independent experiments.

TABLE 1A

Human $D_2$R-Family Receptor Subtype Binding Data on piperazine butyl arylcarboxamide derivatives[a]

| Compd. | Ar | $R^1$ | $R^2$ | $R^3$ | Linker | cLogP[b] | PSA | $D_2$R | $D_3$R $K_i$ ± SEM (nM) | $D_4$R | $D_2/D_3$ | $D_4/D_3$ | $D_4/D_2$ |
|---|---|---|---|---|---|---|---|---|---|---|---|---|---|
| 18 | indole | Cl | H | H | propyl | 5.76 | 47.61 | 5.50 ± 0.805 | 0.142 ± 0.0249 | 334 ± 113 | 39 | 2352 | 61 |
| 19 | indole | Cl | H | H | OH-branched | 5.17 | 67.84 | 151 ± 25.4 | 0.362 ± 0.0474 | 5523 ± 1655 | 417 | 15257 | 37 |
| 20 | benzofuran | Cl | H | H | propyl | 5.74 | 44.81 | 6.34 ± 0.959 | 0.153 ± 0.00527 | 356 ± 64.4 | 41 | 2327 | 56 |
| 21 | benzofuran | Cl | H | H | OH-branched | 5.14 | 65.04 | 164 ± 32.4 | 0.985 ± 0.105 | 2381 ± 110 | 166 | 2417 | 15 |

TABLE 1A-continued

Human D₂R-Family Receptor Subtype Binding Data on piperazine butyl arylcarboxamide derivatives[a]

$$\text{Ar}-\overset{O}{\underset{}{C}}-\overset{H}{\underset{}{N}}-[\text{Linker}]-N\underset{\diagdown}{\diagup}\text{piperazine}-N-\text{Ar}(R^1, R^2, R^3, \text{Et})$$

| Compd. | Ar | R¹ | R² | R³ | Linker | cLogP[b] | PSA | $D_2R$ | $D_3R$ $K_i \pm$ SEM (nM) | $D_4R$ | $D_2/D_3$ | $D_4/D_3$ | $D_4/D_2$ |
|---|---|---|---|---|---|---|---|---|---|---|---|---|---|
| 22 | imidazo[1,2-a]pyridin-3-yl | Cl | H | H | propyl | 5.52 | 51.18 | 5.64 ± 0.98 | 0.33 ± 0.085 | 819 ± 175 | 17.1 | 2482 | 145.2 |
| 23 | imidazo[1,2-a]pyridin-3-yl | Cl | H | H | 2-hydroxybutyl | 4.93 | 71.41 | 193 ± 40.5 | 4.23 ± 0.84 | 11300 | 45.6 | 2671 | 58.5 |
| 24 | 6-methylimidazo[2,1-b]thiazol-5-yl | Cl | H | H | propyl | 5.43 | 51.18 | 4.65 ± 1.24 | 0.94 ± 0.13 | 143 ± 3.18 | 4.9 | 152 | 30.8 |
| 25 | 5-ethyl-1H-imidazol-4-yl | Cl | H | H | propyl | 5.38 | 59.97 | 12.5 ± 1.07 | 1.14 ± 0.17 | 500 ± 30.9 | 11.0 | 439 | 40.0 |
| 26 | 5-methyl-1H-imidazol-4-yl | Cl | H | H | propyl | 4.391 | 59.97 | 12.2 ± 2.58 | 0.62 ± 0.096 | 529 ± 42.3 | 19.7 | 853 | 43.4 |
| 27 | 5-methyl-1H-imidazol-4-yl | Cl | H | H | 2-hydroxybutyl | 3.79 | 80.2 | 150 ± 13.1 | 11.2 ± 2.66 | 1960 ± 0344 | 13.4 | 175 | 13.1 |
| 28 | 1H-indol-3-yl | H | OMe | Cl | propyl | 5.53 | 56.84 | 27.8 ± 6.71 | 0.341 ± 0.0312 | 1045 ± 279 | 82 | 3065 | 38 |
| 29 | 1H-indol-3-yl | H | OMe | Cl | 2-hydroxybutyl | 4.93 | 77.07 | 17127 ± 5087 | 6.29 ± 0.877 | >>100μM± | 2723 | — | — |
| 30 | benzofuran-2-yl | H | OMe | Cl | propyl | 5.50 | 54.04 | 137 ± 9.00 | 3.19 ± 0.268 | 714 ± 293 | 43 | 224 | 5.2 |
| 31 | benzofuran-2-yl | H | OMe | Cl | 2-hydroxybutyl | 4.91 | 74.27 | 1619 ± 339 | 36.1 ± 5.00 | 5285 ± 319 | 45 | 146 | 3.3 |

TABLE 1A-continued

Human D$_2$R-Family Receptor Subtype Binding Data on piperazine butyl arylcarboxamide derivatives[a]

General structure: Ar-C(O)-NH-CH$_2$-[Linker]-CH$_2$-N(piperazine)-N-aryl where aryl has R$^1$, ethyl, R$^2$, R$^3$ substituents.

| Compd. | Ar | R$^1$ | R$^2$ | R$^3$ | Linker | cLogP[b] | PSA | D$_2$R K$_i$ ± SEM (nM) | D$_3$R K$_i$ ± SEM (nM) | D$_4$R | D$_2$/D$_3$ | D$_4$/D$_3$ | D$_4$/D$_2$ |
|---|---|---|---|---|---|---|---|---|---|---|---|---|---|
| 35 | 4-methylimidazole (HN-imidazole-CH$_3$) | Cl | H | H | propenyl (CH=CH-CH$_3$) | 4.31 | 59.97 | 16.1 ± 1.2 | 1.28 ± 0.22 | 503 ± 157 | 12.6 | 393 | 31.2 |
| 40 | indol-2-yl | Cl | H | H | CH(OH)CH$_2$CH$_3$ branch | 5.05 | 67.84 | 6.83 ± 0.53 | 0.20 ± 0.018 | 305 ± 70.5 | 34.2 | 1525 | 44.7 |

[a]Binding inhibition values determined using HEK 293 cells transfected with hD2LR or hD3R and [$_3$H]N-methylspiperone radioligand as described in (Chen et al. "Tranylcypromine substituted cis-hydroxycyclobutylnaphthamides as potent and selective dopamine D(3) receptor antagonists." J. Med. Chem. 2014, 57, 4962-4968) [b]Partition coefficients (clogP) were calculated using ChemDraw Professional Ultra 15.0.

TABLE 1B

| Compounds | Structures | [$^3$H]-N-methylspiperone competition[a] | | |
|---|---|---|---|---|
| | | D$_2$R K$_i$ ± SEM (nM) | D$_3$R K$_i$ ± SEM (nM) | D$_2$/D$_3$ |
| (R)-29 | indole-2-carboxamide-NH-CH$_2$CH$_2$-CH(OH)-CH$_2$-piperazine-N-(3-ethyl-6-methoxy-5-chlorophenyl), R-configuration at OH | 10200 ± 1870 | 5.97 ± 1.19 | 1709 |
| (S)-29 | indole-2-carboxamide-NH-CH$_2$CH$_2$-CH(OH)-CH$_2$-piperazine-N-(3-ethyl-6-methoxy-5-chlorophenyl), S-configuration at OH | 11600 ± 1150 | 33.4 ± 8.46 | 347 |

TABLE 1B-continued

| Compounds | Structures | [³H]-N-methylspiperone competition[a] | | |
|---|---|---|---|---|
| | | $D_2R$ $K_i$ ± SEM (nM) | $D_3R$ $K_i$ ± SEM (nM) | $D_2/D_3$ |
| (±)-29 | 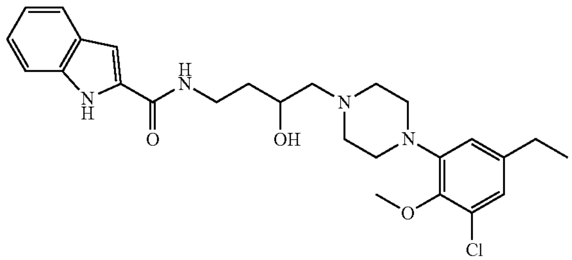 [SMILES: CCc1cc(Cl)c(OC)c(N2CCN(CC(O)CCNC(=O)c3cc4ccccc4[nH]3)CC2)c1] | 11400 ± 3270 | 6.84 ± 1.18 | 1667 |
| (R)-19 | 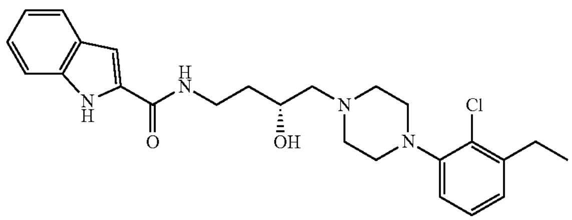 [SMILES: CCc1cccc(N2CCN(C[C@H](O)CCNC(=O)c3cc4ccccc4[nH]3)CC2)c1Cl] | 68.1 ± 12.3 | 0.245 ± 0.0915 | 278 |
| (S)-19 | | 200 ± 57.9 | 0.700 ± 0.286 | 286 |
| (±)-19 | 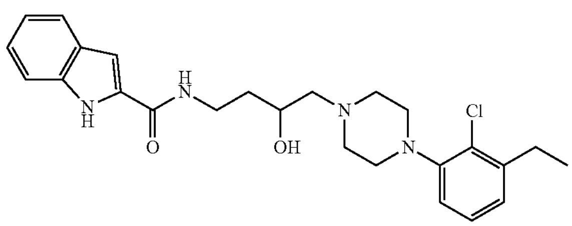 [SMILES: CCc1cccc(N2CCN(CC(O)CCNC(=O)c3cc4ccccc4[nH]3)CC2)c1Cl] | 119 ± 11.1 | 0.351 ± 0.114 | 339 |
| C4a | 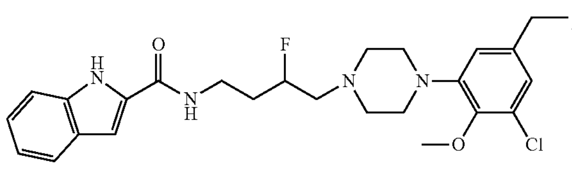 | 27100 ± 11600 | 28.0 ± 5.53 | 968 |
| C4b | 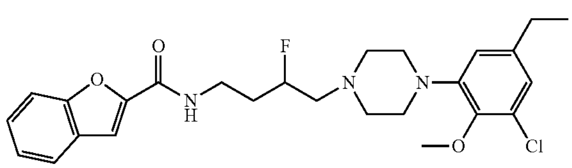 [SMILES: CCc1cc(Cl)c(OC)c(N2CCN(CC(F)CCNC(=O)c3cc4ccccc4o3)CC2)c1] | 9740 ± 2100 | 89.9 ± 12.3 | 108 |
| C5a | 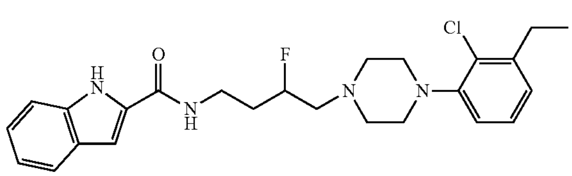 [SMILES: CCc1cccc(N2CCN(CC(F)CCNC(=O)c3cc4ccccc4[nH]3)CC2)c1Cl] | 124 ± 15.8 | 0.482 ± 0.150 | 257 |

TABLE 1B-continued

| | | [3H]-N-methylspiperone competition[a] | | |
|---|---|---|---|---|
| | | D₂R | D₃R | |
| Compounds | Structures | $K_i$ ± SEM (nM) | $K_i$ ± SEM (nM) | $D_2/D_3$ |
| C5b | | 295 ± 30.1 | 2.09 ± 0.484 | 141 |

[a] The values represent the arithmetic mean ± SEM of triplicate determinations from at least three independent experiments. IC₅₀ values for each compound were determined from dose-response curves and $K_i$ values were calculated by the Cheng-Prusoff equation using GraphPad Prism version 6.00 for Macintosh. The competition experiments were performed, similarly to what previously reported, in presence of 0.4 nM [3H]-N-methylspiperone, 10 half-log serial dilutions of test drugs in triplicate and membrane preparations from stably transfected HEK293 cells expressing $D_{2L}R$ or $D_3R$ ($D_{2L}R$ 20 μg/well and $D_3R$ 20 μg/well). The binding experiments were conducted in 96-well plates containing 300 μl fresh binding buffer (EBSS at pH 7.4), 50 μl of diluted test compound, 100 μl of membranes and 50 μl of radioligand. The binding reactions were incubated for 1 hour at room temperature and then terminated by filtration through Perkin Elmer UniFilter-96 GF/B filters, presoaked for one hour in 0.5% polyethylenimine.

PHARMACOLOGICAL RESULTS AND DISCUSSION

The binding affinities of the compounds were evaluated by performing competition binding studies with [3H]N-methylspiperone using membranes prepared from HEK₂₉₃ cells expressing either the human $D_2R$ or $D_3R$.

Binding data for the full length substituted ligands are shown in Tables 1A and 1B. In addition, cLogP values and polar surface area (PSA) were calculated to provide measures of lipophilicity and predicted brain penetration respectively, for the full length compounds. The majority of analogues demonstrated binding affinities in the low to sub-nanomolar range for $D_3R$. In the 1-(2-chloro-3-ethylphenyl)piperazine based series (18-27), both 18 and 19 showed high binding affinities for $D_3R$ ($K_i$=0.14 and 0.36 nM, respectively). Moreover, 19 showed $D_2R/D_3R$ selectivity of >400 fold. When the indole moiety of 18 and 19 was replaced with benzofuran, subnanomolar binding affinities were maintained for both 20 and 21, but $D_3R$ selectivity was reduced due to an improvement in $D_2R$ affinities. When the indole ring was also replaced with other heteroaryl ring systems, such as 2-(imidazo[1,2-a]pyridine) (22 and 23), 5-(6-methylimidazo[2,1-b]thiazole) (24), 2-(4-ethyl-1H-imidazole) (25), 2-(4-methyl-1H-imidazole) (26 and 27). In most of cases, although high $D_3R$ binding affinities were retained, relative improvements in $D_2R$ binding affinities reduced $D_3R$ selectivity. No major change in the affinity and selectivity of 26 was observed when a trans-butenyl linker was introduced between the aryl amide and piperazine moiety to afford 35.

In the more highly substituted 1-(3-chloro-5-ethyl-2-methoxyphenyl)piperazine-based series (28-31), the indole 28 showed a similar binding profile to its analogue 18. Compound 29 exhibited high affinity ($K_i$=6.29 nM) and the greatest $D_3R$ versus $D_2R$ binding selectivity, (2700 fold) of all the 4-phenylpiperazines. The benzofuran derivatives 30 and 31 showed reduced $D_3R$ binding affinities and either similar or lower $D_3R$ selectivities, in comparison to 20 and 21, respectively. The introduction of a 3—OH group in the butyl linking chain resulted in lower cLogP values, predicting decreased lipophilicity, compared to corresponding parent aliphatic compounds. Compared to all the 3-OH-butyl analogues, the 2-OH-butyl derivative 40 showed high $D_3R$ affinity ($K_i$=0.20 nM) but it exhibited lower $D_3R$ selectivity, similar to compounds that had no OH substitution in the linking chain. None of the compounds demonstrated high binding affinity for $D_4R$.

The full length molecules based on both 3-chloro-5-ethyl-2-methoxyphenylpiperazine and 2-chloro-3-ethylphenylpiperazine showed high $D_3R$ binding affinities and selectivities over $D_2R$.

The replacement of the indole with other heteroaryl ring systems showed no improvement in $D_3R$ selectivity.

Example 3. Microsomal Metabolism Studies: Rat, Rhesus Monkey, and Human Liver Microsomes Compound (±)-29 was analyzed in a monkey liver microsomal stability assay against a control. Additional side by side stability studies between compound (±)-29 and PG648 (Compound 1) were also conducted in rat liver and monkey liver microsomal stability assays. Compound 29 demonstrated improved metabolic stability as compared to Compound 1 in both species.

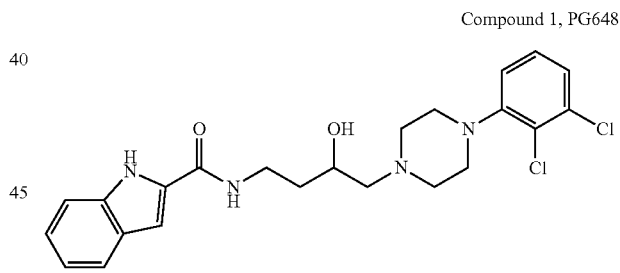

Compound 1, PG648

Methods: Phase I metabolic stability assay was conducted in rat and rhesus monkey liver microsomes. For phase I metabolism, the reaction was carried out with 100 mM potassium phosphate buffer, pH 7.4, in the presence of NADPH regenerating system (1.3 mM NADPH, 3.3 mM glucose 6-phosphate, 3.3 mM MgCl2, 0.4 U/mL glucose-6-phosphate dehydrogenase, 50 μM sodium citrate). Reactions in triplicate were initiated by addition of the liver microsomes to the incubation mixture (compound final concentration was 10 μM; 0.5 mg/mL microsomes). Negative controls in the absence of cofactors were carried out to determine the specific cofactor-free degradation. Compound disappearance was monitored via LC/MS/MS. Chromatographic analysis was performed using an Accela™ ultra high-performance system consisting of an analytical pump, and an autosampler coupled with TSQ Vantage mass spectrometer (Thermo Fisher Scientific Inc., Waltham Mass.). Separation of the analyte from potentially interfering material was achieved at ambient temperature using Agilent Eclipse Plus column (100×2.1 mm i.d.) packed with a 1.8 μm C18 stationary phase. The mobile phase used was composed of 0.1% Formic Acid in Acetonitrile and 0.1% Formic Acid in H$_2$O with gradient elution, starting with 10% (organic) linearly increasing to 99% up to 2 min, maintaining at 99% (2-2.5 min) and re-equilibrating to 10% by 2.7 min. The total run time for each analyte was 5.0 min.

Figure 2:
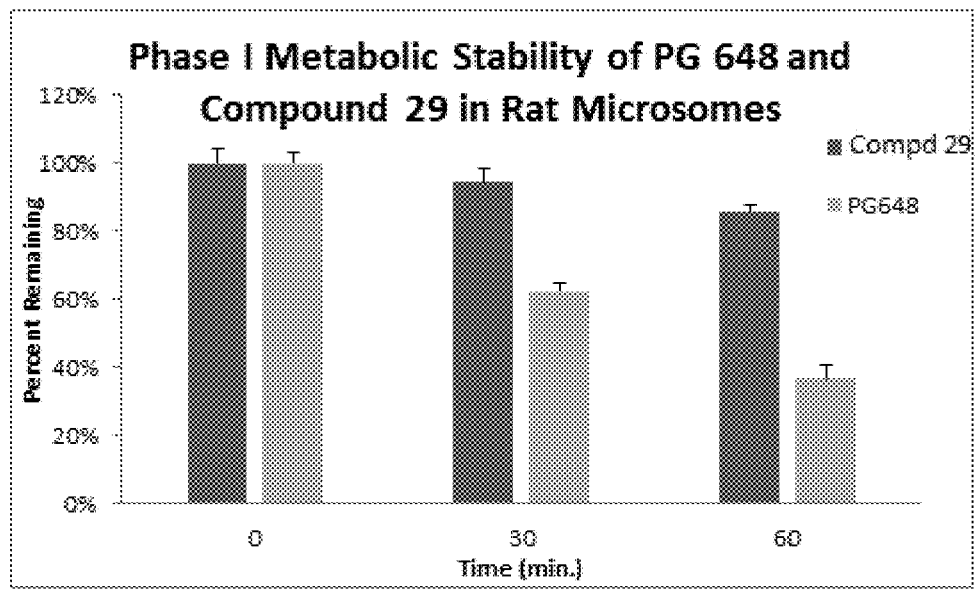
FIG. 2 illustrates the comparative results of compound 29 versus PG648, compound 1 in a rat liver microsomal stability assay.

The comparative results of the monkey liver microsomal stability assay shows compound 29 exhibits surprisingly high metabolic stability especially in comparison to PG648 (FIG. 1). The results further show compound 29 exhibits excellent Phase I metabolism in rat liver microsomes (FIG. 2) and is significantly more stable than PG648.

Mouse Microsomal Stability Assay. The phase I metabolic stability assay for compound 29 was also conducted in mouse liver microsomes. The reaction was carried out with 100 mM potassium phosphate buffer, pH 7.4, in the presence of NADPH regenerating system, (compound final concentration was 10 μM; 0.5 mg/mL microsomes). Positive controls for phase I metabolism (testosterone) were also evaluated. Compound disappearance was monitored over time using a liquid chromatography and tandem mass spectrometry (LC/MS/MS) method. All reactions were sampled in triplicate. Chromatographic analysis was performed using an Accela ultra high-performance system consisting of an analytical pump and an autosampler coupled with a TSQ Vantage mass spectrometer (Thermo Fisher Scientific Inc., Waltham, Mass.). Separation of the analyte from potentially interfering material was achieved at ambient temperature using Agilent Eclipse Plus column (100 mm×2.1 mm i.d.) packed with a 1.8 μm C18 stationary phase. The mobile phase used was composed of 0.1% formic acid in acetonitrile and 0.1% formic acid in H$_2$O with gradient elution, starting with 10% (organic) linearly increasing to 99% up to 2 min, maintaining at 99% (2-2.5 min) and reequilibrating to 10% by 2.7 min. The total run time for each analyte was 4.5 min. The results revealed compound 29 showed excellent metabolic stability with >80% remaining over 1 h.

Further Phase I metabolic stability assays were conducted on racemic compound (±)-29 and each enantiomer (R)-29 and (S)-29. The results, provided in the table below, illustrate the Phase I metabolic stability in human liver microsomes where 70-76% of intact drug remains after 1 hour for all compounds.

| Compound | Species | % at 0 min. | % at 30 min. | % at 60 min. |
|---|---|---|---|---|
| (±)-29 | Rat | 100 | 95 | 85 |
| (±)-29 | Monkey | 100 | 79 | 66 |
| (±)-29 | Human | 100 | 89 | 73 |
| (R)-29 | Rat | 100 | 80 | 68 |
| (R)-29 | Monkey | 100 | 9 | 4 |
| (R)-29 | Human | 100 | 79 | 70 |
| (S)-29 | Rat | 100 | 70 | 57 |
| (S)-29 | Monkey | 100 | 56 | 38 |
| (S)-29 | Human | 100 | 84 | 76 |

Example 4. Oxycodone Self-Administration Studies in Rats with Compound 29 and Compound 19

Standard intravenous oxycodone self-administration methods were used to assess the effects of DA D3 receptor antagonist compound 29 and compound 19 on oxycodone self-administration in rats.

MATERIALS AND METHODS: Male Long-Evans rats (Charles-River, Raleigh, N.C.) were used. They were housed individually under a reversed 12 hr light-dark cycle (light on at 7:00 PM) upon arrival, with free access to food and water, and were allowed to acclimate to the new environment at least for 7 days prior to initiate the experiment. All the experimental procedures were consistent with the "Principles of Laboratory Animal Care" published by National Institutes of Health (NIH publication 86-23, 1996) and were approved by the NIDA Animal Care and Use Committee.

Surgery: Rats (300-350 g) used for oxycodone self-administration were first implanted with an intravenous catheter. They were anaesthetized with pentobarbital (30 mg/kg i.p.) supplemented with chloral hydrate (140 mg/kg, i.p.). A small incision was next made to the right of the midline of the neck and the external jugular vein was externalized and an i.v. catheter, made of microrenathane (Braintree Scientific Inc., Braintree, Mass., USA) was inserted with its tip reaching right atrium. The catheter was secured to the vein with silk suture and the other end fed subcutaneously around the back of the neck to exit near the back of the skull. The end was slipped over a bent 24-gauge stainless steel cannula (Plastic One Inc., Roanoke, Va., USA) with a threaded head used to secure a dummy cannula and, during experimentation, an infusion line. The catheter and the guide cannula were then secured to the skull with four stainless steel screws threaded into the skull and dental cement and the wound was sutured.

After surgery, the catheters were flushed daily with a gentamicin-heparin-saline solution (30 IU/ml heparin; ICN Biochemicals, Cleveland, Ohio, USA) as precaution against catheterr clogging and infection. The animals were allowed to recover for at least 5 days before the behavioral training started.

Self-administration apparatus and oxycodone self-administration training: Rats in 3 experimental tests were first trained to self-administer oxycodone. The self-administration apparatus and procedures have been described previously (Xi et al., 2004, 2005). After recovery from surgery, each rat was connected by polyethylene tubing (protected by a steel coil spring) and a one-channel liquid swivel to a syringe pump (Razel Sci., Stamford, Conn.) controlled by a microprocessor and placed in an operant chamber (Med Associates, Georgia, Vt.) equipped with a 15 w house light and two response levers (one active and one inactive) 6.5 cm above the chamber floor. A cue light and a speaker were equipped 12 cm above the active lever. Each session began with the insertion of the active lever into the chamber and the illumination of the house light which kept on until the end of the session. Each rat was trained in 3-hour daily sessions to press the active lever on a fixed ratio-1 (FR-1) schedule of reinforcement for i.v. oxycodone infusion. They were first trained at a unit dose of 0.1 mg/kg/infusion for 2 weeks followed by 0.5 mg/kg/infusion for another week. Each active lever-press resulted in an activation of light-tone compound cue and a delivery of 0.08 ml oxycodone over 4.6 sec. This infusion time was also served as a timeout period during which the light-tone cue was kept activated and animal' responses on the active lever were recorded but had no scheduled consequence. Animal's responses on the inactive lever were also recorded but not rewarded.

Experiment 1. Effects of D3 receptor blockade by compound 29 on oxycodone self-administration. The effects of compound 29 on oxycodone self-administration were tested on the next day after completion of self-administration training. The rats were first assigned into 4 experimental groups and injected with either one dose of the drug (5, 15 or 25 mg/kg) or vehicle (25% 2-hydroxypropyl-β-cyclodextrin) used to dissolve the drug. Fifteen min after inject, the rats were put into the self-administration chambers and were allowed for another self-administration session at last trained oxycodone dose. Animals' responses on both active and inactive levers and oxycodone infusions during the 3 hr session were recorded. A corresponding experiment was conducted with compound 19.

Experiment 2. Effects of D3 receptor blockade by compound 29 on animals' responding during saline substitution testing. Following the completion of the self-administration testing, rats were allowed to self-administer oxycodone for another 4 daily sessions. On the fifth day morning, oxycodone solution in the infusion syringes was replaced by saline and the animals were injected with either compound 29 (5 or 15 mg/kg) or vehicle. Fifteen min after injection, they were placed in the chambers and allowed to lever-press for saline infusion for 3 hr. Animals' responses on the active and inactive levers and the number of saline infusions during the 3 hr test session were recorded Experiment 3. Effects of D3 receptor blockade by compound 29 on reinstatement of drug-seeking induced by oxycodone priming. After completion of self-administration training, three additional groups of animals were exposed to the extinction conditions, in which cocaine was replaced by saline, and the cocaine-associated cue-light and tone were turned off. Active lever-pressing led only to saline infusion. Daily 3 hr extinction sessions for each rat continued until lever presses ≤10 times per 3 h session for at least 3 consecutive days. On the test day, the groups of rats received either the vehicle or one of 2 doses of compound 29 (5 or 15 mg/kg). Fifteen min after injection, they were given a priming injection of oxycodone (1 mg/kg i.p.) and immediately put into the self-administration chambers. Animals were allowed to press levers for another extinction session and their responses on the levers were recorded.

Place-conditioning apparatus and effects of compound 29 on naloxone-precipitated conditioned place aversion (CPA). The place-conditioning apparatus (Med Associates, St Albans, Vt.) consisted of two compartments (21×28 cm²) linked by a gray connecting area (21×12.5 cm²); a sliding door separated each compartment from the connecting area. The two end compartments differed in wall color (black vs white), floor type (grid vs net), and illumination; preference for the end compartments was balanced by using weaker illumination in the reflective (and normally less-preferred) white compartment and stronger illumination in the non-reflective black compartment. The paradigm was further 'balanced' by associating the training injections with the white side in half the animals and with the black side in the remaining animals.

The CPA procedures in this study were similar to those described by others (Azar et al., 2003; Olmstead and Burns 2005; 2012). Briefly, one day before drug treatments started, rats (200-250 g) were randomly divided into 6 groups and were allowed to explore their assigned conditioning apparatus for 15 min (preconditioning). Treatments started on the next day morning: 3 groups were injected with oxycodone (3 mg/kg, ip.) and another 3 with saline (1 ml/kg) twice daily for 7 days. The 2 injections in a day were given at 8 a.m. and 6 p.m., respectively. Saline (1 ml/kg, s.c.) and naloxone (0.3 mg/kg, s.c.) were administered 4 hr following morning injection of oxycodone on the $4^{th}$, $6^{th}$ and $5^{th}$, $7^{th}$ day, respectively. Oxycodone-treated rats were placed into one compartment for 30 min immediately following each of 2 naloxone injections while into another compartment following each of saline injections. Vehicle or one dose of compound 29 (5 or 15 mg/kg, i.p.) were given 1 hr before each naloxone conditioning session. The 3 groups of saline-treated rats were conditioned with naloxone, vehicle and compound 29 (15 mg/kg), respectively on the drug pairing days. CPA was tested 24 hr following the last conditioning session and the animals were allowed to explore the apparatus for 15 min. CPA score was calculated as animals' time spent in drug-paired minus saline-paired compartments, Oxycodone HCl and naloxone HCl were purchased from Sigma Chemical Co. (Saint Louis, Mo., USA) and were dissolved in physiological saline.

All data are presented as means (=SEM), and were analyzed using one-way or two-way analysis of variance (ANOVA) with or without repeated measure when appropriate. Post-Hoc comparisons among groups were carried out using the Newman-Keuls test.

REFERENCES

Azar M R, Jones B C, Schulteis G (2003) Conditioned place aversion is a highly sensitive index of acute opioid dependence and withdrawal. Psychopharmacology (Berl) 170:42-50.

Olmstead M C, Burns L H (2005) Ultra-low-dose naltrexone suppresses rewarding effects of opiates and aversive effects of opiate withdrawal in rats. Psychopharmacology (Berl) 181:576-581.

Yu H, Wen D, Ma C, Meng Y, Li S, Ni Z, Cong B (2012) Effects of exogenous cholecystokinin octapeptide on acquisition of naloxone precipitated withdrawal induced conditioned place aversion in rats. PLoS One 7:e41860.

Xi Z X, Gilbert J, Campos A C, Kline N, Ashby C R Jr, Hagan J J, Heidbreder C A, Gardner E L (2004) Blockade of mesolimbic dopamine D3 receptors inhibits stress-induced reinstatement of cocaine-seeking in rats. Psychopharmacol (Berl) 176:57-65

Xi Z X, Gilbert J G, Pak A C, Ashby C R Jr, Heidbreder C A, Gardner E L (2005) Selective dopamine D3 receptor antagonism by SB-277011A attenuates cocaine reinforcement as assessed by progressive-ratio and variable-cost/variable-payoff fixed-ratio cocaine self-administration in rats. Eur J Neurosci 21:3427-3438

Figure 3A:
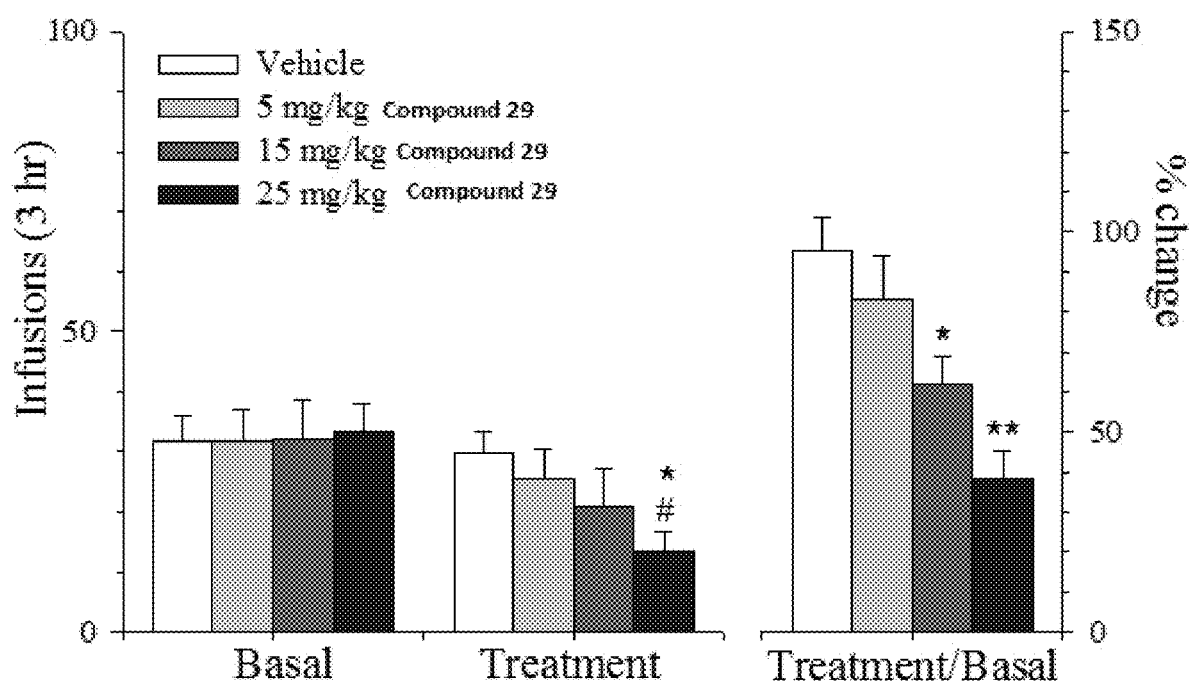
FIG. 3A illustrates the attenuating effects of systemic injection of compound (±)-29 (5-25 mg/kg, i.p.) on oxycodone taking (self-administration) in rats (N=6-7 in each group. #, P<0.05 versus basal drug taking levels; * and **, P<0.05 and 0.01, respectively, versus vehicle group).

FIG. 3A shows the effects of systemic injection of compound 29 (5-25 mg/kg, i.p.) on oxycodone taking (self-administration) in rats. Two-way ANOVA with repeated measure over session (raw data analysis) revealed a significant effect of group ($F_{(3,30)}$=5.54, P<0.01) but not of session ($F_{(1,10)}$=0.77, P=0.39) and Session×Group interaction ($F_{(3,30)}$=1.76, P=0.18). Analysis of the % changes with one-way ANOVA also revealed a significant effect (($F_{(3,30)}$=5.54, P<0.01). N=6 in each group. #, P, 0.05 versus basal drug taking levels; * and **, P<0.05 and 0.01, respectively, versus vehicle group.

Figure 3B:
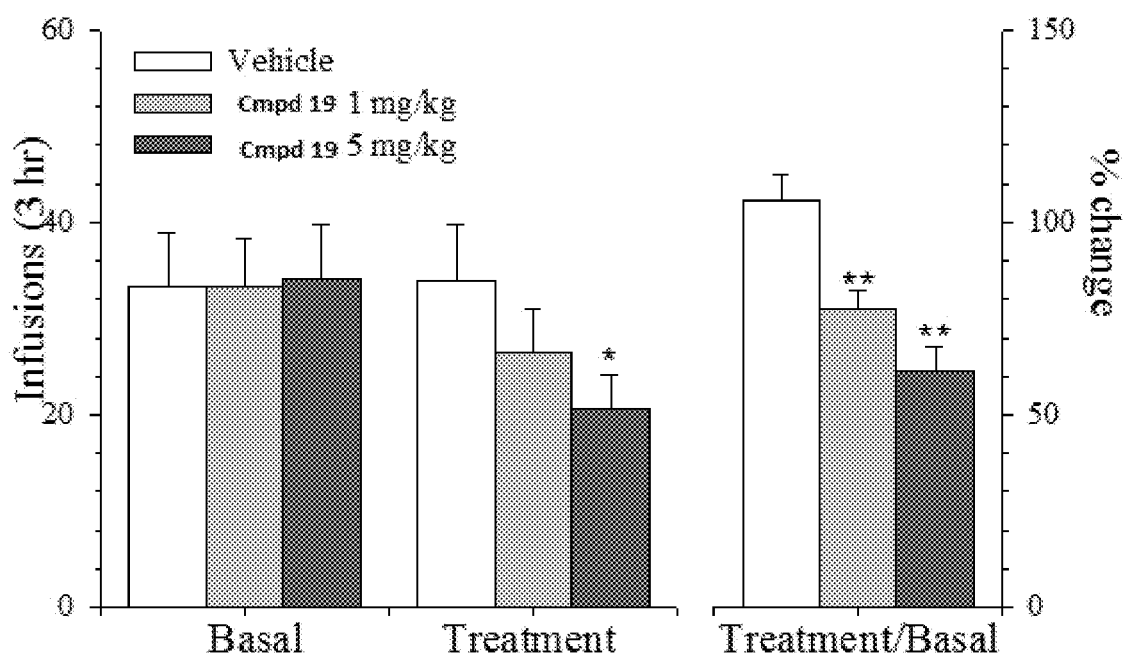
FIG. 3B illustrates the effects of systemic injection of compound (±)-19 (1-5 mg/kg, i.p.) on oxycodone taking (self-administration) in rats (N=6-7 in each group. #, P<0.05 versus basal drug taking levels; * and **, P<0.05 and 0.01, respectively, versus vehicle group)

FIG. 3B shows the effects of systemic injection of compound 19 (1-5 mg/kg, i.p.) on oxycodone taking (self-administration) in rats. N=6-7 in each group. #, P<0.05 versus basal drug taking levels; * and **, P<0.05 and 0.01, respectively, versus vehicle group.

Figure 4:
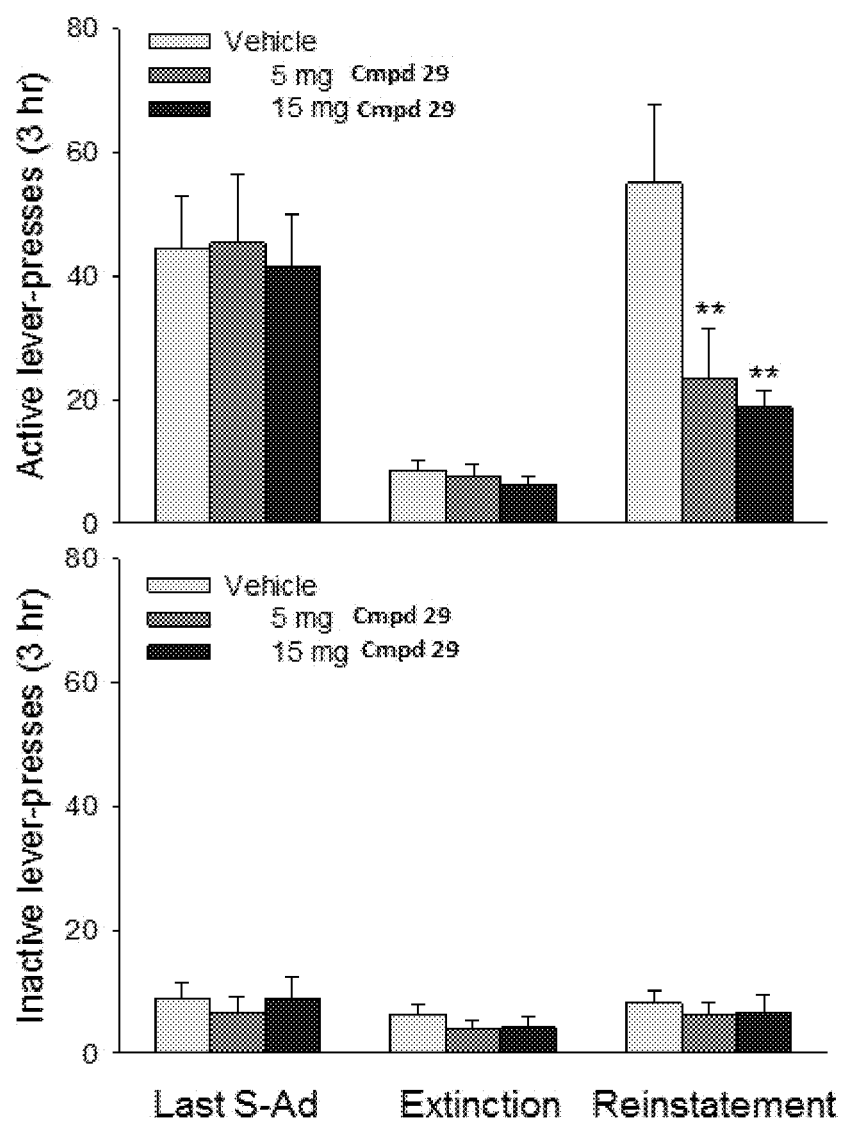
FIG. 4 illustrates the attenuating effects of systemic injection of compound (±)-29 on oxycodone-precipitated reinstatement of drug seeking in rats.

FIG. 4 shows the effects of systemic injection of compound 29 (5-15 mg/kg, i.p.) on reinstatement of oxycodone-seeking induced by priming injection of oxycodone (1 mg/kg, i.p.) in previously oxycodone self-administration trained and subsequently behaviorally extinguished rats. N=7-8 in each group. **, P<0.01 versus vehicle group.

Figure 5:
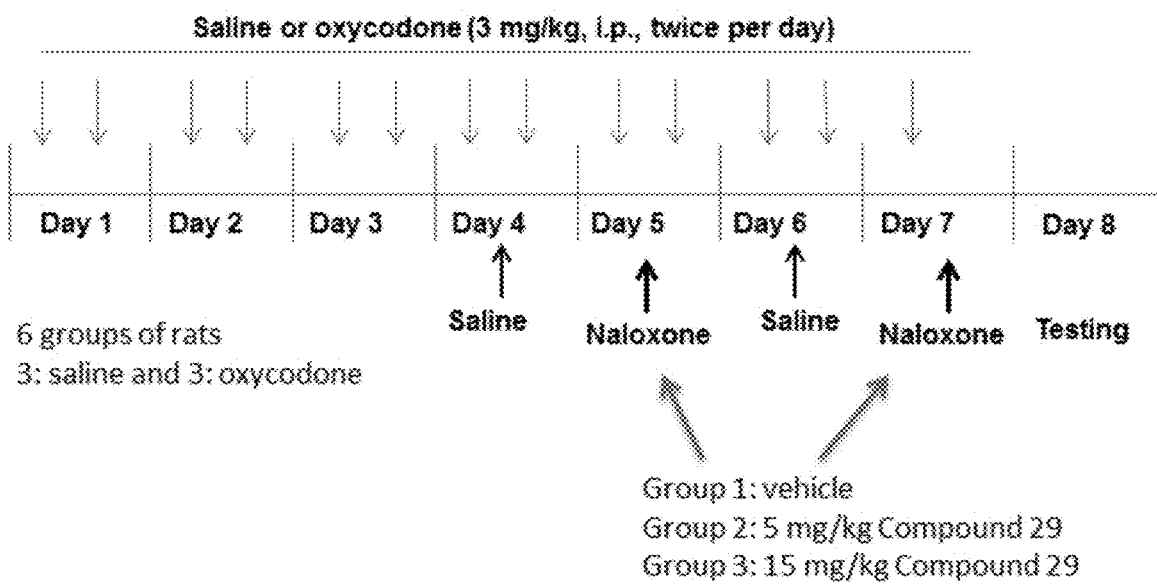
FIG. 5 describes the procedure for the naloxone-precipitated conditioned place aversion in chronic oxycodone treated rats.

FIG. 5 describes the procedure for the naloxone-precipitated conditioned place aversion in chronic oxycodone treated rats.

Figure 6:
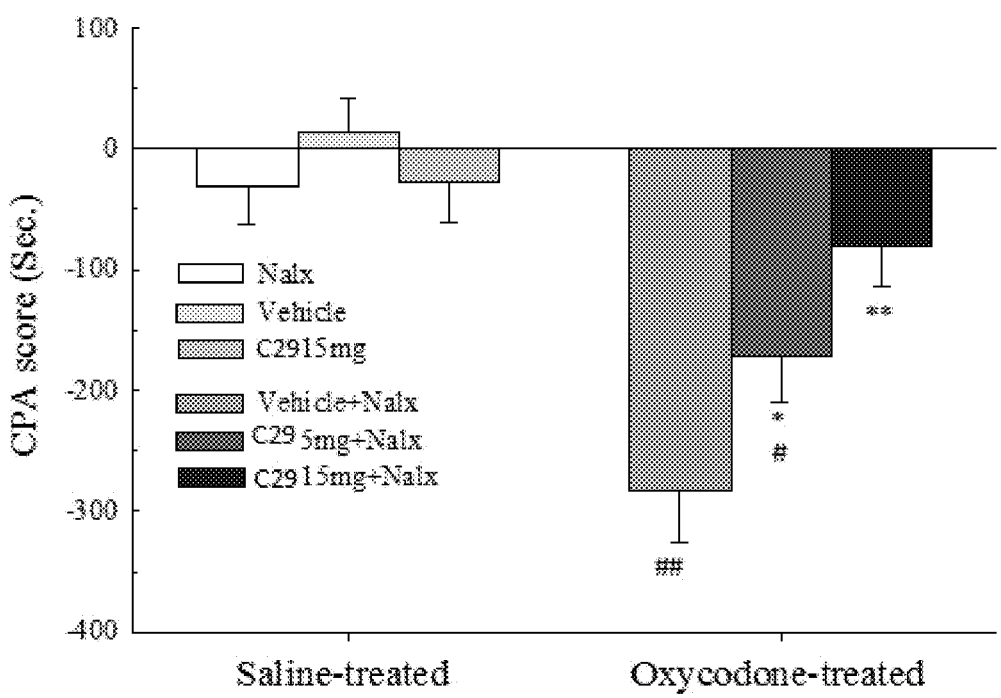
FIG. 6 illustrates the inhibition of naloxone-precipitated conditioned place aversion in chronic oxycodone-treated rats with compound (±)-29.

FIG. 6 illustrates the results where compound 29 (5, 15 mg/kg, 1 hour prior to naloxone) inhibits naloxone-precipitated conditioned place aversion in chronic oxycodone-treated rats. # and ##, P<0.05 and 0.01, versus saline-treated groups; * and **, P<0.05 and 0.01, versus Nalx+vehicle group, respectively. N=8 in each group.

Compound 29 was evaluated for its in vivo efficacy in rats self-administering of the prescription opioid analgesic, oxycodone. Under an FR1 schedule, compound 29 attenuated self-administration at 15 and 25 mg/kg (FIG. 3A), inhibited oxycodone seeking during extinction testing (FIG. 4), and blocked oxycodone-induced reinstatement to drug seeking. Compound 29 also significantly attenuated naloxone-precipitated conditioned place aversion in chronic oxycodone treated rats (FIG. 6). The results show that compound 29, a highly D3R-selective antagonist, is effective in these opiate abuse models. These data suggest that the $D_3R$ antagonists of Formula (I) may be suitable alternatives or adjunctive to opioid receptor mediated medications (e.g. buprenorphine, methadone or naloxone) currently used clinically in treating opiate addiction.

Compound 29 does not bind to opiate (mu, delta, kappa) receptors.

Pretreatment of either compound (±)-29 (15 mg/kg and 25 mg/kg) or compound (±)-19 (1 mg/kg and 5 mg/kg) showed no significant effects on sucrose self-administration.

Compound (±)-29 pretreatments (5-15 mg/kg i.p.) on acquisition of oxycodone self-administration (0.05 mg/kg/infusion; N=8 in each group) demonstrated that the animals self administered a significantly lower number of infusions of oxycodone when pretreated with 15 mg/kg compound (±)-29 and this effect persisted for several says after pretreatment.

Example 5. THC Self-Administration Studies in Squirrel Monkeys with Compound 29

Compound 29 was tested in a THC self-administration model in squirrel monkeys self-administering THC under an FR10 schedule.

Subjects: Seven adult male squirrel monkeys (*Saimiri sciureus*) weighing 0.8 to 1.1 kg were housed in individual cages in a temperature- and humidity-controlled room with unrestricted access to water. Each animal had a unique numeric or alphanumeric identifier (THC self-administering group: 434, 25B, 37B; food self-administering group: 1549, 570, 27B, 535). The monkeys were trained to self-administer either THC or food pellets prior to the study. Monkeys were fed (approximately two hours after the session) a daily food ration consisting of biscuits of high protein monkey diet (Lab Diet 5045, PMI Nutrition International, Richmond, Ind.). The number of biscuits (8-14) was determined for each monkey individually to maintain their body weights at a constant level throughout the study. Monkeys self-administering food pellets had the number of biscuits adjusted to maintain the motivation to perform a food-reinforced task. Fresh fruits, vegetables and environmental enrichment were provided daily. All animals used in this study were maintained in facilities fully accredited by the Association for the Assessment and Accreditation of Laboratory Animal Care, and experiments were conducted in accordance with guidelines of the Institutional Animal Care and Use Committee of the Intramural Research Program, National Institute of Drug Abuse, National Institutes of Health, and the Guidelines for the Care and Use of Mammals in Neuroscience and Behavioral Research (National Research Council 2003).

Monkeys were surgically prepared with chronic indwelling venous catheters (polyvinyl chloride; inside diameter, 0.38 mm; outside diameter 0.76 mm) (Goldberg 1973) which were passed subcutaneously to the monkey's back where they exited the skin. The monkeys wore nylon-mesh jackets (Lomir Biomedical, Canada) to protect their catheters.

Apparatus: Experimental chambers and other apparatus used in this study were the same as previously described (Justinova et al. 2003). Test sessions were conducted in sound-attenuating isolation chambers equipped with a Plexiglas chair, a white house light and white noise for masking of external sound. The chair contained one response lever (Med Associates., USA) mounted on a transparent front wall; each press on the lever with a force greater than 0.2 N produced an audible click and was recorded as a response. Pair of amber stimulus lights, mounted behind the transparent wall of the chair, could be illuminated and used as visual stimuli.

Self-administration procedure: Daily one-hour experimental sessions were typically conducted from Monday through Friday with each monkey. Each session, monkeys were placed into Plexiglas chairs and restrained in the seated position by waist locks. Before the start of the session, catheters were flushed with 1 ml of saline and one injection was delivered (calculated to fill the dead space of the catheter which was about 0.2 ml). The monkeys' catheters were connected to polyethylene tubing, which passed out of the isolation chambers where they attached to motor-driven syringe pumps. The syringe pumps were calibrated so that duration of each injection was 0.2 s and injection volume was 0.2 ml. At the start of the session, a white house light was turned off and a green stimulus light was turned on. In the presence of the green light, monkeys were required to make 10 responses on the lever (10-response, fixed-ratio schedule of reinforcement; FR10) to produce an injection of THC. The completion of 10 responses on the lever turned off the green light and produced an intravenous (i.v.) injection of 4 μg/kg of THC. Each injection was paired with a 2-s illumination of an amber stimulus light. Each injection was followed by a 60-s timeout period, during which the chamber was dark and lever presses had no programmed consequences.

Self-administration study: When responding for the training dose of THC (4 mg/kg/injection), was stable for at least five consecutive sessions (less than 15% variability), testing with the selective D3 antagonist Compound 29 was then conducted. After 3 sessions with vehicle pretreatment, pretreatment with each Compound 29 dose (1, 3, and 10 mg/kg, i.m.) was tested for three consecutive sessions, followed by recovery of THC baseline responding. The same schedule of reinforcement and experimental protocol was also used in a group of monkeys self-administering food pellets.

Reinstatement studies: In order to separately determine the reinstatement effects of a priming injection and drug-associated cues, we use two different extinction protocols (described below) that allow us to isolate the effects of these independent variables.

Priming-induced reinstatement: Before priming-induced reinstatement testing began, monkeys were allowed to self-administer the training dose of THC until they reached a stable baseline (5-10 sessions). In subsequent extinction sessions, lever presses led to i.v. saline infusions plus the visual cues that had been associated previously with THC. After at least two sessions of extinction, when responding had reached a low, stable level, a priming injection of THC (0.04 mg/kg i.v.) was given immediately before the next session, during which responding (FR10) continued to produce only i.v. saline injections and the discrete visual cues. The effects of Compound 29 (1, 3, and 10 mg/kg, i.m.) or vehicle were studied as pretreatments given prior to the THC priming sessions. A non-contingent i.v. injection of vehicle was also given before each extinction session as a control for the drug priming treatment. The 10.0 mg/kg dose of Compound 29 was also given i.m. prior to vehicle priming to determine whether Compound 29 alone would affect extinguished drug seeking. The THC priming-induced reinstatement with vehicle pretreatment was repeated after the conclusion of Compound 29 testing to ascertain the reliability of the reinstatement effect over repeated tests.

Cue-induced reinstatement: After the completion of priming-induced reinstatement testing, the monkeys were returned to baseline THC self-administration for 5-10 sessions. In subsequent extinction sessions, drug injections and all cues associated with drug injections were removed. This means that catheters were not connected to a pump and monkeys were not receiving infusions or visual cue presentations. After two or three days of extinction, we tested for cue-induced reinstatement of extinguished drug-seeking behavior after vehicle pretreatment (i.m.) by allowing delivery of a saline injection paired with the drug-associated cues. Then, the effect of pretreatment with Compound 29 (0.3. 1, and 3 mg/kg) on cue-induced reinstatement was studied. Each reinstatement test was a single session, which was preceded and followed by extinction session(s) with vehicle pretreatment (i.m.) 30 min before the sessions. Compound 29 (3 mg/kg) was also given i.m. prior to an extinction session to study the effects of Compound 29 on extinguished drug seeking. The cue-induced reinstatement with vehicle pretreatment was repeated after the conclusion of Compound 29 testing to ascertain the reliability of the reinstatement effect over repeated tests.

$\Delta^9$-tetrahydrocannabinol (THC, NIDA Drug Supply Program, Bethesda, Md., USA) was dissolved in a vehicle containing 1% Tween 80, 1% ethanol, and saline to obtain stock solution (0.4 mg/ml) and further diluted with saline. In the reinstatement tests, THC was injected i.v. (1 ml/kg) immediately before the session. Compound 29 was dissolved in a vehicle containing 15% DMSO, 10% cyclodextrin in saline and injected i.m. (0.33 ml/kg) 30 min before the session.

Data analysis: The number of reinforcements (injections or pellets) per session represents total number of injections delivered during each 1-hour session. The rates of responding are expressed as responses per second averaged over the 1 h session, with time and responding during time-outs not included in calculations. Data are expressed as mean response rates and numbers of reinforcements per session±SEM. For statistical evaluation of effects over consecutive sessions, the average of the last three sessions prior to the experimental manipulation was used as a control value to allow comparisons with subsequent sessions. Statistical analysis was performed using one-way or two-way repeated measures ANOVA (data met the assumptions of the test). Post hoc analysis was performed either by Tukey pairwise multiple comparisons or Bonferroni t-test (multiple comparisons versus control group). Statistical significance was accepted at the p<0.05 level. SigmaStat software (Systat Software Inc.) was used for all statistical analyses.

References (methods): Goldberg S R (1973) Comparable behavior maintained under fixed-ratio and second-order schedules of food presentation, cocaine injection or d-amphetamine injection in the squirrel monkey. J Pharmacol Exp Ther 186:18-30.

Justinova Z, Tanda G, Redhi G H, Goldberg S R (2003) Self-administration of delta9-tetrahydrocannabinol (THC) by drug naive squirrel monkeys. Psychopharmacology (Berl) 169:135-140.

Figure 7:
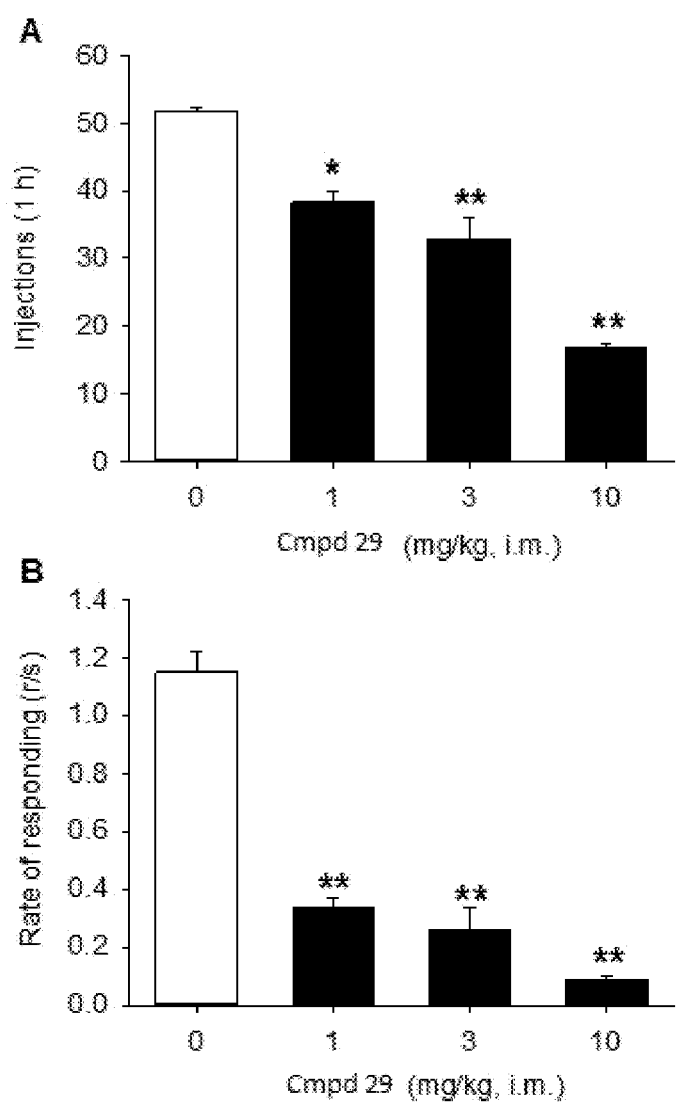
FIG. 7 illustrates the attenuation of THC self-administration in squirrel monkeys with the administration of compound (±)-29.

FIG. 7, graphs A and B exhibit results establishing that compound 29 attenuates THC self-administration in squirrel monkeys when administered intramuscularly at 1, 3, and 10 mg/kg.

Figure 8:
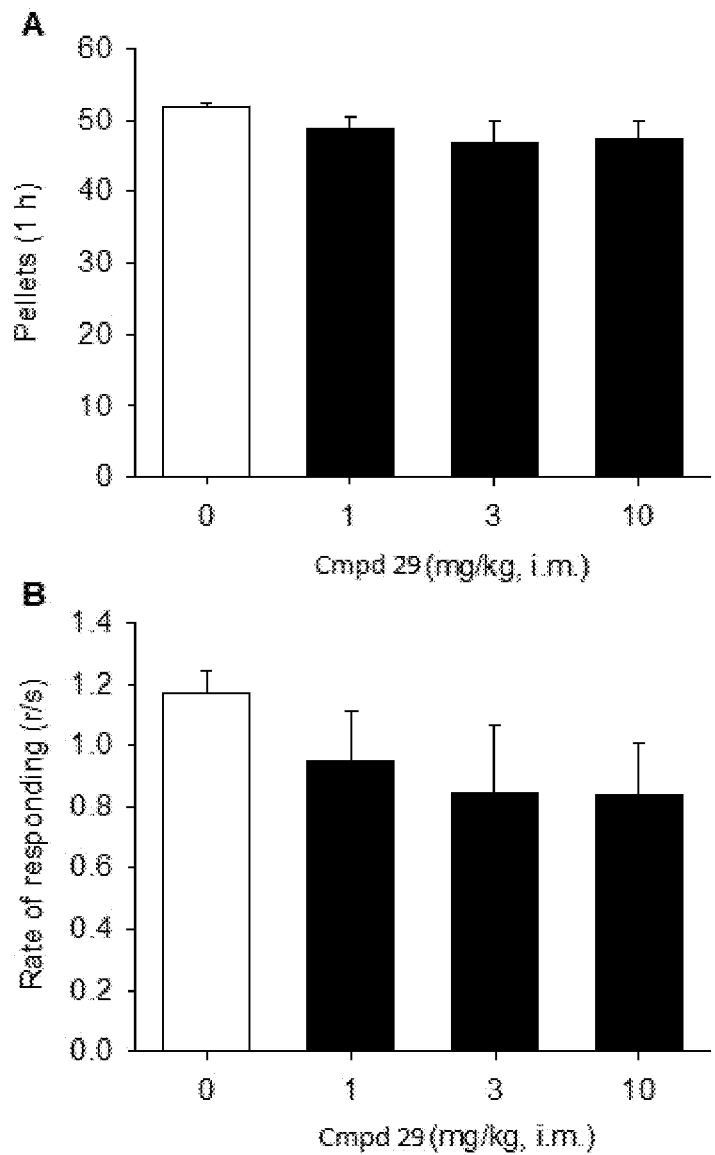
FIG. 8 illustrates compound (±)-29 has no effect on food self-administration in squirrel monkeys.

FIG. 8, graphs A and B exhibit results establishing that compound 29 has no effect on food self-administration in squirrel monkeys when administered intramuscularly at 1, 3, and 10 mg/kg.

Figure 9:
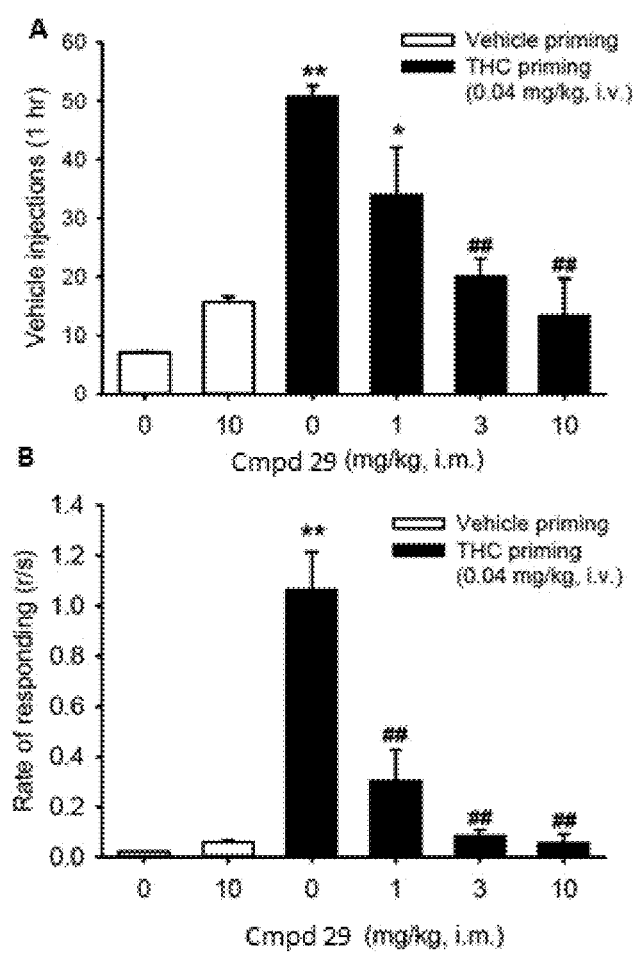
FIG. 9 illustrates the attenuation of THC-induced reinstatement to drug seeking in squirrel monkeys with the administration of compound (±)-29.

FIG. 9, graphs A and B exhibit results establishing that compound 29 attenuates THC-induced reinstatement to drug seeking in squirrel monkeys when administered intramuscularly at 1, 3, and 10 mg/kg.

Compound 29 does not bind to cannabinoid CB1 or CB2 receptors.

The results show that compound 29, a highly D3R-selective antagonist, is effective in a THC abuse model. Compound 29 dose-dependently blocked THC self-administration (4 µg/kg/inf) in the 1-10 mg/kg range without affecting food self-administration. In addition, compound 29 in the same dose range, blocked THC-induced reinstatement of drug seeking in these animals suggesting that D3R antagonists of Formula (I) may be useful in treating marijuana abuse.

Compound (±)-29 attenuated cue-induced reinstatement of drug seeking behavior in squirrel monkeys.

Tables 2 and 3 provide additional functional data for selected compounds of Formula (I).

TABLE 2

Functional data for selected compounds of Formula (I) using stimulation or inhibition of quinpirole-stimulated mitogenesis in CHO cells with human dopamine D3R[a]

| | $D_3R$ mitogenesis assay | | |
|---|---|---|---|
| Compd | Agonist $EC_{50}$ ± SEM, nM | % Stimulation | Antagonist $IC_{50}$ ± SEM, nM |
| 18 | 4.70 ± 0.57 | 42.3 | 19.1 ± 3.5 |
| 19 | 2.58 ± 0.87 | 17.9 | 50.5 ± 7.2 |
| 20 | 410 ± 130 | 31.2 | 18.5 ± 6.3 |
| 21 | 196 ± 64 | 22.3 | 230 ± 27 |
| 28 | >8300 | 5.8 | 330 ± 100 |
| 29 | >8300 | 6.7 | 360 ± 100 |
| 30 | >6600 | 4.9 | 420 ± 130 |
| 31 | >7100 | 3.6 | 950 ± 350 |

[a]Data were obtained through the NIDA Addiction Treatment Discovery Program contract (ADA151001) with Oregon Health & Science University.
[b] ND = Not determined; Functional assays for each receptor was not conducted if the $K_i$ value for the binding assay is >500 nM for DA receptors.

TABLE 3

Additional in vitro binding and functional data for selected compounds of Formula (I) at $5HT_{1A}$, $5HT_{2A}$ and $5HT_{2C}$ receptors[a]

| Compd | 5-$HT_{1A}$ [$^3$H]-8-OH-DPAT $K_i \pm$ SEM, nM | 5-$HT_{2A}$ [$^{125}$I]DOI $K_i \pm$ SEM, nM | 5-$HT_{2C}$ [$^{125}$I]DOI $K_i \pm$ SEM, nM | 5$HT_{1A}$ [$^{35}$S]GTPγS binding Agonist $EC_{50} \pm$ SEM, nM | % Stimulation |
|---|---|---|---|---|---|
| 18 | 59 ± 13 | 5.22 ± 0.98 | 18.3 ± 2.2 | 149 ± 47 | 94.3 |
| 19 | 880 ± 160 | 28.1 ± 9.7 | 113 ± 33 | ND[b] | — |
| 20 | 26.0 ± 8.1 | 2.41 ± 0.82 | 18.7 ± 4.5 | 31 ± 10 | 99.4 |
| 21 | 27.6 ± 5.3 | 3.2 ± 1.1 | 89 ± 22 | 118 ± 39 | 101.1 |
| 28 | 2330 ± 700 | 60.1 ± 9.5 | 144 ± 37 | ND[b] | — |
| 29 | >7600 | 188 ± 22 | 2190 ± 460 | ND[b] | — |
| 30 | 560 ± 170 | 25.0 ± 6.6 | 55 ± 17 | ND[b] | — |
| 31 | 2410 ± 830 | 42.9 ± 6.8 | 268 ± 34 | ND[b] | — |

[a]Data were obtained through the NIDA Addiction Treatment Discovery Program contract (ADA151001) with Oregon Health & Science University. [b]ND = Not determined; Functional assays for each receptor was not conducted if the $K_i$ value for the binding assay was >250 nM for 5-HT receptors.

Example 6. Oxycodone-Induced Conditioned Place Preference (CPP) Study in Rats

Fifty male Long-Evans rats (275-300 g) were purchased from the Charles River Laboratories (Raleigh, N.C.) and housed in the animal facility at NIDA IRP under a reversed 12 h light-dark cycle (light on at 7:00 PM) with free access to food and water. All procedures were in accordance with the "Principles of Laboratory Animal Care" outlined by National Institute of Health (NIH publication 86-23, 1996).

Figure 10:
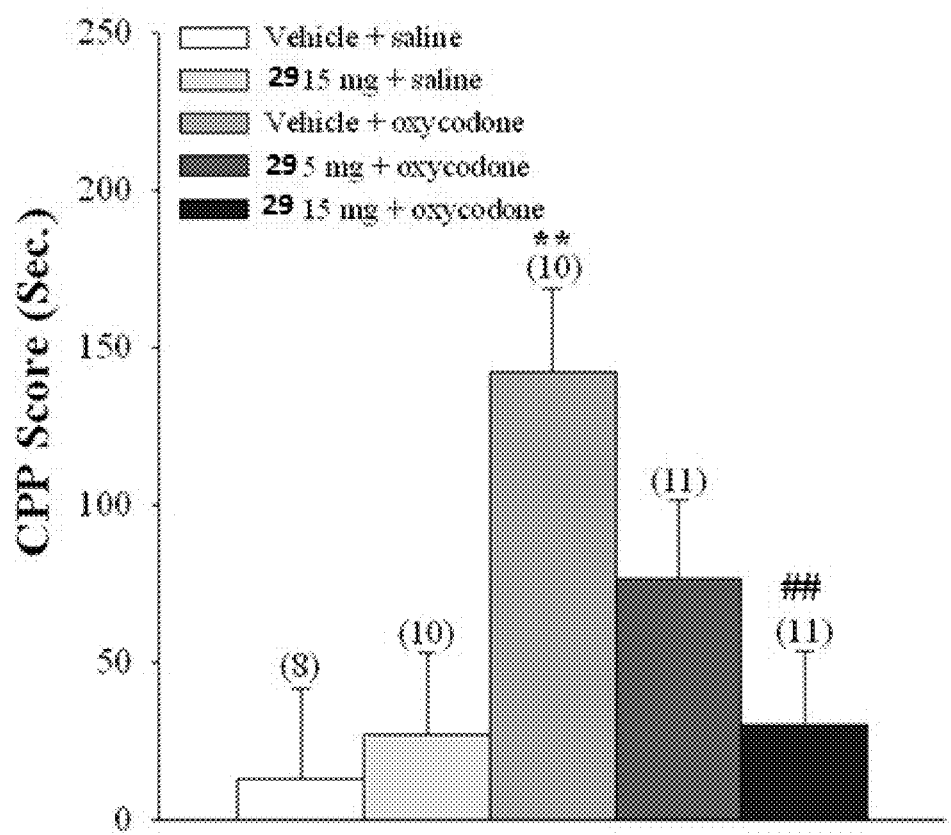
FIG. 10 illustrates the effects of compound (±)-29 on oxycodone-induced conditioned place preference in rats.

CPP was tested in the place-conditioning apparatus (Med Associates, St Albans, Vt.) consisting of two side compartments (21×28 cm$^2$) and a central gray connecting area (21×12.5 cm$^2$); a sliding door separated each compartment from the connecting area. The two side compartments differed in wall color (black vs white), floor type (net vs grid), and illumination. The animals were then divided randomly into five treatment groups as shown in FIG. 10 legend. Each rat was first exposed in the CPP apparatus for 15 minutes (preconditioning) and then followed by oxycodone CPP conditioning. Animals displayed significant bias in one compartment (defined by the time difference between two compartments ≥200 s) during preconditioning were excluded from the study. Oxycodone CPP procedures consisted of 2 days of oxycodone (3 mg/kg, ip) conditioning in one compartment and 2 days of saline conditioning in another compartment, alternatively (e.g., oxycodone-saline-oxycodone-saline). The compartments paired with oxycodone or saline were counterbalanced. On the conditioning days, each animal received saline or compound 29 (5, 15 mg/kg, ip) pretreatment 15 minutes prior to oxycodone injection. After oxycodone injection, animals were immediately confined in the assigned compartments for 40 minutes. To potentiate oxycodone CPP formation, animals received 4 days of oxycodone (3 mg/kg, ip, twice daily at 8:00 and 18:00) treatment at home cages. In the (29+vehicle) group, saline was paired with one compartment and compound 29 (15 mg/kg) was paired with another compartment. In the (Vehicle+vehicle) group, saline was paired with each compartment. Then 24 hours after the last saline or oxycodone conditioning injection, animals were placed in the same three-chamber CPP apparatus for 15 minutes and the time spent in each compartment was recorded. The CPP score was calculated by the time difference (seconds) that animalspent in drug-paired compartment versus saline-paired compartment.

FIG. 10 shows the effects of compound 29 on oxycodone-induced CPP. Four days of oxycodone (e.g., Vehicle+oxycodone group) (3 mg/kg, ip) versus saline conditioning produced significant CPP compared to the (Vehicle+saline) control group of rats. Pretreatment with compound 29 (5, 15 mg/kg, ip, 15 min before each oxycodone injection) dose-dependently attenuated oxycodone-induced CPP (FIG. 10). One-way ANOVA revealed a statistically significant treatment main effect ($F_{4,45}$=4.29, p<0.01). Posthoc individual group comparisons indicated a significant reduction in oxycodone induced CPP after 15 mg/kg compound 29 (p<0.05) compared to (Vehicle+oxycodone) group. Compound 29 alone, at 15 mg/kg, did not produce CPP, suggesting a lack of reward by itself. In FIG. 10, **p<0.01, compared to the (Vehicle+vehicle) group; ##p<0.01, compared to the (Vehicle+oxycodone) group; the number on each bar shows the animal number in eachexperimental group.

Example 7. Locomotor Activity Studies in Mice

Like other opioid agonists such as morphine or heroin, acute (or single dose) administration of oxycodone produces a significant increase in locomotor activity in mice. Moreover, repeated administration of these opioid agonists produces a progressive increase in locomotion over time, i.e., locomotor sensitization. This study was directed to (1) determine if compound 29 alone had any effect on basal locomotor activity, (2) if it would attenuate oxycodone-stimulated locomotor activity and sensitization, and (3) if this effect was long-lasting. Twenty-four male mice (22-25 g) with a C57BL/6J genetic background were purchased from the Charles River Laboratories (Raleigh, N.C.). After arrival, they were group housed in the animal facility under a reversed 12 h light-dark cycle (light on at 7:00 PM) with free access to food and water and allowed to acclimate to the new environment for 7 days prior to initiating the experiment. All procedures were in accordance with the "Principles of Laboratory Animal Care" outlined by National Institute of Health (NIH publication 86-23, 1996).

Locomotor activity tests were conducted in open-field chambers (43×43×30 cm$^3$) (Accuscan Instruments, Inc., Columbus, Ohio, USA). Before testing, the mice were habituated to the locomotor chamber (2 h/day for 3 consecutive days) and then were randomly divided into three dose groups (vehicle, 5, 15 mg/kg compound 29). On habituation days, the animals were moved to the test room, acclimated there for 10 min, and then placed in their assigned locomotor chambers. On test day 1, each group of mice was pretreated with either vehicle (25% of 2-hydroxy-propyl-β-cyclodextrin) or one dose of compound 29 (5, 15 mg/kg, ip) without an oxycodone injection. Then 15 min later, the animals were placed into the test chambers. Their locomotor activities were recorded every 20 min for 2 h using VersaMax version 3.0 software (Accuscan Instruments, Inc.). On test days 2-6, the three groups of mice first received vehicle or one dose of compound 29, followed by an oxycodone injection 15 min after compound 29 pretreatment. After 72 h of withdrawal in the home cages in the animal facility, each animal was challenged with a 4 mg/kg oxycodone injection again (day 9) but without compound 29 pretreatment. The locomotor activities were recorded for 2 h/day after each oxycodone injection. The locomotor behavioral data are expressed as means (±SEM). The traveled distance (cm) within 2 h (FIG. 11 graph A) or every 20 min (FIGS. 11B-D) was used to evaluate the locomotor effects of 29 and/or oxycodone in mice. Two-way ANOVA with repeated measures over time was used to evaluate the statistical significance of the changes in locomotor activity after compound 29 and/or oxycodone administration. Post-hoc Fisher's least significant difference was used for multiple comparisons. p<0.05 was considered statistically significant.

Figure 11:
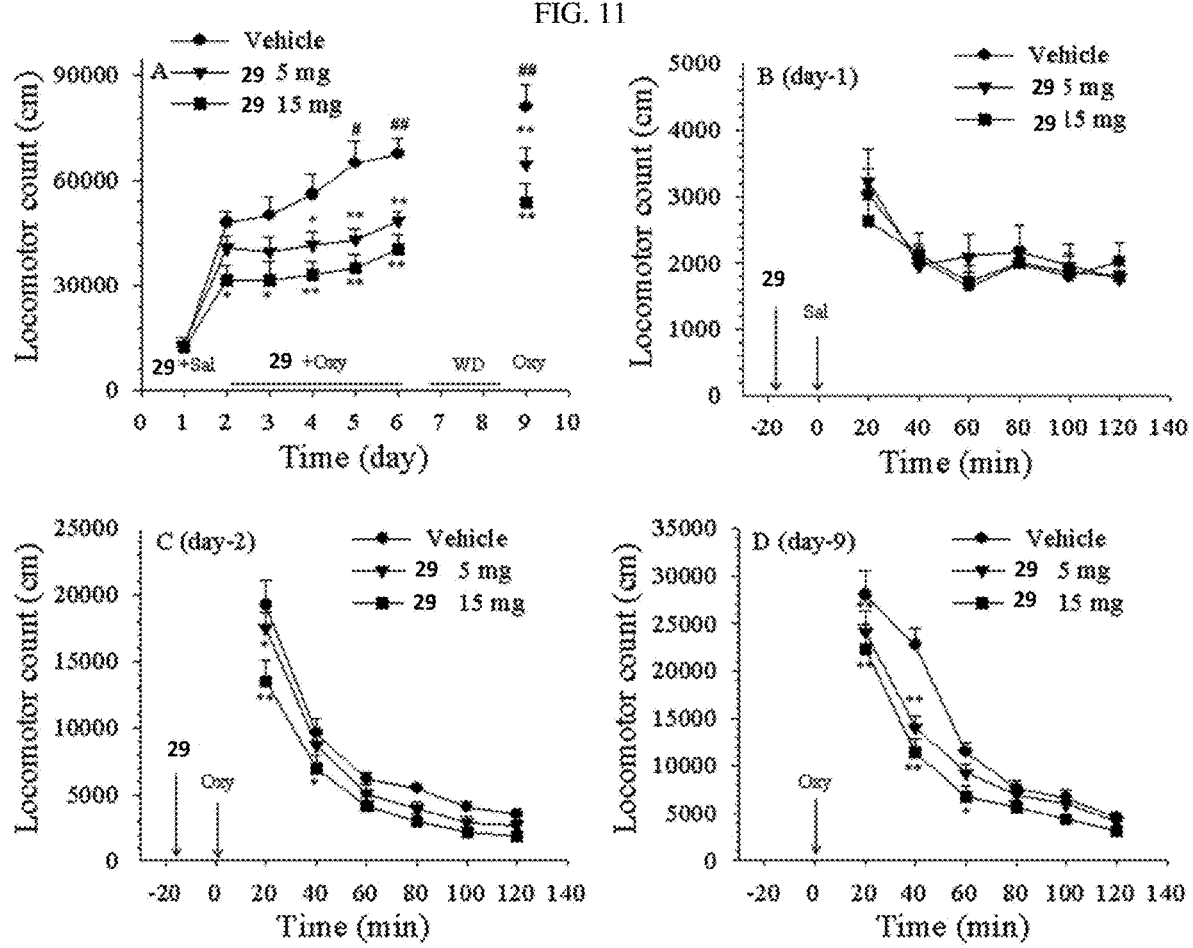
FIG. 11 illustrates the effects of compound (±)-29 (0, 5, 15 mg/kg, ip) on basal and oxycodone-induced increases in locomotor activity in mice.

FIG. 11 graphs A-D illustrate the effects of compound 29 (0, 5, 15 mg/kg, ip) on basal and oxycodone-induced increases in locomotor activity in mice. FIG. 11 graph A shows the effects of oxycodone on locomotion over time (from day 2 to day 9) in the presence or absence of compound 29 treatment. On day 1, compound 29 alone (5, 15 mg/kg, 15 min before saline) was administered and had no effect on locomotion. From day 2 to day 6, each animal received one daily dose of 29 (vehicle, 5, 15 mg/kg, 15 min prior to oxycodone) and oxycodone (4 mg/kg) administration. In the vehicle treatment group, repeated daily administration of oxycodone produced a progressive increase in locomotion (i.e., locomotor sensitization) (#$p<0.05$, ##$p<0.01$, compared to the level of locomotor activity on day 2). This locomotor sensitization was dose-dependently blocked by 29 (*$p<0.05$, **$p<0.01$, compared to the vehicle control group at each time point labeled). After 5 days of the (vehicle/29+oxycodone) coadministration, animals underwent 2 days of withdrawal, followed by a 4 mg/kg oxycodone challenge injection (without 29 pretreatment) on day 9, indicating that oxycodone-induced locomotor sensitization was still present in the vehicle control group, which was blocked in the 29 pretreatment groups. FIG. 11 graph B shows a time course of 29-induced changes in locomotion (day 1), indicating that it has no effect on locomotor activity by itself. FIG. 11 graph C shows a time course of oxycodone-induced changes in locomotion after the first injection of oxycodone (acute effect on day 2), indicating that 29 pretreatment dose-dependently inhibited oxycodone-induced hyperactivity (acute effect). FIG. 11 graph D shows a time course of oxycodone priming-induced changes in locomotion in mice after 2 days of withdrawal from the last (vehicle/29+oxycodone) coadministration (day 9), indicating that repeated 29 pretreatment from day 2 to day 6 produced a long-lasting inhibition in oxycodone-induced increases in locomotion. N=8 mice in each group.

The results of this evaluation are shown in FIG. 11, graphs A-D. FIG. 11 graph A shows the overall locomotor effects of repeated, daily administration of oxycodone (4 mg/kg, ip) in the presence of vehicle (25% β-cyclodextrin) or one dose of compound 29 (5, 15 mg/kg, ip administered 15 min before oxycodone injection). Compound 29 alone had no effect on basal locomotor activity in mice when tested on day 1 (FIG. 11 graphs A,B). In contrast, oxycodone caused significant increases in locomotor activity (FIG. 11 graphs A,C). Repeated oxycodone administration produced a progressive increase in locomotion (sensitization) over time (from day 2 to day 6 in the vehicle pretreatment group). Strikingly, pretreatment with compound 29 not only attenuated acute oxycodone-induced hyperactivity (FIG. 11 graph A, day 2) but also blocked the acquisition of repeated oxycodone-induced locomotor sensitization (FIG. 11 graph A, day 2-day 6) and the expression of oxycodone prime-induced locomotor sensitization after 2 days of withdrawal (FIG. 11 graph A, day 9). Two-way ANOVA for repeated measures over time (FIG. 11 graph A) revealed a statistically significant drug treatment main effect ($F_{2,21}=12.24$, $p<0.001$), time main effect ($F_{6, 49}=9.14$, $p<0.001$), and treatment x time interaction ($F_{12, 98}=31.51$, $p<0.001$). FIG. 11 graphs B-D show the time courses of oxycodone-induced change in locomotor activity when tested on day 1 (FIG. 11 graph B: $F_{2,21}=0.12$, $p=0.88$), day 2 (FIG. 11 graph C: $F_{2,21}=5.22$, $p<0.05$) and day 9 (FIG. 11 graph D: $F_{2,21}=5.95$, $p<0.01$), indicating that compound 29 pretreatment significantly attenuated oxycodone-induced increases in locomotion on each test day.

Example 8. Methods for Pharmcokinetics Study of Novel Dopamine D3 Receptor Antagonists in Rats Male Long-Evans rats with body weights ~250 grams (Charles River Laboratories, Raleigh, N.C., USA) were used in this study. All rats were housed individually in a climate-controlled room under a 12 h light/dark cycle. Food and water were available ad libitum throughout the experiments. All experimental procedures were conducted in accordance with the Guide for the Care and Use of Laboratory Animals and were approved by the Animal Care and Use Committee of the National Institute on Drug Abuse of the U.S. National Institutes of Health.

Experimental (oral gavage) procedures: The animals were gently restrained (grasp the animal by the loose skin of the neck and back) to immobilize the head but not such that the animals vocalize or show other signs of distress. Maintained the animal in an upright (vertical) position and passed the gavage needle (19-gauge) along the side of the mouth. Following the roof of the mouth, advanced the needle into the esophagus and toward the stomach. After the needle was passed to the correct length, the compound was injected. Then, the animals were deeply anesthetized with 100 mg/kg pentobarbital (i.p.), and then blood (~1 ml) was obtained via cardiac puncture and brain was dissected at different time points (15 min, 30 min, 60 min, 2 h, 4 h, and 8 h, n=3 rats per time point) after oral drug administration. Three additional rats received the vehicle (25% beta-hydroxy-cyclo-dextrin) as a "0 min" time point controls (i.e., baseline before the drug injection, in which the drug levels in the samples should be zero).

Sample analysis method; Preparation of standard and internal standard (IS) stock solution: Test compounds (R- and S-29 and R- and S-19) were dissolved in appropriate amount of DMSO to yield a 10 mM stock solution. These solutions were stored at −20° C. Losartan (IS) was dissolved in DMSO at 10 mM concentration that was further diluted in acetonitrile to obtain a final concentration of 500 nM and the solutions were stored at −20° C.

Standard Curve and Quality Control (QC) Sample Preparation: Standard curve plasma samples were prepared using naïve rat plasma, by serial dilution of the stock solution, with 8 standards and 4 QCs, ranging from 10-50,000 pmol/mL.

Standard curve brain samples were prepared using naïve rat brain. The tissue was homogenized in acetonitrile (Dilution Factor; DF=3), crushed, and centrifuged at 10,000 rpm for 10 minutes. The resulting supernatant was used as the standard curve matrix. The standard curve was subsequently prepared by serial dilution of the stock solution, with 7 standards and 4 QCs, ranging from 30-50000 pmol/mL.

Extraction Procedure: Test compounds were extracted from plasma samples by protein precipitation using acetonitrile. Compounds were extracted from brain samples by placing weighed tissue into 2 times w/v of acetonitrile (DF=3), crushed, centrifuged at 10,000 rpm for 10 minutes, and the resultant supernatant was used as the sample solution. Briefly standards, QCs, and samples (25 μL) were mixed with 100 μL acetonitrile containing 0.5 μM Losartan (internal standard; IS) in low retention microcentrifuge tubes. The mixture was vortexed for 1 min and centrifuged at 10,000 rpm for 10 min at 5° C. 50 μL of supernatant was transferred to a 250 μL polypropylene autosampler vials and mixed with 50 µL water, and sealed with a Teflon cap. A volume of 3 µL was injected onto the ultra-performance liquid chromatography (UPLC) instrument for quantitative analysis using a temperature-controlled autosampler operating at 10° C.

Chromatographic and Mass Spectrometric Conditions

LC Conditions

UHPLC System: Accela pump 1250 and Accela open-arm autosampler AS
Column: Eclipse Plus C18 RRHD 1.8 um, 2.1×100 mm
Flow rate: 0.4 mL/min
Mobile Phase A: 0.1% FA in ACN, Phase B: 0.1% FA in water.

LC Gradient Condition

| Time (min) | Phase A(%) | Phase B(%) |
|---|---|---|
| 0.01 | 10 | 90 |
| 0.20 | 10 | 90 |
| 2.00 | 99 | 1 |
| 2.50 | 99 | 1 |
| 2.70 | 10 | 90 |
| 5.00 | 10 | 90 |

MS Condition

| Ionization Mode | ESI, MRM(+) | | | |
|---|---|---|---|---|
| Compound | Q1 | Q3 | CE | S-Lens |
| 29 | 485.146 | 143.930, 213.003 | 34, 23 | 139 |
| 19 | 454.827 | 143.864 | 31 | 127 |
| Losartan | 423.200 | 180.088, 207.107 | 35, 22 | 99 |

The mass spectrometer was operated with an ESI interface in positive ionization mode for all compounds tested and controlled by the Xcalibur software 2.3 (Thermo Scientific). Samples were introduced to the interface through Turbo Ion Spray with the capillary temperature setting at 350° C. Nitrogen was used as the sheath and auxiliary gas, and argon as a collision gas with the settings of 40, 5 and 1.4, respectively. Quantification was performed in multiple-reaction monitoring (MRM) mode.

Chromatographic analysis was performed using an Accela™ ultra high-performance system consisting of an analytical pump, and an autosampler coupled with TSQ Vantage mass spectrometer (Thermo Fisher Scientific Inc., Waltham Mass.). Separation of the analyte from potentially interfering material was achieved at ambient temperature using Agilent Eclipse Plus column (100×2.1 mm i.d.) packed with a 1.8 µm $C_{18}$ stationary phase. The mobile phase used was composed of 0.1% Formic Acid (FA) in Acetonitrile (ACN) and 0.1% Formic Acid in $H_2O$ with gradient elution, starting with 10% organic linearly increasing to 99% at 2 min, maintaining at 99% (2-2.5 min), re-equilibrating to 10% by 2.7 min and maintaining 10% organic until the end of the run. The total run time for each analyte was 5.00 min.

Calibration curves for all test compounds were computed using the ratio of the peak area of analyte to the internal standard by using a quadratic regression with 1/x weighting. The parameters of each calibration curve were used to back-calculate concentrations and to obtain values for the QC samples and unknown samples by interpolation.

Figure 12A:
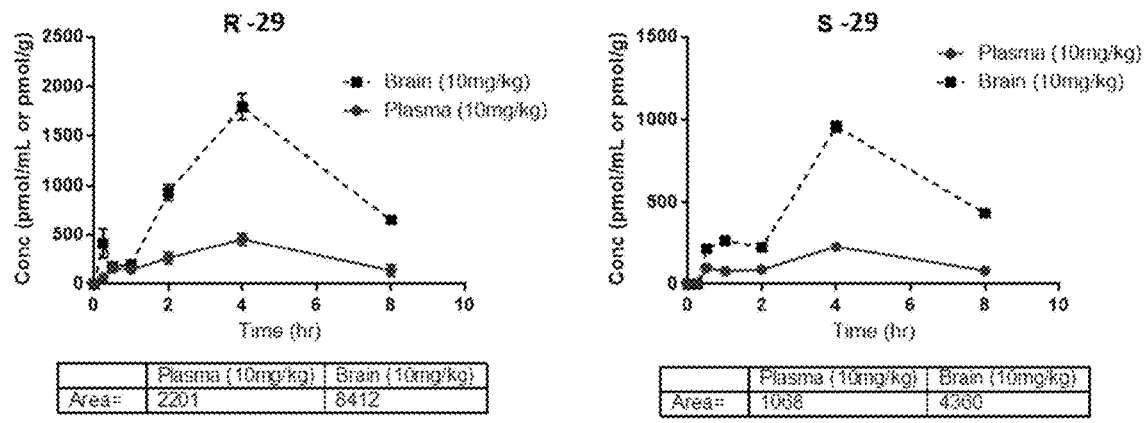
FIGS. 12A and 12B: Pharmacokinetic studies on R- and S-29 (FIG. 12A) and R- and S-19 (FIG. 12B) in Long Evans rats after oral administration of 10 mg/kg demonstrating that all four enantiomers are highly brain penetrable.

FIG. 12A discloses the rat pharmacokinetic results for each enantiomer of compound 29 orally administered at 10 mg/kg. Both enantiomers are orally available and brain penetrable. R-29 at the same dose showed twice higher exposures in both brain and plasma but the brain to plasma ratio was similar for both enantiomers.

Figure 12B:
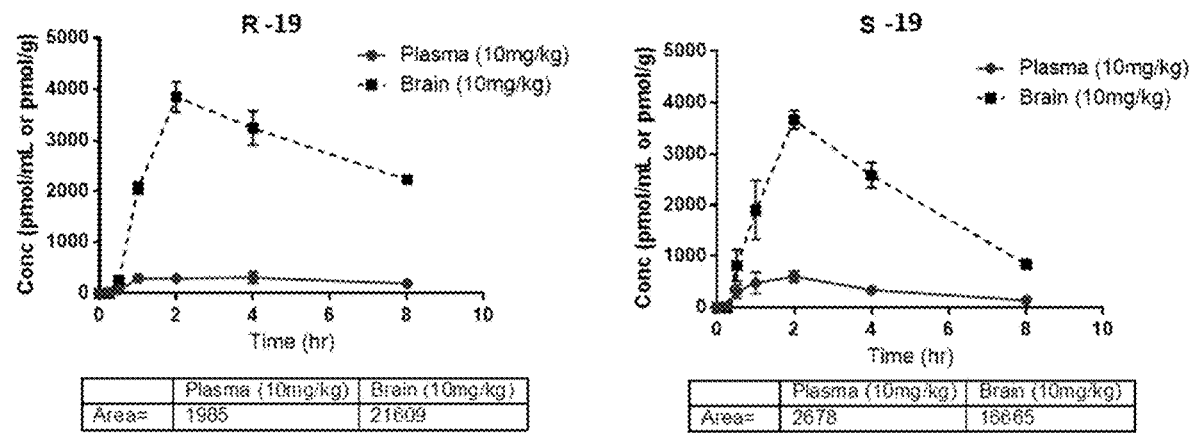

FIG. 12B shows each enantiomer of compound 19 orally administered at 10 mg/kg is orally available and highly brain penetrable with R-19 showing better brain/plasma ratio (11 vs 6) compared to the S enantiomer.

Example 9. Study of the Effect of Compound (±)-29 on Thermal Response in Rats

Figure 13:
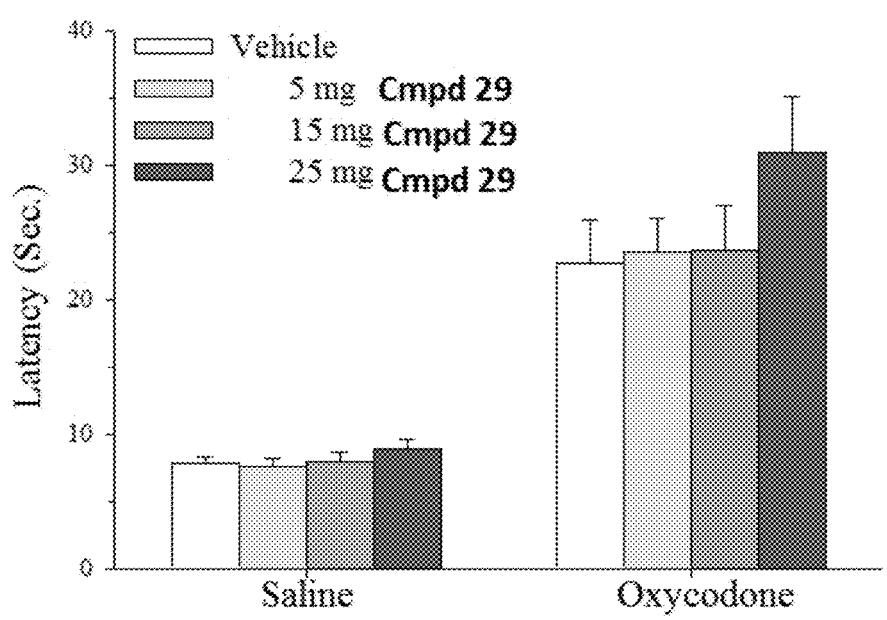
FIG. 13 Compound (±)-29 pretreatment showed no significant effects on animals' thermal response tested 30 minutes following either saline (1 ml/kg, i.p.) or oxycodone (2 mg/kg, i.p.) challenge indicating that (±)-29 has no effect on oxycodone induced analgesia and has no analgesic effects of its own.

Methods: Compound (±)-29 was administered 15 minutes before saline or oxycodone challenge. Tests were performed after the rat was placed inside a transparent circular cage on a hot plate (52±0.2° C.). Licking the hind paw or jumping was considered as a sign of thermal nociception. The rat was then immediately removed from the hot plate and the time latency was recorded. FIG. 13 illustrates compound (±)-29 pretreatment showed no significant effects on animal's thermal response tested 30 minutes following either saline (1 ml/kg, i.p.) or oxycodone (2 mg/kg, i.p.) challenge. Thus, the compound was found to block the reinforcing effects of oxycodone that can lead to addiction, it will not prevent analgesia produced by the drug.

The terms "a" and "an" do not denote a limitation of quantity, but rather denote the presence of at least one of the referenced item. The term "or" means "and/or". Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments. The modifier "about" used in connection with a quantity is inclusive of the stated value and has the meaning dictated by the context (e.g., includes the degree of error associated with measurement of the particular quantity).

The endpoints of all ranges directed to the same component or property are inclusive of the endpoints, are independently combinable, and include all intermediate points and ranges (e.g., ranges of "up to about 25 wt. %, or, more specifically, about 5 wt. % to about 20 wt. %," is inclusive of the endpoints and all intermediate values of the ranges of "about 5 wt. % to about 25 wt. %," such as about 10 wt % to about 23 wt %, etc.).

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A compound selected from the group consisting of
N-(4-(4-(3-chloro-5-ethyl-2-methoxyphenyl)piperazin-1-yl)-3-hydroxybutyl)-1H-indole-2-carboxamide;
(R)-N-(4-(4-(3-chloro-5-ethyl-2-methoxyphenyl)piperazin-1-yl)-3-hydroxybutyl)-1H-indole-2-carboxamide;
(S)-N-(4-(4-(3-chloro-5-ethyl-2-methoxyphenyl)piperazin-1-yl)-3-hydroxybutyl)-1H-indole-2-carboxamide;
N-(4-(4-(2-chloro-3-ethylphenyl)piperazin-1-yl)-3-hydroxybutyl)-1H-indole-2-carboxamide;
(R)-N-(4-(4-(2-chloro-3-ethylphenyl)piperazin-1-yl)-3-hydroxybutyl)-1H-indole-2-carboxamide;
(S)-N-(4-(4-(2-chloro-3-ethylphenyl)piperazin-1-yl)-3-hydroxybutyl)-1H-indole-2-carboxamide;
N-(4-(4-(3-chloro-5-ethyl-2-methoxyphenyl)piperazin-1-yl)-3-fluorobutyl)-1H-indole-2-carboxamide;
(R)-N-(4-(4-(3-chloro-5-ethyl-2-methoxyphenyl)piperazin-1-yl)-3-fluorobutyl)-1H-indole-2-carboxamide;
(S)-N-(4-(4-(3-chloro-5-ethyl-2-methoxyphenyl)piperazin-1-yl)-3-fluorobutyl)-1H-indole-2-carboxamide;
N-(4-(4-(3-chloro-5-ethyl-2-methoxyphenyl)piperazin-1-yl)-3-fluorobutyl)benzofuran-2-carboxamide;
(R)-N-(4-(4-(3-chloro-5-ethyl-2-methoxyphenyl)piperazin-1-yl)-3-fluorobutyl)benzofuran-2-carboxamide;
(S)-N-(4-(4-(3-chloro-5-ethyl-2-methoxyphenyl)piperazin-1-yl)-3-fluorobutyl)benzofuran-2-carboxamide;
N-(4-(4-(2-chloro-3-ethylphenyl)piperazin-1-yl)-3-fluorobutyl)-1H-indole-2-carboxamide;
(R)-N-(4-(4-(2-chloro-3-ethylphenyl)piperazin-1-yl)-3-fluorobutyl)-1H-indole-2-carboxamide;
(S)-N-(4-(4-(2-chloro-3-ethylphenyl)piperazin-1-yl)-3-fluorobutyl)-1H-indole-2-carboxamide;
N-(4-(4-(2-chloro-3-ethylphenyl)piperazin-1-yl)-3-fluorobutyl)benzofuran-2-carboxamide;
(R)-N-(4-(4-(2-chloro-3-ethylphenyl)piperazin-1-yl)-3-fluorobutyl)benzofuran-2-carboxamide; and
(S)-N-(4-(4-(2-chloro-3-ethylphenyl)piperazin-1-yl)-3-fluorobutyl)benzofuran-2-carboxamide;
a radioisotope thereof; or
a pharmaceutically acceptable salt thereof.

2. The compound of claim 1, comprising tritium, deuterium, $^{11}C$, $^{13}C$, $^{14}C$, $^{18}F$, or a combination thereof.

3. A pharmaceutical composition comprising a compound of claim 1, further comprising at least one pharmaceutically acceptable carrier.

4. The pharmaceutical composition of claim 3, wherein the composition is formulated as an injectable fluid, an aerosol, a cream, a gel, a tablet, a capsule, a syrup, an ophthalmic solution, or a transdermal patch.

5. A package comprising the pharmaceutical composition of claim 3 in a container and further comprising instructions for using the composition in order to treat a patient suffering from a substance use disorder, schizophrenia, depression, a bipolar disorder, or a dyskinesia associated with Parkinson's disease (PD) or treatment of PD with L-DOPA.

6. A method for treating a substance use disorder, schizophrenia, depression, a bipolar disorder, or a dyskinesia associated with Parkinson's disease (PD) or treatment of PD with L-DOPA in a patient, comprising providing a therapeutically effective amount of a compound of claim 1 to a patient in need thereof.

7. A method for treating a substance use disorder, schizophrenia, depression, a bipolar disorder, or a dyskinesia associated with Parkinson's disease (PD) or treatment of PD with L-DOPA in a patient, comprising providing a therapeutically effective amount of a compound of claim 1 along with at least one pharmaceutically acceptable carrier to a patient in need thereof.

8. The method of claim 6, wherein the substance of the substance use disorder is an opioid or a cannabinoid.

9. The compound of claim 1 selected from the group consisting of
N-(4-(4-(3-chloro-5-ethyl-2-methoxyphenyl)piperazin-1-yl)-3-hydroxybutyl)-1H-indole-2-carboxamide;
(R)-N-(4-(4-(3-chloro-5-ethyl-2-methoxyphenyl)piperazin-1-yl)-3-hydroxybutyl)-1H-indole-2-carboxamide; and
(S)-N-(4-(4-(3-chloro-5-ethyl-2-methoxyphenyl)piperazin-1-yl)-3-hydroxybutyl)-1H-indole-2-carboxamide;
a radioisotope thereof; or
a pharmaceutically acceptable salt thereof.

10. The compound of claim 1 selected from the group consisting of
N-(4-(4-(2-chloro-3-ethylphenyl)piperazin-1-yl)-3-hydroxybutyl)-1H-indole-2-carboxamide;
(R)-N-(4-(4-(2-chloro-3-ethylphenyl)piperazin-1-yl)-3-hydroxybutyl)-1H-indole-2-carboxamide; and
(S)-N-(4-(4-(2-chloro-3-ethylphenyl)piperazin-1-yl)-3-hydroxybutyl)-1H-indole-2-carboxamide;
a radioisotope thereof; or
a pharmaceutically acceptable salt thereof.

11. The compound of claim 1 selected from the group consisting of
N-(4-(4-(3-chloro-5-ethyl-2-methoxyphenyl)piperazin-1-yl)-3-fluorobutyl)-1H-indole-2-carboxamide;
(R)-N-(4-(4-(3-chloro-5-ethyl-2-methoxyphenyl)piperazin-1-yl)-3-fluorobutyl)-1H-indole-2-carboxamide; and
(S)-N-(4-(4-(3-chloro-5-ethyl-2-methoxyphenyl)piperazin-1-yl)-3-fluorobutyl)-1H-indole-2-carboxamide;
a radioisotope thereof; or
a pharmaceutically acceptable salt thereof.

12. The compound of claim 1 selected from the group consisting of
N-(4-(4-(3-chloro-5-ethyl-2-methoxyphenyl)piperazin-1-yl)-3-fluorobutyl)benzofuran-2-carboxamide;
(R)-N-(4-(4-(3-chloro-5-ethyl-2-methoxyphenyl)piperazin-1-yl)-3-fluorobutyl)benzofuran-2-carboxamide; and
(S)-N-(4-(4-(3-chloro-5-ethyl-2-methoxyphenyl)piperazin-1-yl)-3-fluorobutyl)benzofuran-2-carboxamide;
a radioisotope thereof; or
a pharmaceutically acceptable salt thereof.

13. The compound of claim 1 selected from the group consisting of
N-(4-(4-(2-chloro-3-ethylphenyl)piperazin-1-yl)-3-fluorobutyl)-1H-indole-2-carboxamide;
(R)-N-(4-(4-(2-chloro-3-ethylphenyl)piperazin-1-yl)-3-fluorobutyl)-1H-indole-2-carboxamide; and (S)-N-(4-(4-(2-chloro-3-ethylphenyl)piperazin-1-yl)-3-fluorobutyl)-1H-indole-2-carboxamide;
a radioisotope thereof; or
a pharmaceutically acceptable salt thereof.

14. The compound of claim 1 selected from the group consisting of

N-(4-(4-(2-chloro-3-ethylphenyl)piperazin-1-yl)-3-fluorobutyl)benzofuran-2-carboxamide;
(R)-N-(4-(4-(2-chloro-3-ethylphenyl)piperazin-1-yl)-3-fluorobutyl)benzofuran-2-carboxamide; and
(S)-N-(4-(4-(2-chloro-3-ethylphenyl)piperazin-1-yl)-3-fluorobutyl)benzofuran-2-carboxamide;
a radioisotope thereof; or
a pharmaceutically acceptable salt thereof.

* * * * *